(12) United States Patent
Hostetler et al.

(10) Patent No.: US 12,173,029 B2
(45) Date of Patent: Dec. 24, 2024

(54) ANTIVIRAL PRODRUGS, PHARMACEUTICAL FORMULATIONS, AND METHODS

(71) Applicant: THE REGENTS OF THE UNIVERSITY OF CALIFORNIA, Oakland, CA (US)

(72) Inventors: Karl Y. Hostetler, La Jolla, CA (US); James Beadle, La Jolla, CA (US); Nadejda Valiaeva, La Jolla, CA (US); Robert T. Schooley, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 18/006,330

(22) PCT Filed: Jul. 24, 2021

(86) PCT No.: PCT/US2021/043094
§ 371 (c)(1),
(2) Date: Jan. 20, 2023

(87) PCT Pub. No.: WO2022/020793
PCT Pub. Date: Jan. 27, 2022

(65) Prior Publication Data
US 2023/0287029 A1 Sep. 14, 2023

Related U.S. Application Data

(60) Provisional application No. 63/145,698, filed on Feb. 4, 2021, provisional application No. 63/110,596, filed on Nov. 6, 2020, provisional application No. 63/078,427, filed on Sep. 15, 2020, provisional application No. 63/070,695, filed on Aug. 26, 2020, provisional application No. 63/055,944, filed on Jul. 24, 2020.

(51) Int. Cl.
*C07H 7/06* (2006.01)
*A61P 31/14* (2006.01)
*C07H 9/02* (2006.01)

(52) U.S. Cl.
CPC .............. *C07H 7/06* (2013.01); *A61P 31/14* (2018.01); *C07H 9/02* (2013.01)

(58) Field of Classification Search
CPC .............. C07H 7/06; C07H 9/02; A61P 31/14
See application file for complete search history.

(56) References Cited

U.S. PATENT DOCUMENTS

| | | | |
|---|---|---|---|
| 5,484,908 A | 1/1996 | Froehler | |
| 5,645,985 A | 7/1997 | Froehler | |
| 5,830,653 A | 11/1998 | Froehler | |
| 5,990,303 A | 11/1999 | Seela | |
| 6,303,315 B1 | 10/2001 | Skouv | |
| 6,639,059 B1 | 10/2003 | Kochkine | |
| 8,835,630 B1 | 9/2014 | Hostetler | |
| 2003/0092905 A1 | 5/2003 | Kochkine | |
| 2013/0029940 A1 | 1/2013 | Hostetler et al. | |
| 2014/0364397 A1 | 12/2014 | Hostetler et al. | |
| 2019/0083520 A1 | 3/2019 | Painter et al. | |
| 2020/0197422 A1 | 6/2020 | Axt et al. | |
| 2022/0081455 A1 | 3/2022 | Lazerwith | |
| 2022/0143052 A1 | 5/2022 | Lazerwith | |

FOREIGN PATENT DOCUMENTS

| | | |
|---|---|---|
| WO | 2016044281 A1 | 3/2016 |
| WO | 2017048956 A1 | 3/2017 |
| WO | 2019053696 A1 | 3/2019 |
| WO | 2021222535 A1 | 11/2021 |
| WO | 2022046631 A1 | 3/2022 |
| WO | 2022081973 A1 | 4/2022 |
| WO | 2023146974 A2 | 8/2023 |
| WO | 2024159117 A1 | 8/2024 |

OTHER PUBLICATIONS

Yan & Muller, 11 ACS Med. Chem. Lett. 1361-1366 (2020) (Year: 2020).*
Carlin, et al., "1-O-Octadecyl-O-benzyl-sn-glyceryl-3-phospho-GS-441524 (V2043). Evaluation of Orval V2043 in a Mouse Model of SARS-CoV-2 Infection and Synthesis and Antiviral Evaluation of Additional Phospholipid Esters with Enhanced Anti-SARS-CoV-2 Activity", J. Med. Chem. 2023, 66, 5802-5819.
deWitt, et al., "Phophylactic and therapeutic remdesivir (GS-5734) treatment in the rhesus macaque model of MERS-CoV infection", PNAS, Mar. 24, 2020, vol. 117, No. 12, 6771-6776.
Gordon et al., "The antiviral compound remdesivir potentially inhibits RNA-dependent RNA polymerase from Middle East respiratory syndrome coronavirus" J. Biol. Chem. (2020) 295(15), 4773-4779.
Halldorsson et al., "Lipase-catalaysed kinetic resolution of 1-O-alkylglycerols by sequential transesterification", Tetrahedron: Assembly, 15 (2004) 2893-2899.
Lo et al., Broad-spectrum In Vitro Antiviral Activity of ODBG-P-RVn: An Orally-Available, Lipid-Modified Monophosphate Prodrug of Remdesivir Parent Nucleoside (GS-441524), Microbiology Spectrum, vol. 9, Issue 3.
Montoya, et al., "Enantiometric synthesis of natural alkyglycerols and their antibacterial and antibiofilm activities", Natural Product Research, 35:15, 2544-2550.

(Continued)

*Primary Examiner* — Timothy R Rozof
(74) *Attorney, Agent, or Firm* — Eversheds-Sutherland (US) LLP

(57) ABSTRACT

Compounds, including antiviral prodrugs, and pharmaceutical formulations including the compounds, which may be orally bioavailable or formulated for intramuscular injection. Methods for producing compounds, such as antiviral prodrugs. Methods for treating coronavirus and other RNA virus infection in mammals. Methods of producing a drug triphosphate.

39 Claims, 7 Drawing Sheets

(56) References Cited

OTHER PUBLICATIONS

Prujssers, et al., "Remdersivir Inhibits SARS-CoV-2 in Human Lung Cells and Chimeric SARS-CoV Expressing the SARS-CoV-2 RNA Polymerase in Mice", Cell Reports 32, 107940, Jul. 21, 2020.
Ruiz, et al., "Synthesis and antiviral evaluation of alkoxyalkyl-phosphate conjugates of cidofovir and adefovir", ScienceDirect, Antiviral Research, 75 (2007) 87-90.
Schooley, et al., "Rethinking Remdesivir: Synthesis, Antiviral Activity, and Pharmokinetics of Oral Lipid Prodrugs", Antimicrobial Agents and Chemotherapy, Oct. 2021, vol. 65, Issue 10, e01155-21.
Tempestilli, et al., "Pharmocokinetics of remdesivir and GS-441524 in two critically ill patients who recovered from COVID-10", J Antimicrob Chemother, 2020, 75:2977-2980.
Warren, et al., "Therpeutic efficacy of the small molecule of GS-5734 against Ebola virus inn rhesus monkeys", Nature, vol. 531, Mar. 17, 2016, 381-399.
Yan, et al., "Advantages of the Parent Nucleoside GS-441524 over Remdesivir for Covid-19 Treatment", ACS Med. Chem. Lett., 2020, 11, 1361-1366.
International Search Report and the Written Opinion for International Application No. PCT/US2021/043094, mailed Dec. 29, 2021, 10 pages.
Carlin, et al., "Oral pharmcokinetics and efficacy of oral phoshpolipid remdesivir nucleoside prodrugs against SARS-CoV-2 in mice", Antimicrobial Agents and Chemotherapy, American Society for Microbiology, pp. 1-13; Dowloaded from https://journals.asm.org/journal/aac on Sep. 6, 2024.
PCT International Search Report and Written Opinion for PCT/US2023/011639, mailed Apr. 30, 2024 (14 pages).
Schooley, et al., "Rethinking Remdesivir: Synthesis of Lipid Prodrugs that Substantially Enchance Anti-Coronavirus Activity", https://doi.org/10.1101/2020.08.26.269159, Posted Aug. 27, 2020.

\* cited by examiner

ANTIVIRAL PRODRUGS, PHARMACEUTICAL FORMULATIONS, AND METHODS

CROSS REFERENCE TO RELATED APPLICATIONS

This application is a U.S. National Phase Application of PCT Application No. PCT/US2021/043094, filed on Jul. 24, 2021, which claims priority to U.S. Provisional Patent Application No. 63/145,698, filed Feb. 4, 2021, U.S. Provisional Patent Application No. 63/110,596, filed Nov. 6, 2020, U.S. Provisional Patent Application No. 63/078,427, filed Sep. 15, 2020, U.S. Provisional Patent Application No. 63/070,695, filed Aug. 26, 2020, and U.S. Provisional Patent Application No. 63/055,944, filed Jul. 24, 2020, which are incorporated herein by reference.

STATEMENT REGARDING FEDERALLY SPONSORED RESEARCH OR DEVELOPMENT

This invention was made with government support under grant no. AI131424 awarded by the National Institutes of Health. The government has certain rights in the invention.

TECHNICAL FIELD

The present invention relates to antiviral prodrugs, methods for producing antiviral prodrugs, and methods of use for treatment of coronavirus infections in mammals.

BACKGROUND

During the last two decades, spillover events have introduced the highly transmissible beta-coronavirus strains SARS CoV, MERS CoV, SARS CoV-2 into the human population. Although case fatality ratios have varied, each has demonstrated the ability to induce substantial morbidity and mortality—especially among those over 55 and/or those with underlying co-morbid medical conditions. Although SARS CoV and MERS CoV were largely contained by epidemiological interventions, SARS CoV-2 evolved into a global pandemic.

The effort to develop SARS CoV-2 vaccines was challenged by strain diversity, the possibility that vaccine-induced immunity will be short lived, potentially reduced immune recognition by individuals as young as 30, and the possibility that antibody dependent enhancement may be observed. Reported cases of reinfection have raised substantial new concerns about long-lasting immunity—even after recovery from natural infection. While there is hope that the SARS CoV-2 vaccine effort will succeed, after a third of a century the AIDS vaccine is, alas, still undeveloped. A highly successful drug development effort changed the face of HIV by providing extremely effective, affordable and scalable prevention and treatment tools. During the coronavirus vaccine effort, it would be desirable to mount an equally intense therapeutics effort.

Remdesivir nucleoside triphosphate (RVn triphosphate) potently inhibits enzymatic activity of the polymerase of every coronavirus tested thus far, including SARS CoV-2 (see, e.g., Yan, V. C. et al. ACS Med. Chem. Lett. 2020; 11(7): 1361-1366).

This broad activity may reflect the relative molecular conservation of the coronavirus RNA dependent RNA polymerase (RdRp). Remdesivir (RDV) is an aryloxy phosphoramidate triester prodrug that must be converted by a series of reactions to RVn triphosphate, the active antiviral metabolite. Although RVn-triphosphate is an excellent inhibitor of the viral RdRp (see, e.g., Gordon, C. J. et al. J. Biol. Chem. 2020; 295: 4773-4779), RDV's antiviral activity is highly variable in different cell types which may be due to variable expression of the four enzymes required for conversion to RVn-P (Yan, V. C. et al. ACS Med. Chem. Lett. 2020; 11(7): 1361-1366). RDV's base is a 1'-cyano-substituted adenine C nucleoside (GS-441524, RVn) that is thought to be poorly phosphorylated. To bypass the perceived slow first phosphorylation the developers relied on an aryloxy phosphoramidate triester prodrug that is converted by a complex series of four reactions to remdesivir nucleoside monophosphate (RVn-P) that is then efficiently converted to RVn triphosphate, the active metabolite. RDV may be more active in some SARS-CoV-2 infected tissues than in others, a possible reason for its incomplete clinical impact on SARS-CoV-2.

Remdesivir has beneficial antiviral and clinical effects in animal models of coronavirus infection (see, e.g., de Wit, E. et al. Proc. Natl. Acad. Sci. USA, 2020; 115:6771-6776). These effects are primarily demonstrable when administered before or very soon after viral challenge. RDV is not highly bioavailable following oral administration and must be administered intravenously, functionally limiting its clinical application to hospitalized patients with relatively advanced disease. Also, RDV's persistence in plasma is known to be very short.

Specifically, RDV is a prodrug designed to bypass the first phosphorylation of the remdesivir nucleoside (RVn) which may be rate limiting in the synthesis of RVn-triphosphate, the active metabolite. However, this approach does not appear to provide any benefit in Vero E6 cells, a monkey kidney cell line (see, e.g., Pruijssers, A. J. et al., Cell Rep. 2020 Jul. 21; 32(3):107940), and by the results showing that the antiviral activity of RVn is greater than that of RDV. Other perceived disadvantages of RDV include a lack of oral bioavailability, a difficult synthesis, instability in plasma, inadequate delivery to lung, and/or hepatotoxicity. In patients with Covid-19 and in the Syrian hamster model of SARS-CoV-2 disease, in addition to high viral loads in nasal turbinate, trachea and lung, many other tissues are infected with SARS-CoV-2 as the infection proceeds including intestine, heart, liver, spleen, kidney, brain, lymph nodes, and vascular endothelium. However, RDV antiviral activity appears to vary widely in lung and kidney cell lines with $EC_{50}$ values of 1.65 µM in Vero E6 cells, 0.28 µM in Calu3 2B4, 0.010 µM in human alveolar epithelial cells (HAE), a 165-fold difference (see, e.g., Pruijssers, A. J. et al., Cell Rep. 2020 Jul. 21; 32(3):107940). It has been suggested that this may be due to variable amounts of the enzymes which convert RDV to RVn-P (see, e.g., Yan, V. C. et al. ACS Med. Chem. Lett. 2020; 11(7): 1361-1366).

There remains a need for a highly active and/or orally bioavailable analog of RVn, which may provide sustained levels of intact antiviral drug in plasma, including those that provide increased oral bioavailability by improving lung exposure to the active antiviral.

BRIEF SUMMARY

Provided herein are compounds, such as antiviral prodrugs, and pharmaceutical formulations that overcome one or more of the disadvantages of currently used drugs. For example, embodiments of the compounds and pharmaceutical formulations provided herein include orally useful antiviral prodrugs that may specifically target organs where viral replication is maximal and be conveniently administered at scale in any disease stage. For oral use and enhanced lung exposure, embodiments of the new prodrugs of RVn provided herein can accomplish one or more of three steps: 1) kinase bypass of the first nucleoside phosphorylation, 2) provide increased oral bioavailability and, 3) deliver antivirally significant concentrations to lung and gastrointestinal tract. Also provided herein are methods for the synthesis and antiviral evaluation of the compounds, including novel lipophilic prodrugs of RVn-monophosphate that are substantially more active than remdesivir in Vero E6 cells infected with SARS-CoV-2. Not wishing to be bound by any particular theory, embodiments of the compounds herein are prodrugs that may allow earlier and/or more effective treatment at the time of diagnosis of SARS-CoV-2 infection. The prodrugs herein may represent an approach that may be able to target the antiviral to the lung and away from the liver where remdesivir's major dose limiting is directed.

In one aspect, compounds, including antiviral prodrugs, are provided herein. In some embodiments, the compounds have a structure according to formula (I):

$$R-(O-L)_x-O-\overset{\overset{O}{\|}}{\underset{\underset{Y}{O}}{P}}-O-Nuc;$$ formula (I)

wherein Nuc is selected from the group consisting of an antiviral nucleoside and an antiviral nucleoside analog; Y is independently selected from the group consisting of hydrogen, a $C_1$-$C_{30}$ hydrocarbyl, a pharmaceutically acceptable cation, and a covalent bond to a carbon atom of a five-carbon sugar moiety of the antiviral nucleoside or the antiviral nucleoside analog; x is 0 or 1; L is a $C_1$-$C_6$ hydrocarbyl; and R is independently selected from the group consisting of a $C_{10}$-$C_{30}$ hydrocarbyl and a substituent of formula (A);

formula (A)

wherein $R^1$ and $R^2$ are independently selected from the group consisting of hydrogen and a $C_1$-$C_{30}$ hydrocarbyl.

In another aspect, pharmaceutical formulations are provided. In some embodiments, the pharmaceutical formulations include one or more compounds described herein. The pharmaceutical formulations may be formulated for intramuscular injection.

The pharmaceutical formulations may be orally bioavailable.

In a further aspect, methods of treatment are provided, such as methods for treating a virus (e.g., coronavirus), including virus infections in mammals. In some embodiments, the methods include administering an effective amount of a compound described herein, or a pharmaceutical formulation described herein.

In a still further aspect, methods of producing a compound, such as a prodrug, are provided. In some embodiments, the methods include (i) providing a compound of formula (a)—

$$R-(O-L)_x-O-\overset{\overset{O}{\|}}{\underset{\underset{Y}{O}}{P}}-OH;$$ formula (a)

(ii) providing a compound of formula (b)— formula (b)

(iii) contacting the compound of formula (a) and the compound of formula (b) to form a compound of formula (c)— formula (c)

and (iv) contacting the compound of formula (c) with an acid to form a compound of formula (d)— formula (d)

wherein Het is a $C_1$-$C_{30}$ hydrocarbyl comprising at least one heteroatom; Y is selected from the group consisting of hydrogen, a $C_1$-$C_{30}$ hydrocarbyl, and a pharmaceutically acceptable cation; x is 0 or 1; L is a $C_1$-$C_6$ hydrocarbyl; and R is selected from the group consisting of a $C_{10}$-$C_{30}$ hydrocarbyl and a substituent of formula (A);

formula (A)

wherein $R^1$ and $R^2$ are independently selected from the group consisting of hydrogen and a $C_1$-$C_{30}$ hydrocarbyl. The methods may include performing an intramolecular esterification reaction of a product, such as a phosphodiester, to form a cyclic phosphate, such as a 3',5'-cyclic phosphate.

In yet another aspect, methods of producing a drug triphosphate also are provided. In some embodiments, the methods include providing a plurality of cells, contacting the plurality of cells with an amount of a drug, incubating the plurality of cells and the amount of the drug for period effective to form the drug triphosphate.

Additional aspects will be set forth in part in the description which follows, and in part will be obvious from the description, or may be learned by practice of the aspects described herein. The advantages described herein may be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1A:
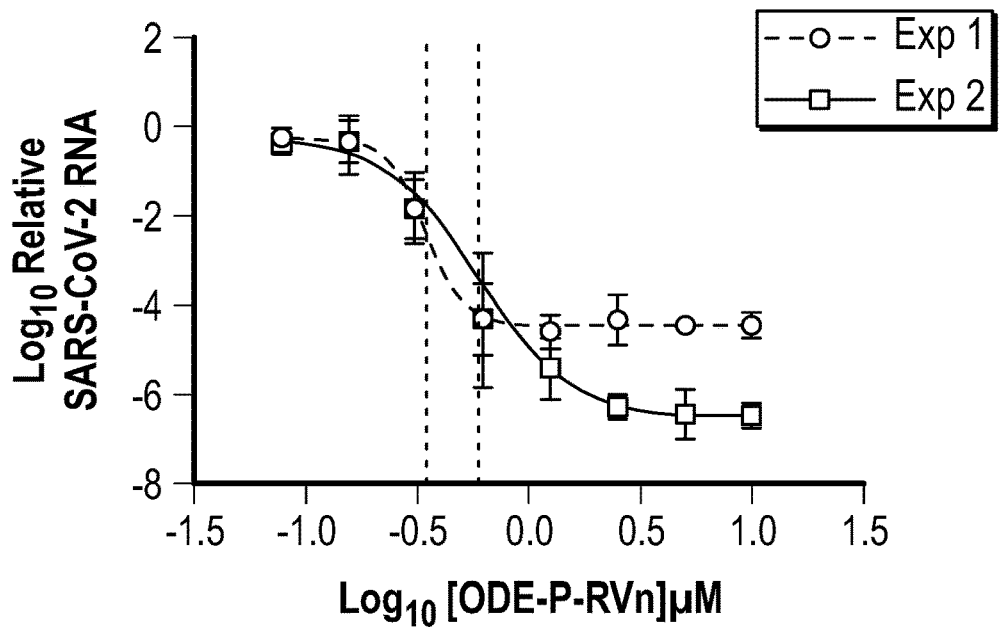
FIG. 1A depicts concentration-response curves for an embodiment of a compound described herein for SARS-CoV-2 infection in Vero E6 cells in two separate experiments performed in duplicate.
Figure 1B:
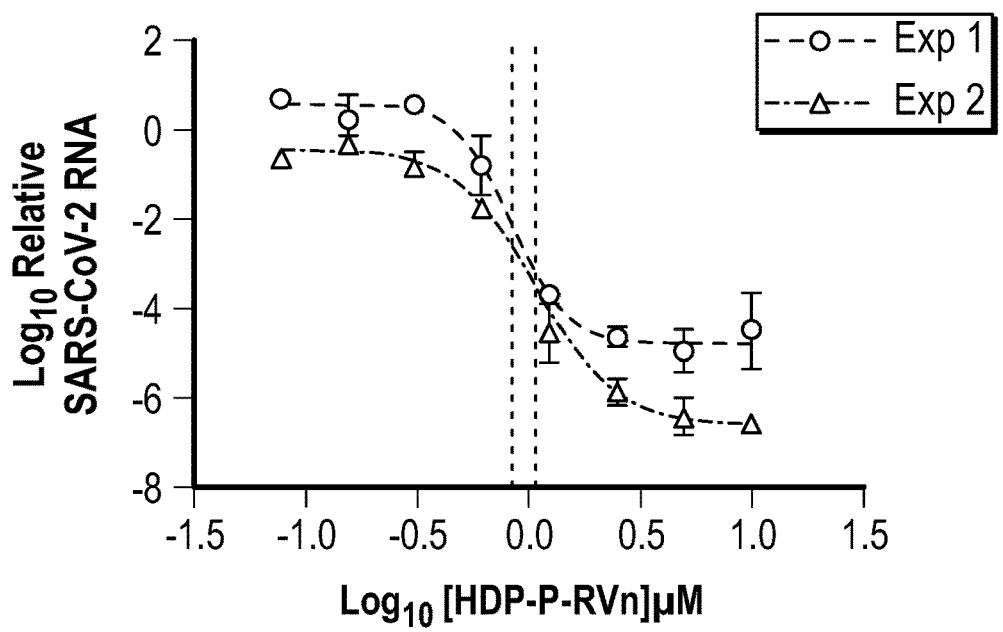
FIG. 1B depicts concentration-response curves for an embodiment of a compound described herein for SARS-CoV-2 infection in Vero E6 cells in two separate experiments performed in duplicate.
Figure 1C:
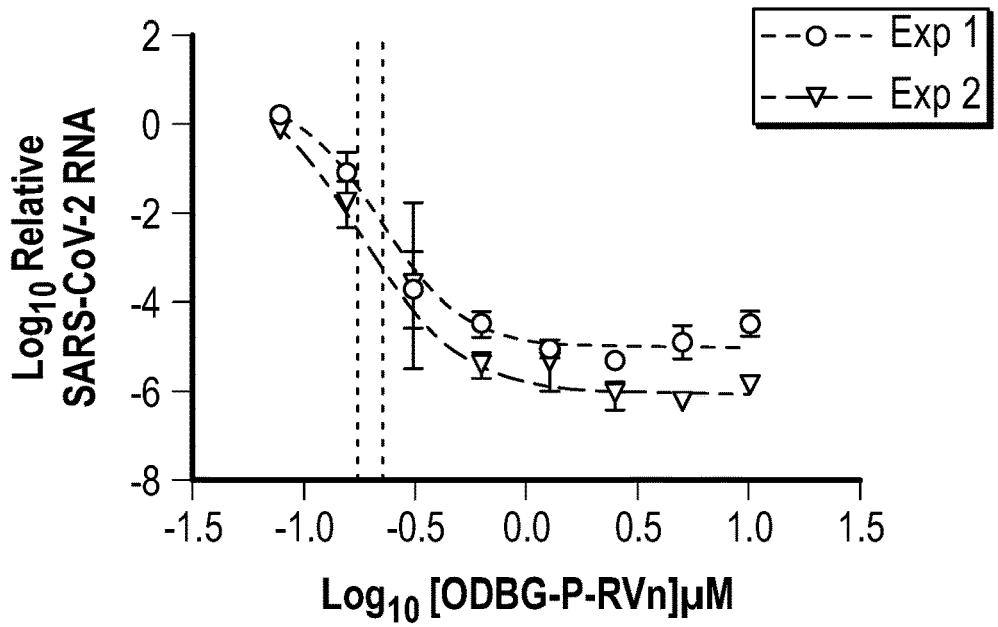
FIG. 1C depicts concentration-response curves for an embodiment of a compound described herein for SARS-CoV-2 infection in Vero E6 cells in two separate experiments performed in duplicate.
Figure 1D:
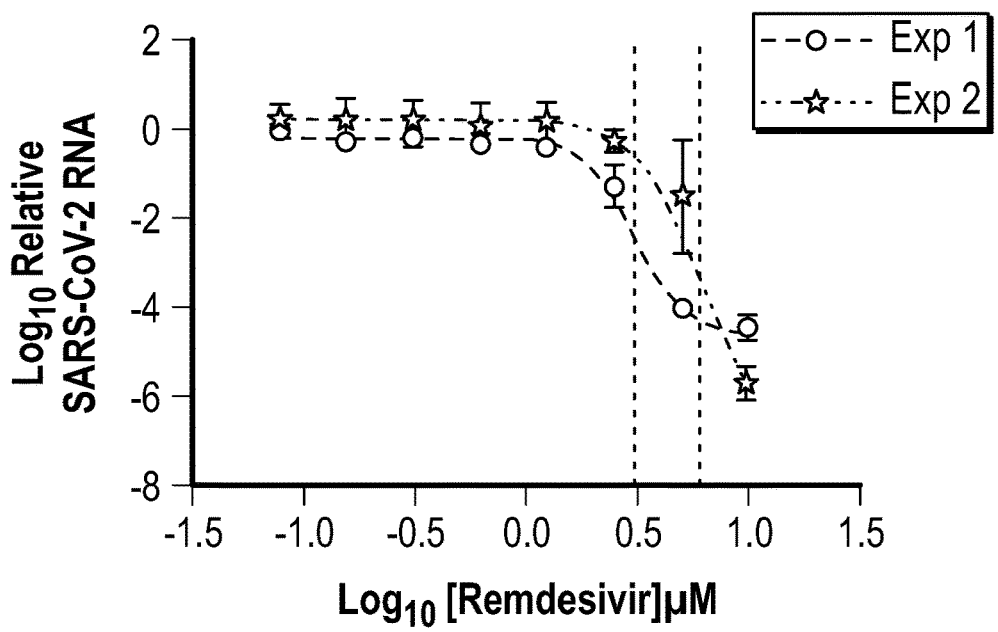
FIG. 1D depicts concentration-response curves for remdesivir for SARS-CoV-2 infection in Vero E6 cells in two separate experiments performed in duplicate.
Figure 1E:
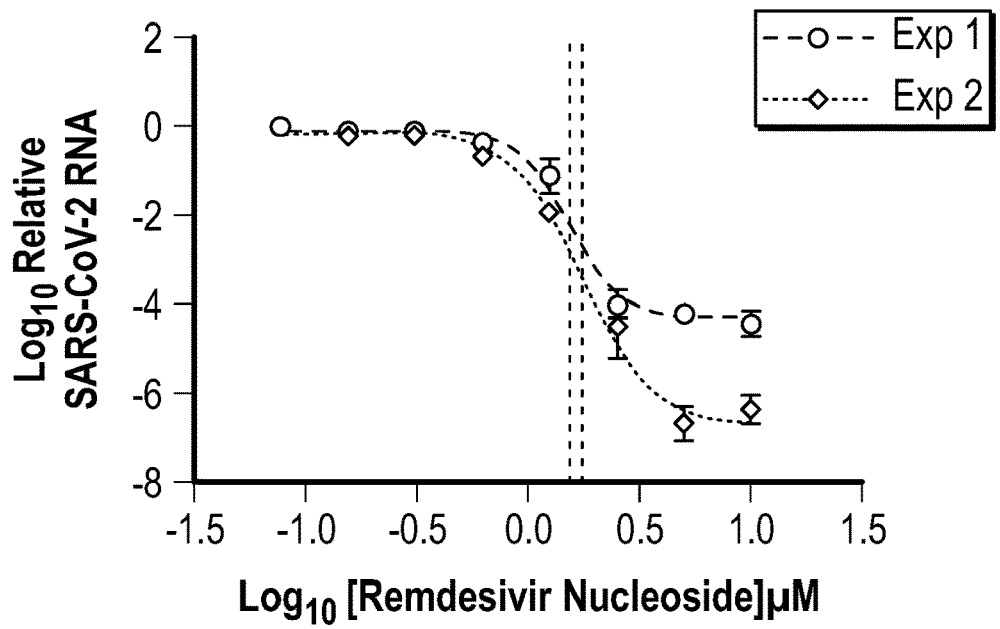
FIG. 1E depicts concentration-response curves for a remdesivir nucleoside for SARS-CoV-2 infection in Vero E6 cells in two separate experiments performed in duplicate.

In one aspect, compounds are provided herein, including compounds of formula formula (I)

$$R-(O-L)_x-O-\overset{O}{\underset{\underset{Y}{O}}{\overset{\|}{P}}}-O-Nuc.$$

The "Nuc" of formula (I) may be any suitable nucleoside. The nucleoside may be bonded to a compound in any manner. For example, a 5'-hydroxyl of a nucleoside may be joined to a phosphate moiety as an ester bond.

The nucleoside, in some embodiments, is an antiviral nucleoside. The antiviral nucleoside may be an antiviral ribonucleoside. The nucleoside, in some embodiments, is an antiviral nucleoside analog. The antiviral nucleoside analog may be an antiviral ribonucleoside analog.

In some embodiments, Nuc is RVn (GS-441524), beta-D-N4-hydroxycytidine (NHC), or (2'R)-2-amino-2'-deoxy-2'-fluoro-N,2'-dimethyladenosine (CAS # is 1998705-62-6). In some embodiments, Nuc is GS-441524, and the compound of formula (I) has the following structure:

Other antivirals for coronavirus infection can also be modified in the manner provided herein. For example, $N^4$-hydroxy-cytidine (NHC) is an antiviral candidate entering clinical Phase I evaluation. Other nucleoside analogs known to inhibit RNA viruses are also suitable for modification according to this disclosure.

The "Y" of formula (I) may be any of the substituents described herein. In some embodiments, Y is hydrogen, a $C_1$-$C_{30}$ hydrocarbyl, a pharmaceutically acceptable cation, or a covalent bond to a carbon atom of a five-carbon sugar moiety of the antiviral nucleoside or the antiviral nucleoside analog.

When Y is a covalent bond to a carbon atom of a five-carbon sugar moiety of the antiviral nucleoside or the antiviral nucleoside analog, the covalent bond may be a covalent bond to any carbon atom of a five-carbon sugar moiety of the antiviral nucleoside or the antiviral nucleoside analog (e.g., the 1' carbon, the 2' carbon, the 3' carbon, or the 4' carbon). In other words, the covalent bond may be a covalent bond between (i) the oxygen to which Y is bonded in formula (I), and (ii) any carbon atom of a five-carbon sugar moiety of the antiviral nucleoside or the antiviral nucleoside analog (e.g., the 1' carbon, the 2' carbon, the 3' carbon, or the 4' carbon). For example, Nuc may be GS-441524; the covalent bond may be between the oxygen to which Y is bonded in formula (I), and the 3' carbon of five-carbon sugar moiety of GS-441524, and the compound of formula (I) has the following structure:

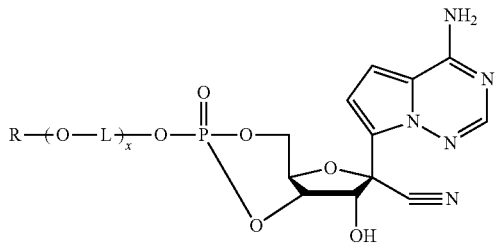

When Y is a pharmaceutically acceptable cation, the pharmaceutically acceptable cation may be $Na^+$.

In some embodiments, Y is a $C_1$-$C_{20}$ hydrocarbyl, a $C_1$-$C_{10}$ hydrocarbyl, or a $C_1$-$C_6$ hydrocarbyl. In some embodiments, Y is a $C_1$-$C_6$ alkyl, which may be unsubstituted. In some embodiments, Y includes at least one cyclic moiety. The at least one cyclic moiety may be a monocyclic moiety or a multicyclic moiety, e.g., a bicyclic moiety, a spiro moiety, etc. In some embodiments, Y is aryl, arylalkyl, heteroaryl, heteroarylalkyl, or heterocycloalkyl, each of which may be unsubstituted or substituted. In some embodiments, Y is an unsubstituted or substituted pyridinyl. In some embodiments. Y is an unsubstituted or substituted benzyl. The unsubstituted or substituted benzyl may have a structure according to formula (B):

formula (B)

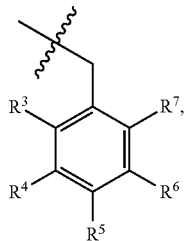

wherein $R^3$, $R^4$, $R^5$, $R^6$, and $R^7$ are independently selected from the group consisting of hydrogen, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, 0-carbamyl, N-carbamyl, 0-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino, and di-substituted amino. In some embodiments, $R^3$, $R^4$, $R^5$, $R^6$, and $R^7$ are hydrogen. In some embodiments, at least two of $R^3$, $R^4$, $R^5$, $R^6$, and $R^7$ are hydrogen. In some embodiments, at least three of $R^3$, $R^4$, $R^5$, $R^6$, and $R^7$ are hydrogen. In some embodiments, at least four of $R^3$, $R^4$, $R^5$, $R^6$, and $R^7$ are hydrogen.

When Y is an unsubstituted or substituted benzyl of formula (B), the compound of formula (I) has the following structure:

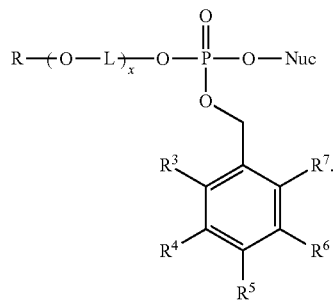

In formula (I), x may be 1 or 0. When x is 1, the "—O-L-" moiety is present in the compounds of formula (I). When x is 0, R is bonded directed to the oxygen of the phosphonate moiety, as shown in the following structure:

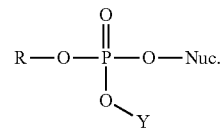

When "L" is present in the compounds of formula (I), the "L" may be selected from any of the substituents described herein. In some embodiments, L is a $C_1$-$C_{30}$ hydrocarbyl, a $C_1$-$C_{20}$ hydrocarbyl, a $C_1$-$C_{10}$ hydrocarbyl, a $C_1$-$C_6$ hydrocarbyl, a $C_1$-$C_5$ hydrocarbyl, a $C_1$-$C_4$ hydrocarbyl, a $C_1$-$C_3$ hydrocarbyl, or a $C_1$-$C_2$ hydrocarbyl. In some embodiments, L is an ethyl, which may be unsubstituted. In some embodiments, L is a methyl, which may be unsubstituted. In some embodiments, L is a propyl, which may be unsubstituted.

The "R" of formula (I) may be selected from any of the substituents described herein. In some embodiments, R is a $C_1$-$C_{30}$ hydrocarbyl, a $C_5$-$C_{30}$ hydrocarbyl, a $C_{10}$-$C_{30}$ hydrocarbyl, a $C_{12}$-$C_{24}$ hydrocarbyl, a $C_{13}$-$C_{29}$ hydrocarbyl, a $C_{15}$-$C_{24}$ hydrocarbyl, or a $C_{20}$-$C_{24}$ hydrocarbyl. R, in some embodiments, is a heteroalkyl. R may include 0 to 6 unsaturated bonds, 1 to 6 unsaturated bonds, 2 to 6 unsaturated bonds, 3 to 6 unsaturated bonds, or 4 to 6 unsaturated bonds. The "unsaturated bonds" described herein may include any non-single bond, and when more than one unsaturated bond is present, the two or more unsaturated bonds may be selected independently from a double bond or a triple bond. When one or more double bonds are present, the one or more double bonds may be cis-, trans-, or a combination thereof. R may include a cyclopropyl moiety, such as a terminal cyclopropyl moiety.

In some embodiments, R is—

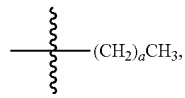

wherein a is 1 to 29. In some embodiments, a is 15 to 25. In some embodiments, a is 18 to 22. In some embodiments, a is 19. In some embodiments, a is 6 to 10. In some embodiments, a is 8.

In some embodiments R is—

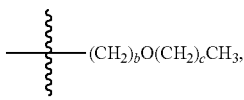

wherein b is 1 to 29, c is 0 to 28, and a sum of b and c is 29 or less. In some embodiments, b is 1 to 4 and c is 15 to 20. In some embodiments, b is 3 and c is 15. In some embodiments, b is 2 and c is 17.

In some embodiments, R is a substituent of formula (A);

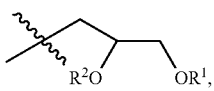

formula (A)

wherein $R^1$ and $R^2$ are hydrogen or a $C_1$-$C_{30}$ hydrocarbyl, such as a $C_{10}$-$C_{30}$ hydrocarbyl, or a $C_{12}$-$C_{24}$ hydrocarbyl. $R^1$, $R^2$, or both $R^1$ and $R^2$ may include at least one cyclic moiety, which may be a monocyclic moiety or a multicyclic moiety, e.g., a bicyclic moiety, a spiro moiety, etc. $R^1$, $R^2$, or both $R^1$ and $R^2$ may include 0 to 6 unsaturated bonds, 1 to 6 unsaturated bonds, 2 to 6 unsaturated bonds, 3 to 6 unsaturated bonds, or 4 to 6 unsaturated bonds. When one or more double bonds are present, the one or more double bonds may be cis-, trans-, or a combination thereof. $R^1$, $R^2$, or both $R^1$ and $R^2$ may include a branched hydrocarbyl, such as a penultimate branched hydrocarbyl. In some embodiments, at least one of $R^1$ and $R^2$ are hydrogen. In some embodiments, both $R^1$ and $R^2$ are independently selected from a $C_1$-$C_{30}$ hydrocarbyl.

In some embodiments, $R^1$, $R^2$, or both $R^1$ and $R^2$ are independently selected from the group consisting of aryl, arylalkyl, heteroaryl, heteroarylalkyl, and heterocycloalkyl, each of which may be unsubstituted or substituted. The arylalkyl may be an unsubstituted or substituted benzyl. The unsubstituted or substituted benzyl may have a structure according to formula (C):

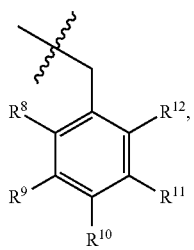

formula (C)

wherein $R^8$, $R^9$, $R^{10}$, $R^{11}$, and $R^{12}$ are independently selected from the group consisting of hydrogen, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino, and di-substituted amino. In some embodiments, each of $R^8$, $R^9$, $R^{10}$, $R^{11}$, and $R^{12}$ are hydrogen. In some embodiments, at least two of $R^8$, $R^9$, $R^{10}$, $R^{11}$, and $R^{12}$ are hydrogen.

In some embodiments, at least three of $R^8$, $R^9$, $R^{10}$, $R^{11}$, and $R^{12}$ are hydrogen. In some embodiments, at least four of $R^8$, $R^9$, $R^{10}$, $R^{11}$, and $R^{12}$ are hydrogen. In some embodiments, at least five of $R^8$, $R^9$, $R^{10}$, $R^{11}$, and $R^{12}$ are hydrogen.

In some embodiments, $R^1$ is—

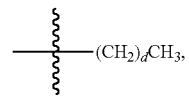

wherein d is 1 to 29. In some embodiments, d is 5 to 29, 10 to 29, 15 to 29, 20 to 29, 25 to 29, 1 to 25, 1 to 20, 1 to 15, 1 to 10, or 1 to 5.

In some embodiments, $R^1$ is

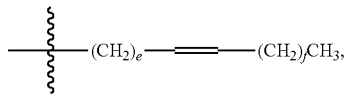

wherein e is 1 to 27, f is 0 to 26, and a sum of e and f is 27 or less.

In some embodiments, $R^2$ is selected from the group consisting of—

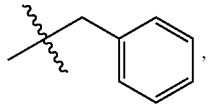
(A)

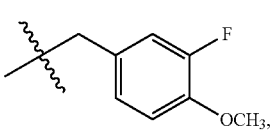
(B)

(C)

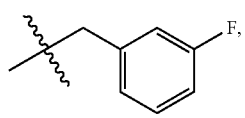
(D)

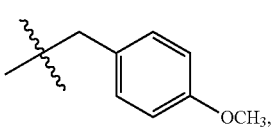
(E)

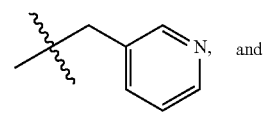
(F)

and

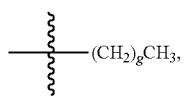    (G)

wherein g is 1 to 29. In some embodiments, g is 5 to 10. In some embodiments, g is 7.

The substituent of formula (A) may be a racemate, an sn-1 stereoisomer, or an sn-3 stereoisomer. Throughout this disclosure, when a formula, such as formula (A), is depicted with no indication(s) of spatial orientation, then the formula reads on all isomers, e.g., stereoisomers, of the compounds of the formula. For example, in some embodiments, a compound may have a structure according to formula (I), wherein x is 0, and R is a substituent of formula (A):

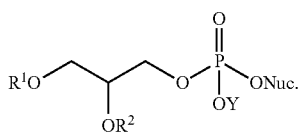

This formula lacks any indication of spatial orientation, and therefore reads on the sn-3 isomer thereof, the sn-1 isomer thereof, and mixtures of the sn-3 and sn-1 isomers, including racemic mixtures thereof:

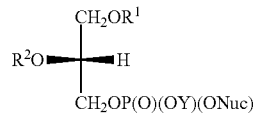

sn-3 isomer

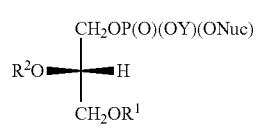

sn-1 isomer

Further non-limiting embodiments of compounds of formula (I) are provided at the following table:

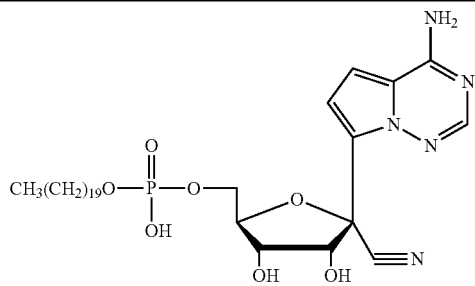

eicosyl-phospho-RVn

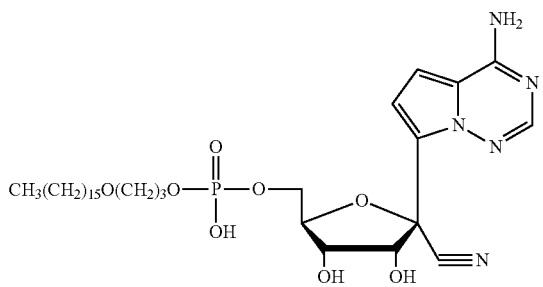

hexadecyloxypropyl-phospho-RVn

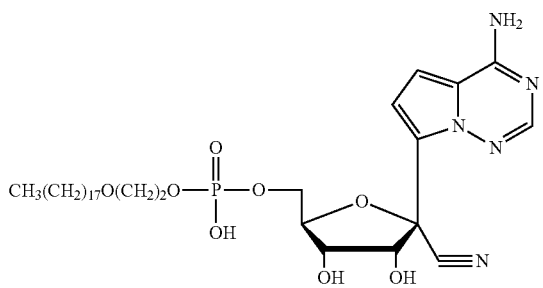

octadecyloxyethyl-phospho-RVn

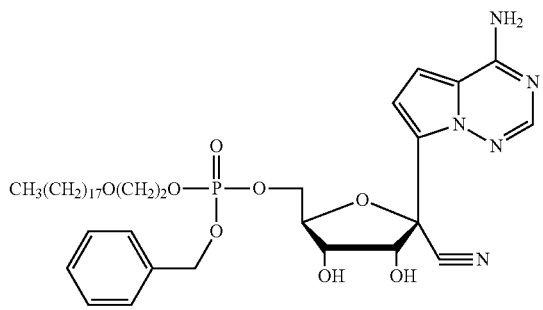
octadecyloxyethyl-benzyl-phospho-RVn
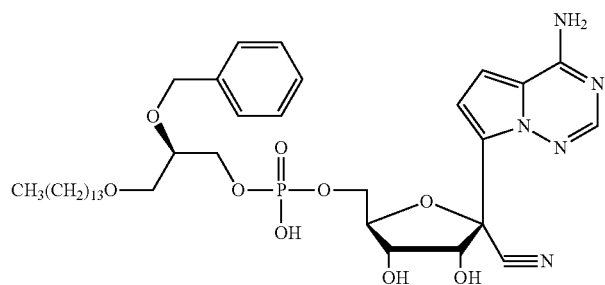
1-O-tetradecyl-2-O-benzyl-sn-glyceryl-phospho-RVn
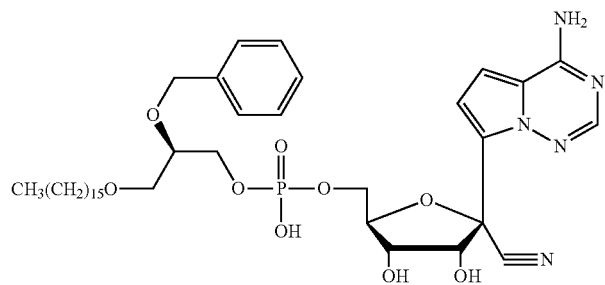
1-O-hexadecyl-2-O-benzyl-sn-glyceryl-phospho-RVn
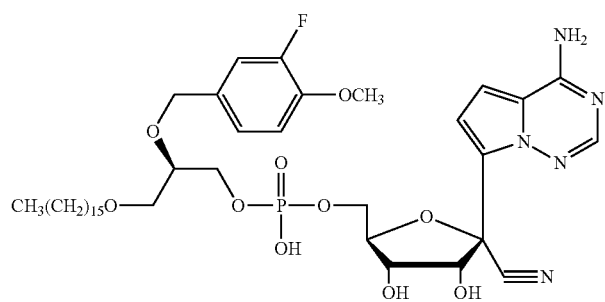
1-O-hexadecyl-2-O-(3-fluoro, 4-methoxybenzyl)-sn-glyceryl-phospho-RVn

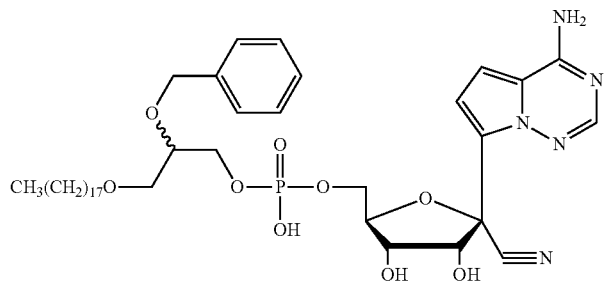
1-O-octadecyl-2-O-benzyl-rac-glyceryl-
phospho-RVn
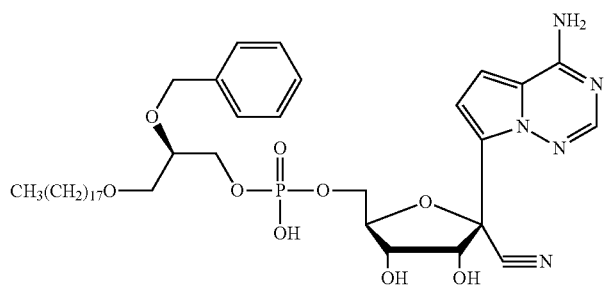
1-O-octadecyl-2-O-benzyl-sn-glyceryl-
phospho-RVn
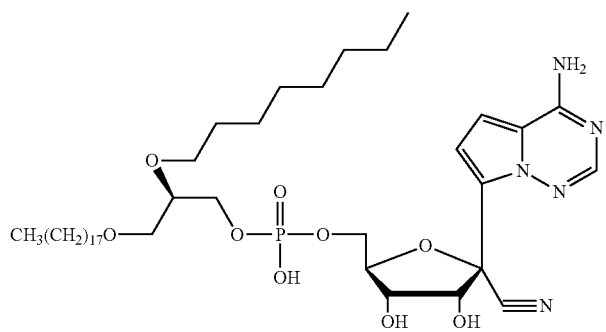
1-O-octadecyl-2-O-octyl-sn-glyceryl-
phospho-RVn
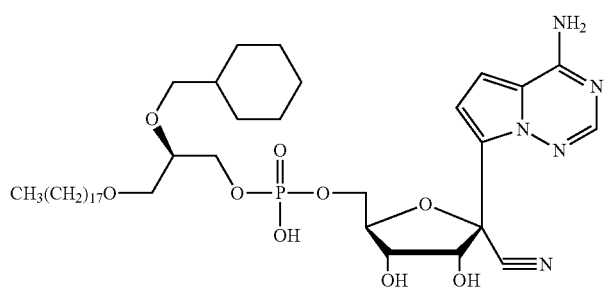
1-O-octadecyl-2-O-(methylcyclohexyl)-
sn-glyceryl-phospho-RVn

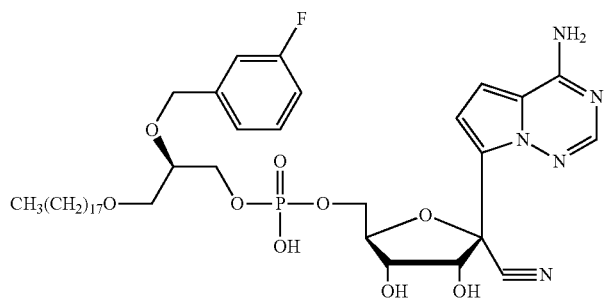
1-O-octadecyl-2-O-(3-fluorobenzyl)-
sn-glyceryl-phospho-Rvn
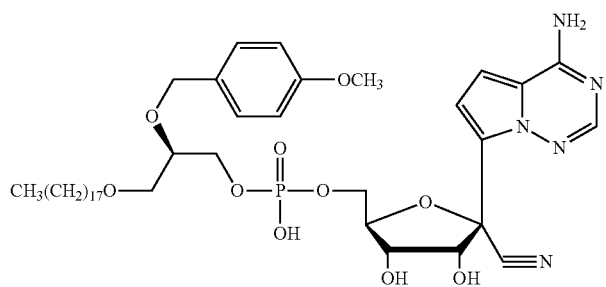
1-O-octadecyl-2-O-(4-methoxybenzyl)-
sn-glyceryl-phospho-RVn
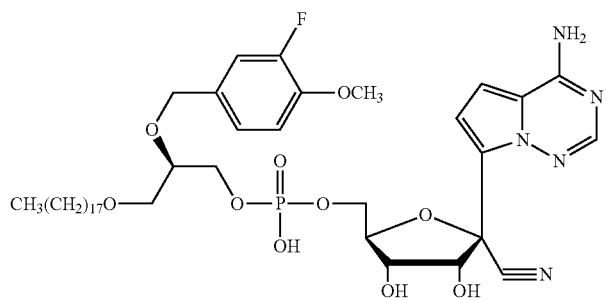
1-O-octadecyl-2-O-(3-fluoro, 4-methoxybenzyl)-
sn-glyceryl-phospho-RVn
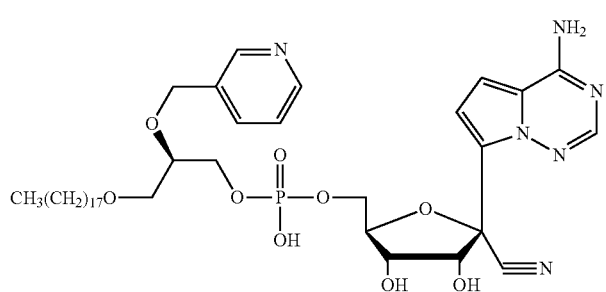
1-O-octadecyl-2-O-(methylpyridinyl)-
sn-glyceryl-phospho-RVn -continued
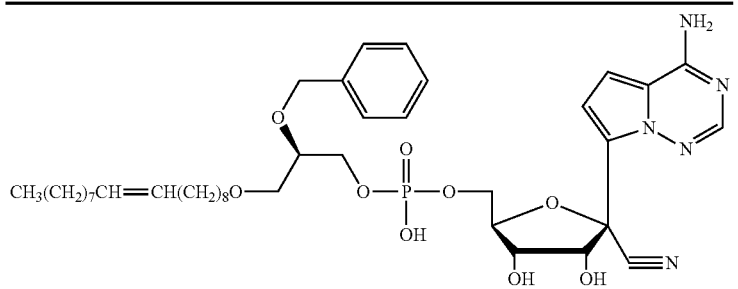
1-O-oleyl-2-O-benzyl-sn-glyceryl-phospho-RVn
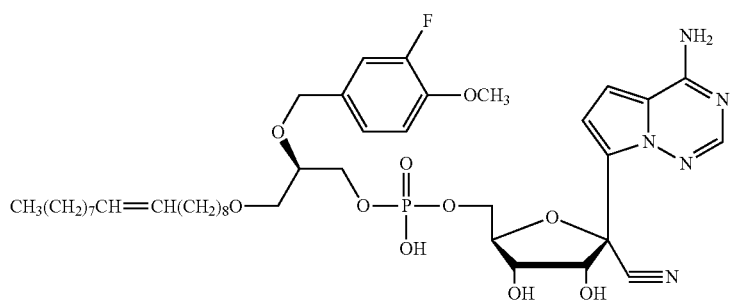
1-O-oleyl-2-O-(3-fluoro, 4-methoxybenzyl)-sn-glyceryl-phospho-RVn
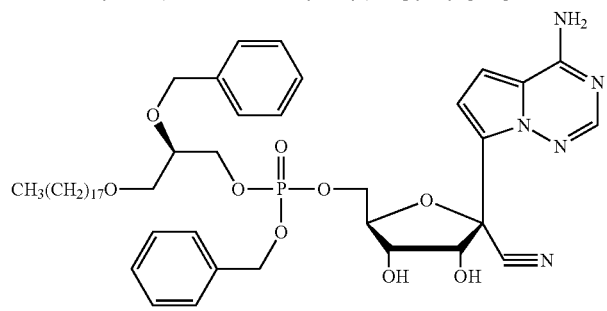
1-O-octadecyl-2-O-benzyl-benzyl-sn-glyceryl-phospho-RVn
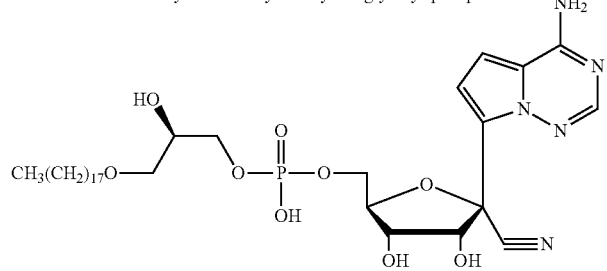
1-O-octadecyl-sn-glyceryl-phospho-RVn
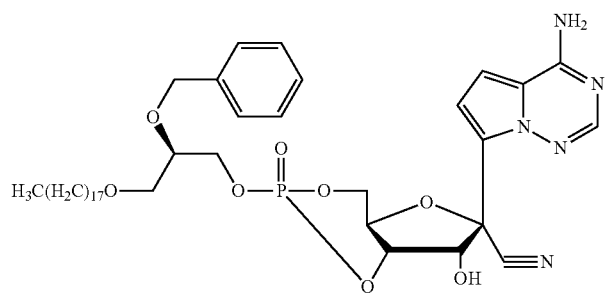
GS-441524-3′,5′-cyclic monophosphate, 1-O-octadecyl-2-O-benzyl-sn-glyceryl Ester When used herein with regard to the selection of a substituent, the term "independently" indicates that (i) a substituent at a particular location may be the same or different for each molecule of a formula (e.g., (i) a compound of formula (I) may include two molecules of formula (I), with each molecule having the same or a different $C_1$-$C_{30}$ hydrocarbyl selected for R; and/or (ii) two differently labeled substituents selected from the same pool of substituents may be the same or different (e.g., R and Y of a molecule of a compound of formula (I) may both be selected from "a $C_1$-$C_{30}$ hydrocarbyl", and the $C_1$-$C_{30}$ hydrocarbyls selected for R and Y may be the same or different)).

The phrases "$C_1$-$C_{30}$ hydrocarbyl," "$C_{10}$-$C_{30}$ hydrocarbyl", and the like, as used herein, generally refer to aliphatic, aryl, or arylalkyl groups containing 1 to 30 carbon atoms, or 10 to 30 carbon atoms, respectively, including substituted derivatives thereof, which, as explained herein, may include, but are not limited to, heteroaryl, heteroarylalkyl, heterocycloalkyl groups, etc. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and/or linear analogs or derivatives thereof, in each instance having 1 to 30 total carbon atoms or 10 to 30 total carbon atoms for a "$C_1$-$C_{30}$ hydrocarbyl" and "$C_{10}$-$C_{30}$ hydrocarbyl", respectively. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl, including any heteroatom substituted derivative thereof. Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl. Examples of aryl or arylalkyl moieties include, but are not limited to, anthracenyl, azulenyl, biphenyl, fluorenyl, indan, indenyl, naphthyl, phenanthrenyl, phenyl, 1,2,3,4-tetrahydro-naphthalene, anthracenyl, tolyl, xylyl, mesityl, benzyl, and the like, including any heteroatom substituted derivative thereof.

Unless otherwise indicated, the term "substituted," when used to describe a chemical structure or moiety, refers to a derivative of that structure or moiety wherein (i) a multivalent non-carbon atom (e.g., oxygen, nitrogen, sulfur, phosphorus, etc.) is bonded to one or more carbon atoms of the chemical structure or moiety (e.g., a "substituted" $C_4$ hydrocarbyl may include, but is not limited to, a pyrimidinyl moiety, a pyridinyl moiety, a dioxanyl moiety, a diethyl ether moiety, a methyl propionate moiety, an N,N-dimethylacetamide moiety, a butoxy moiety, etc., and a "substituted" aryl $C_{12}$ hydrocarbyl may include, but is not limited to, an oxydibenzene moiety, a benzophenone moiety, etc.) or (ii) one or more of its hydrogen atoms (e.g., chlorobenzene may be characterized generally as an aryl $C_6$ hydrocarbyl "substituted" with a chlorine atom) is substituted with a chemical moiety or functional group such as acyl, alcohol, alkoxy, alkanoyloxy, alkoxycarbonyl, alkenyl, alkyl (e.g., methyl, ethyl, propyl, t-butyl), alkynyl, alkylcarbonyloxy (—OC(O) alkyl), amide (—C(O)NH-alkyl- or -alkylNHC(O)alkyl), primary, secondary, and tertiary amino (such as alkylamino, arylamino, arylalkylamino), aryl, arylalkyl, aryloxy, azo, azido, carbamoyl (—NHC(O)O-alkyl- or —OC(O)NH-alkyl), carbamyl (e.g., $CONH_2$, as well as CONH-alkyl, CONH-aryl, and CONH-arylalkyl), carboxyl, carboxylic acid, cyano, cycloalkyl, cycloalkenyl, ester, ether (e.g., methoxy, ethoxy), halo, haloalkyl (e.g., —$CCl_3$, —$CF_3$, —$C(CF_3)_3$), haloalkoxy, trihalomethanesulfonyl, trihalomethanesulfonamido, heteroalkyl, heterocycloalkyl, heteroaryl, heteroarylalkyl, isocyanate, isothiocyanate, nitrile, nitro, oxo, phosphodiester, silyl, sulfide, sulfonamido (e.g., $SO_2NH_2$), sulfone, sulfenyl, sulfinyl, sulfonyl (including alkylsulfonyl, arylsulfonyl and arylalkylsulfonyl), sulfoxide, thiocarbonyl, thiocarbamyl, thiocyanato, thiol (e.g., sulfhydryl, thioether) or urea (—NHCONH-alkyl-).

Pharmaceutical Formulations

Also provided herein are pharmaceutical formulations. The pharmaceutical formulations may include a compound as described herein, such as a compound of formula (I). In some embodiments, the pharmaceutical formulation is orally bioavailable. In some embodiments, the pharmaceutical formulation is formulated for intramuscular injection.

The pharmaceutical formulations may include one compound described herein, or more than one (e.g., two, three, etc.) compounds described herein.

The pharmaceutical formulations may include any one or more pharmaceutically acceptable excipients.

Methods of Treatment

Also provided herein are methods of treatment, including methods of treating a virus infection, such as a coronavirus infection. The virus infection may be an infection in a mammal.

In some embodiments, the methods include administering to a mammal an effective amount of a compound described herein or a pharmaceutical formulation described herein.

The virus infection may be an RNA virus infection. In some embodiments, the RNA virus infection is caused by a RNA virus of a viral family selected from the group consisting of Filoviridae, Orthomyxoviridae, Paramyxoviridae, Pneumoviridae, Phenuiviridae, Nairoviridae, Arenaviridae, Flaviviridae, and Coronaviridae.

Compounds, including prodrugs, provided herein may be screened for inhibitory activity against SARS-CoV-2 and related coronaviruses (or other viruses), using conventional techniques for evaluating anti-coronavirus activity and cytotoxicity. Typically, compounds are first screened for inhibition of coronavirus in vitro, and those showing significant antiviral activity are then screened for efficacy in vivo.

Non-limiting examples of potentially useful in vitro assays including the following: a) Using the OC43 betacoronavirus strain (ATCC 1558) in the human adenocarcinoma cell line, HCT-8 (ATCC CCL-244), or using coronavirus 229E in MRC-5 human lung fibroblasts. Endpoints can include semiquantitative RT-PCR and pfu as determined by triplicate serial dilution. b) The activity of compounds may be studied using laboratory and clinical isolates of SARS-CoV-2 in Vero E6 cells, Caco-2, Calu-3, HPSC human lung cells, or Huh7.5 cells. Initial SARS CoV-2 growth inhibition assays can quantify plaque reduction on Vero cells grown in 12 well plates using a commercial murine anti-SARS CoV-2 spike protein detection antibody (Item 40021-MM07, Sino-Biological.com). Virus can also be quantified in culture supernatants by serial dilution on Vero cell lawns and by RT-PCR. Laboratory strains that can be obtained, for example, from BEI Resources (Strains NR52281 and NR522282), and clinical strains that can be isolated from patients participating in clinical trials can be used. Cytotoxicity can be measured by commercially MTT or Cell Titer Glo. Compounds with the lowest 90% inhibitory concentrations and that require the highest concentrations to induce cellular cytotoxicity may be selected for further evaluation. Anti-coronavirus compounds may also be evaluated in a lung explant model for SARS CoV infection. To determine activity in primary cells from the organ most clinically impacted by the virus, candidate molecules with the highest therapeutic indices in Vero E6 cells can be advanced to studies in human lung explants.

Methods of Producing a Compound

Also provided herein are methods of producing a compound, such as a compound described herein, which may be a prodrug.

The compounds provided herein may be prepared by a variety of processes, including the processes described herein. In some embodiments, protected analogs of remdesivir nucleoside, RVn, 2 are prepared and then coupled to suitable alkoxyalkyl phosphates to form phosphodiesters. Removal of the protecting groups can afford compounds of Formula (I).

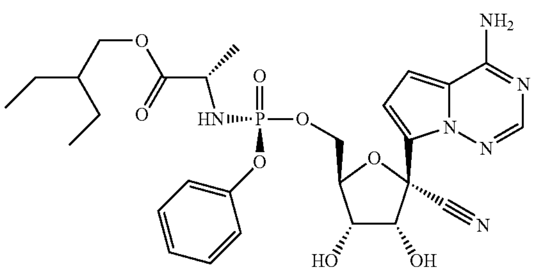

remdesivir, RDV, 1 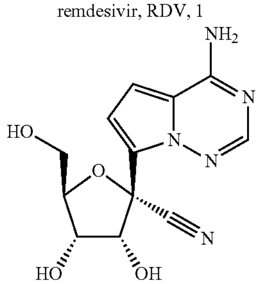 remdesivir nucleoside, RVn, 2

In some embodiments, 2-C-(4-aminopyrrolo[2,1-f][1,2,4]triazin-7-yl)-2,5-anhydro-D-altrononitrile (RVn, 2) is first converted to its 2', 3'-isopropylidene derivative. Mixtures of alkoxyalkyl phosphates and protected RVn may then be treated with N,N-dicyclohexylcarbodiimide (DCC) and N,N-dimethylaminopyridine (DMAP) under conditions suitable to prepare the phosphodiesters. Removal of the isopropylidene protecting group by treatment with dilute HCl or other suitable acid may provide compounds of Formula (I) in suitable yield and purity.

In some embodiments, the methods include providing a compound of formula (a)— formula (a)

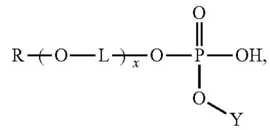

wherein x, R, L, and Y are as defined herein.

In some embodiments, the methods include providing a compound of formula (b)— formula (b)

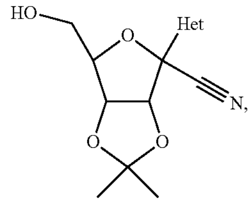

wherein Het is as defined herein. In some embodiments, Het is selected from the group consisting of—

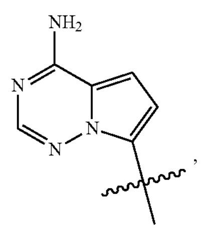

, 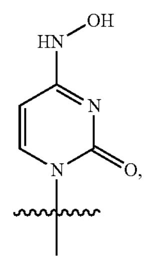 and

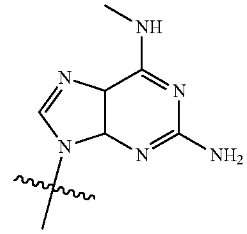

Also, as explained herein, formula (b) does not include any stereochemical indication(s), and therefore, reads on at least the following stereoisomer of formula (b):

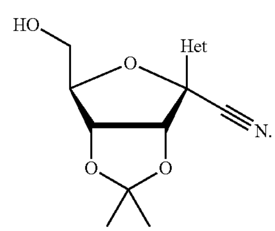

In some embodiments, the methods include contacting a compound of formula (a) and a compound of formula (b) to form a compound of formula (c)—

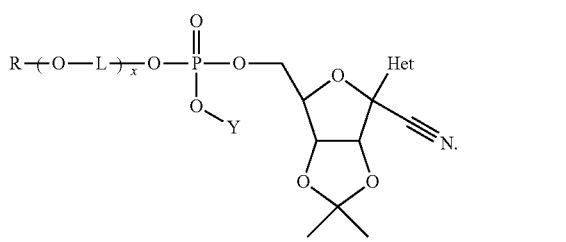

formula (c)

The contacting of a compound of formula (a) and a compound of formula (b) may occur at any temperature or pressure, and may occur in the presence of any suitable liquid. The liquid may include a $C_1$-$C_{30}$ hydrocarbyl, such as a $C_1$-$C_{30}$ hydrocarbyl that includes at least one cyclic moiety, at least one heteroatom, such as nitrogen, or a combination thereof. In some embodiments, the liquid is N,N-dicyclohexylcarbodiimide, 4-dimethylaminopyridine, or a combination thereof.

In some embodiments, the methods contacting a compound of formula (c) with an acid to form a compound of formula (d)—

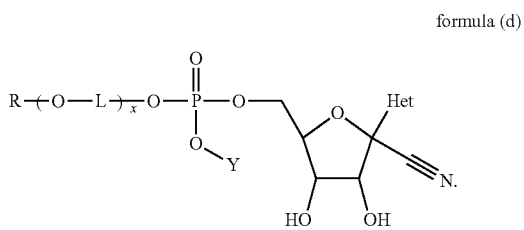

formula (d)

The acid may include any acid that is capable of facilitating the formation of a compound of formula (d). The acid may be an organic acid or inorganic acid. The acid may include a hydrogen halide, such as hydrogen chloride. The contacting of a compound of formula (c) with an acid may occur in the presence of any suitable liquid. The liquid may be a $C_1$-$C_{30}$ hydrocarbyl, such as a $C_1$-$C_{30}$ hydrocarbyl including at least one cyclic moiety, at least one heteroatom, or a combination thereof. In some embodiments, the liquid is tetrahydrofuran.

In some embodiments, the methods include performing an intramolecular esterification reaction of a compound of formula (d) to form a cyclic phosphate, such as a 3',5'-cyclic phosphate.

Methods of Producing a Drug Triphosphate

Also provided herein are methods of producing a drug triphosphate. In some embodiments, the methods include providing a plurality of cells, contacting the plurality of cells with an amount of a drug, incubating the plurality of cells and the amount of the drug for period effective to form the drug triphosphate. The plurality of cells may include any suitable cells. The plurality of cells, in some embodiments, includes Vero E6 cells, Calu-2 cells, Caco-2 cells, MRC5 human lung fibroblasts, Huh7.5 cells and PSC human lung cells. In some embodiments, the drug includes remdesivir or the remdesivir nucleoside (GS441524).

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, $22^{th}$ ed., (Pharmaceutical Press and Philadelphia College of Pharmacy at University of the Sciences 2012).

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

The present disclosure may address one or more of the problems and deficiencies of known methods and processes. However, it is contemplated that various embodiments may prove useful in addressing other problems and deficiencies in a number of technical areas. Therefore, the present disclosure should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

As used herein, the terms "comprises," "comprising," "includes," "including," "has," "having," "contains", "containing," "characterized by," or any other variation thereof, are intended to encompass a non-exclusive inclusion, subject to any limitation explicitly indicated otherwise, of the recited components. For example, a fusion protein, a pharmaceutical composition, and/or a method that "comprises" a list of elements (e.g., components, features, or steps) is not necessarily limited to only those elements (or components or steps), but may include other elements (or components or steps) not expressly listed or inherent to the fusion protein, pharmaceutical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a fusion protein, pharmaceutical composition, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

It is understood that aspects and embodiments of the invention described herein include "consisting" and/or "consisting essentially of" aspects and embodiments.

The terms "a," "an," and "the" are intended to include plural alternatives, e.g., at least one. For instance, the disclosure of "a compound", "a pharmaceutical formulation", "an acid", and the like, is meant to encompass one, or mixtures or combinations of more than one compound, pharmaceutical formulation, acid, and the like, unless otherwise specified.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in some embodiments, that "a is 15 to 25". This range should be interpreted as encompassing 15 and 25, and further encompasses each of 16, 17, 18, 19, 20, 21, 22, 23, and 24, including any ranges and sub-ranges between any of these values.

When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein the term "pharmaceutical composition" refers to pharmaceutically acceptable compositions, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective amount" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount in reference to diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent. As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human. The terms "subject" and "patient" are used interchangeably herein in reference, for example, to a mammalian subject, such as a human.

As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

"Nucleic acid" or "nucleic acid molecule" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid backbone can be made up of a variety of linkages, including one or more of sugar-phosphodiester linkages, peptide-nucleic acid bonds, phosphorothioate linkages, methylphosphonate linkages, or combinations thereof. Sugar moieties of the nucleic acid can be ribose, deoxyribose, or similar compounds having known substitutions (e.g. 2'-methoxy substitutions and 2'-halide substitutions). Nitrogenous bases can be conventional bases (A, G, C, T, U) or analogs thereof (e.g., inosine, 5-methylisocytosine, isoguanine). A nucleic acid can comprise only conventional sugars, bases, and linkages as found in RNA and DNA, or can include conventional components and substitutions (e.g., conventional bases linked by a 2'-methoxy backbone, or a nucleic acid including a mixture of conventional bases and one or more base analogs). Nucleic acids can include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA). Nucleic acids can include modified bases to alter the function or behavior of the nucleic acid (e.g., addition of a 3'-terminal dideoxynucleotide to block additional nucleotides from being added to the nucleic acid). Synthetic methods for making nucleic acids in vitro are well known in the art although nucleic acids can be purified from natural sources using routine techniques. Nucleic acids can be single-stranded or double-stranded.

A nucleic acid is typically single-stranded or double-stranded and will generally contain phosphodiester bonds, although in some cases, as outlined, herein, nucleic acid analogs are included that may have alternate backbones, including, for example and without limitation, phosphoramide (Beaucage et al. (1993) Tetrahedron 49(10):1925 and references therein; Letsinger (1970) J. Org. Chem. 35:3800; Sprinzl et al. (1977) Eur. J. Biochem. 81:579; Letsinger et al. (1986) Nucl. Acids Res. 14: 3487; Sawai et al. (1984) Chem. Lett. 805; Letsinger et al. (1988) J. Am. Chem. Soc. 110: 4470; and Pauwels et al. (1986) Chemica Scripta 26: 1419, which are each incorporated by reference), phosphorothioate (Mag et al. (1991) Nucleic Acids Res. 19:1437; and U.S. Pat. No. 5,644,048, which are both incorporated by reference), phosphorodithioate (Briu et al. (1989) J. Am. Chem. Soc. 111:2321, which is incorporated by reference), O-methylphosphoroamidite linkages (see Eckstein, Oligonucleotides and Analogues: A Practical Approach, Oxford University Press (1992), which is incorporated by reference), and peptide nucleic acid backbones and linkages (see, Egholm (1992) J. Am. Chem. Soc. 114:1895; Meier et al. (1992) Chem. Int. Ed. Engl. 31:1008; Nielsen (1993) Nature 365:566; and Carlsson et al. (1996) Nature 380:207, which are each incorporated by reference). Other analog nucleic acids include those with positively charged backbones (Denpcy et al. (1995) Proc. Natl. Acad. Sci. USA 92:6097, which is incorporated by reference); non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghvi and P. Dan Cook; Mesmaeker et al. (1994) Bioorganic & Medicinal Chem: Lett. 4: 395; Jeffs et al. (1994) J. Biomolecular NMR 34:17; and Tetrahedron Lett. 37:743 (1996), which are each incorporated by reference) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (see Jenkins et al. (1995) Chem. Soc. Rev. pp 169-176, which is incorporated by reference). Several nucleic acid analogs are also described in, e.g., Rawls, C & E News Jun. 2, 1997 page 35, which is incorporated by reference. These modifications of the ribose-phosphate backbone may be done to facilitate the addition of additional moieties such as labels, or to alter the stability and half-life of such molecules in physiological environments.

In addition to these naturally occurring heterocyclic bases that are typically found in nucleic acids (e.g., adenine, guanine, thymine, cytosine, and uracil), nucleic acid analogs also include those having non-naturally occurring heterocyclic or modified bases, many of which are described, or otherwise referred to, herein. In particular, many non-naturally occurring bases are described further in, e.g., Seela et al. (1991) Helv. Chim. Acta 74:1790, Grein et al. (1994) Bioorg. Med. Chem. Lett. 4:971-976, and Seela et al. (1999) Helv. Chim. Acta 82:1640, which are each incorporated by reference. To further illustrate, certain bases used in nucleotides that act as melting temperature (TO modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

Examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

An "oligonucleotide" or "oligomer" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth. Enzymol. 68:90-99; the phosphodiester method of Brown et al. (1979) Meth. Enzymol. 68:109-151; the diethylphosphoramidite method of Beaucage et al. (1981) Tetrahedron Lett. 22:1859-1862; the triester method of Matteucci et al. (1981) J. Am. Chem. Soc. 103:3185-3191; automated synthesis methods; or the solid support method of U.S. Pat. No. 4,458,066, or other methods known in the art. All of these references are incorporated by reference.

Compounds of the invention and methods of use for inhibiting RNA viruses include the following viral families: Filoviridae, Orthomyxoviridae, Paramyxoviridae, Pneumoviridae, Phenuiviridae, Nairoviridae, Arenaviridae, Flaviviridae and Coronaviridae. The names of exemplary viruses in each family are included in the below table.

| Virus Family | Virus |
| --- | --- |
| Filoviridae | Ebola virus |
|  | Sudan virus |
|  | Bundibugyo virus |
|  | Bombali virus |
|  | Reston virus |
|  | Marburg virus |
|  | Ravn virus |
| Orthomyxoviridae | Influenza viruses |
| Paramyxoviridae | Nipah virus |
|  | Hendra virus |
|  | Human Parainfluenza viruses |
|  | Measles virus |
|  | Mumps virus |
|  | Sosuga virus |
| Pneumoviridae | Respiratory syncytial viruses |
|  | Human metapneumovirus |
| Phenuiviridae | Rift Valley Fever virus |
|  | Punta Toro phlebovirus |
| Nairoviridae | Crimean Congo Hemorrhagic Fever virus |
|  | Dugbe virus |
| Arenaviridae | Lassa virus |
|  | Junin virus |
|  | Lymphocytic choriomeningitis virus |
|  | Guanarito virus |
|  | Machupo virus |
| Flaviviridae | Kyasanur Forest Disease virus |
|  | Omsk Hemorrhagic Fever virus |
|  | Yellow Fever virus |
|  | Japanese Encephalitis virus |
|  | Hepatitis C Virus |
|  | Zika Virus |
|  | Dengue Viruses |
|  | West Nile Virus |
|  | Tick Borne encephalitis virus |
|  | Murray Valley Fever encephalitis Virus |

33
-continued

| Virus Family | Virus |
|---|---|
| | Kunjin Virus |
| | Saint Louis Encephalitis Virus |
| | Bovine viral diarrhea virus |
| Coronaviridae | SARS-CoV-2 |
| | MERS |
| | SARS CoV |
| | OC43 |
| | 229E |
| | NL43 |
| | Evolving Zoonotic and Human Coronaviruses |
| | Feline Infectious Peritonitis virus |

EMBODIMENTS

Embodiments of the compounds, pharmaceutical formulations, and methods described herein are provided at the following listing:

Embodiment 1. A compound of formula (I):

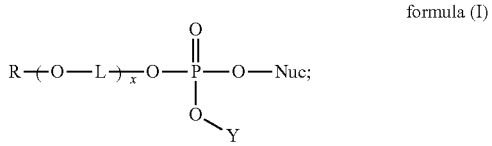

formula (I)

wherein Nuc is selected from the group consisting of an antiviral nucleoside and an antiviral nucleoside analog; Y is independently selected from the group consisting of hydrogen, a $C_1$-$C_{30}$ hydrocarbyl, a pharmaceutically acceptable cation, and a covalent bond to a carbon atom of a five-carbon sugar moiety of the antiviral nucleoside or the antiviral nucleoside analog; x is 0 or 1; L is a $C_1$-$C_6$ hydrocarbyl; and R is independently selected from the group consisting of a $C_{10}$-$C_{30}$ hydrocarbyl and a substituent of formula (A);

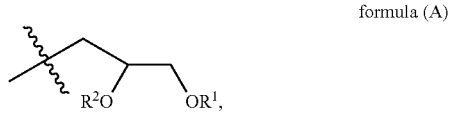

formula (A)

wherein $R^1$ and $R^2$ are independently selected from the group consisting of hydrogen and a $C_1$-$C_{30}$ hydrocarbyl.

Embodiment 2. The compound of Embodiment 1, wherein the antiviral nucleoside or the antiviral nucleoside analog is an antiviral ribonucleoside or an antiviral ribonucleoside analog, respectively.

Embodiment 3. The compound of any one of the previous Embodiments, wherein Nuc is selected from the group consisting of GS-441524, beta-D-N4-hydroxycytidine (NHC), and (2'R)-2-amino-2'-deoxy-2'-fluoro-N,2'-dimethyladenosine.

34

Embodiment 4. The compound of any one of the previous Embodiments, wherein Nuc is GS-441524:

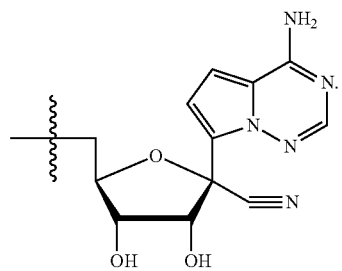

Embodiment 5. The compound of any one of the previous Embodiments, wherein Y is an unsubstituted $C_1$-$C_6$ alkyl, a $C_1$-$C_{20}$ hydrocarbyl, a $C_1$-$C_{10}$ hydrocarbyl, a $C_1$-$C_6$ hydrocarbyl, or $Na^+$.

Embodiment 6. The compound of any one of the previous Embodiments, wherein Y comprises at least one cyclic moiety.

Embodiment 7. The compound of any one of the previous Embodiments, wherein Y is selected from the group consisting of aryl, arylalkyl, heteroaryl, heteroarylakyl, and heterocycloalkyl, each of which is unsubstituted or substituted.

Embodiment 8. The compound of any one of the previous Embodiments, wherein the heteroaryl is an unsubstituted or substituted pyridinyl.

Embodiment 9. The compound of any one of the previous Embodiments, wherein the arylalkyl is an unsubstituted or substituted benzyl.

Embodiment 10. The compound of any one of the previous Embodiments, wherein the unsubstituted or substituted benzyl has a structure according to formula (B):

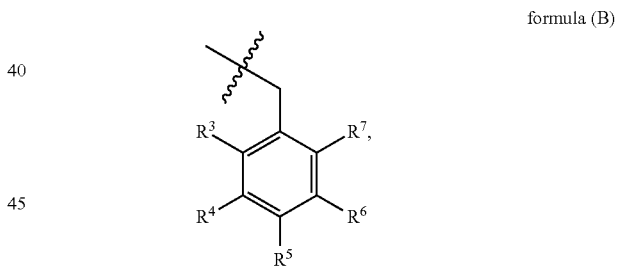

formula (B)

wherein $R^3$, $R^4$, $R^5$, $R^6$, and $R^7$ are independently selected from the group consisting of hydrogen, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino, and di-substituted amino.

Embodiment 11. The compound of any one of the previous Embodiments, wherein at least two of $R^3$, $R^4$, $R^5$, $R^6$, and $R^7$ are hydrogen.

Embodiment 12. The compound of any one of the previous Embodiments, wherein R (i) is an unsubstituted or substituted $C_{12}$-$C_{24}$ hydrocarbyl, (ii) comprises 0 to 6 unsaturated bonds, (iii) comprises a cyclopropyl moiety, or (iv) a combination thereof.

Embodiment 13. The compound of any one of the previous Embodiments, wherein R (i) is an unsubstituted or substituted $C_{13}$-$C_{29}$ heteroalkyl, (ii) comprises 0 to 6 unsaturated bonds, or (iii) a combination thereof.

Embodiment 14. The compound of any one of the previous Embodiments, wherein R is selected from the group consisting of—

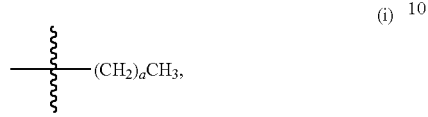

(i)

wherein a is 1 to 29; and

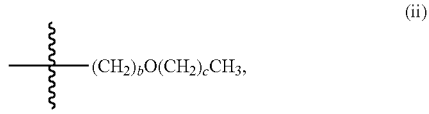

(ii)

wherein b is 1 to 29, c is 0 to 28, and a sum of b and c is 29 or less.

Embodiment 15. The compound of any one of the previous Embodiments, wherein (i) a is 15 to 25, or (ii) b is 1 to 4 and c is 15 to 20.

Embodiment 16. The compound of any one of the previous Embodiments, wherein (i) a is 19, (ii) b is 3 and c is 15, or (iii) b is 2 and c is 17.

Embodiment 17. The compound of any one of the previous Embodiments, wherein a is 8.

Embodiment 18. The compound of any one of the previous Embodiments, wherein $R^1$ (i) is an unsubstituted or substituted $C_{12}$-$C_{24}$ hydrocarbyl, (ii) comprises 0 to 6 unsaturated bonds, or (iii) a combination thereof.

Embodiment 19. The compound of any one of the previous Embodiments, wherein (i) $R^1$, (ii) $R^2$, or (iii) both $R^1$ and $R^2$ are independently selected from a $C_1$-$C_{30}$ hydrocarbyl comprising at least one cyclic moiety.

Embodiment 20. The compound of any one of the previous Embodiments, wherein (i) $R^1$, (ii) $R^2$, or (iii) both $R^1$ and $R^2$ are independently selected from the group consisting of aryl, arylalkyl, heteroaryl, heteroarylakyl, and heterocycloalkyl, each of which is unsubstituted or substituted.

Embodiment 21. The compound of any one of the previous Embodiments, wherein the arylalkyl is an unsubstituted or substituted benzyl.

Embodiment 22. The compound of any one of the previous Embodiments, wherein the unsubstituted or substituted benzyl has a structure according to formula (C):

formula (C)

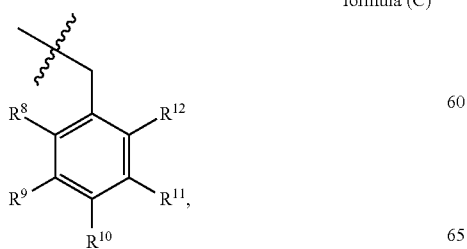

wherein $R^8$, $R^9$, $R^{10}$, $R^{11}$, and $R^{12}$ are independently selected from the group consisting of hydrogen, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino, and di-substituted amino.

Embodiment 23. The compound of any one of the previous Embodiments, wherein at least two of $R^8$, $R^9$, $R^{10}$, $R^{11}$, and $R^{12}$ are hydrogen.

Embodiment 24. The compound of any one of the previous Embodiments, wherein the substituent of formula (A) is a racemate, an sn-1 stereoisomer, or an sn-3 stereoisomer.

Embodiment 25. The compound of any one of the previous Embodiments, wherein—

(i) $R^1$ is selected from the group consisting of—

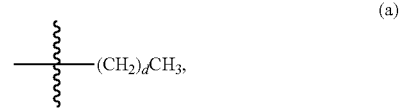

(a)

wherein d is 1 to 29; and

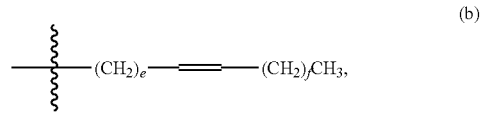

(b)

wherein e is 1 to 27, f is 0 to 26, and a sum of e and f is 27 or less;

(ii) $R^2$ is selected from the group consisting of—

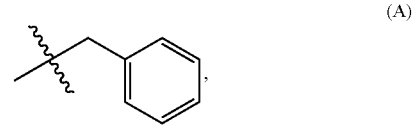

(A)

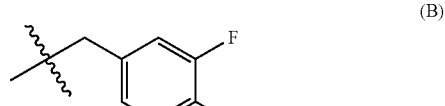

(B)

(C)

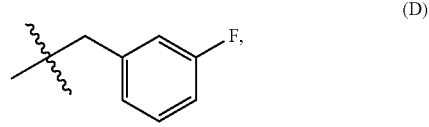

(D)

-continued

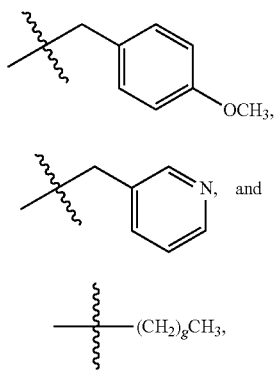

(E)

(F)

(G)

wherein g is 1 to 29; or
(iii) a combination thereof.

Embodiment 26. The compound of any one of the previous Embodiments, wherein g is 5 to 10.

Embodiment 27. The compound of any one of the previous Embodiments, wherein g is 7.

Embodiment 28. The compound of any one of the previous Embodiments, wherein x is 1, and L is an unsubstituted or substituted $C_1$-$C_3$ hydrocarbyl.

Embodiment 29. The compound of any one of the previous Embodiments, wherein L is selected from the group consisting of an unsubstituted methyl, an unsubstituted ethyl and an unsubstituted propyl.

Embodiment 30. A pharmaceutical formulation comprising the compound of any one of Embodiments 1 to 29.

Embodiment 31. The pharmaceutical formulation of Embodiment 30, wherein the pharmaceutical formulation is orally bioavailable.

Embodiment 32. The pharmaceutical formulation of Embodiment 30, wherein the pharmaceutical formulation is formulated for intramuscular injection.

Embodiment 33. A method for treating coronavirus infection in a mammal, the method comprising administering to the mammal an effective amount of the compound of any one of Embodiments 1 to 29, or the pharmaceutical formulation of any one of Embodiments 30 to 32.

Embodiment 34. A method for treating a virus infection in a mammal, the method comprising administering to the mammal an effective amount of a compound of the compound of any one of Embodiments 1 to 29, or the pharmaceutical formulation of any one of Embodiments 30 to 32, wherein the virus is a RNA virus of a viral family selected from the group consisting of Filoviridae, Orthomyxoviridae, Paramyxoviridae, Pneumoviridae, Phenuiviridae, Nairoviridae, Arenaviridae, Flaviviridae, and Coronaviridae.

Embodiment 35. A method for producing a prodrug, the method comprising:
(i) providing a compound of formula (a)—

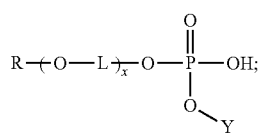

formula (a)

(ii) providing a compound of formula (b)—

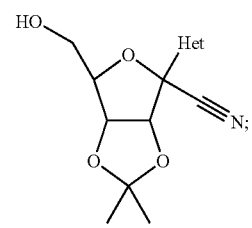

formula (b)

(iii) contacting the compound of formula (a) and the compound of formula (b) to form a compound of formula (c)—

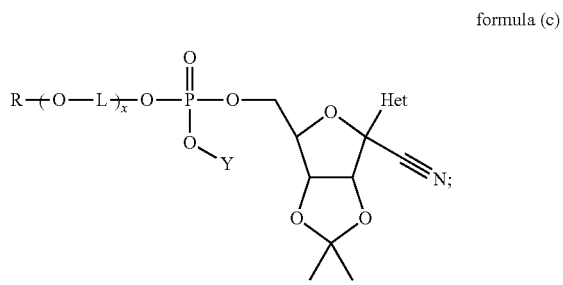

formula (c)

and
(iv) contacting the compound of formula (c) with an acid to form a compound of formula (d)—

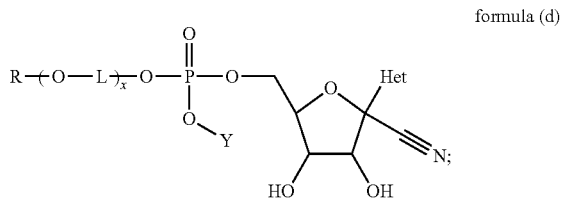

formula (d)

wherein Het is a $C_1$-$C_{30}$ hydrocarbyl comprising at least one heteroatom; Y is selected from the group consisting of hydrogen, a $C_1$-$C_{30}$ hydrocarbyl, and a pharmaceutically acceptable cation; x is 0 or 1; L is a $C_1$-$C_6$ hydrocarbyl; and R is selected from the group consisting of a $C_{10}$-$C_{30}$ hydrocarbyl and a substituent of formula (A);

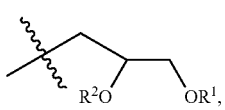

formula (A)

wherein $R^1$ and $R^2$ are independently selected from the group consisting of hydrogen and a $C_1$-$C_{30}$ hydrocarbyl.

Embodiment 36. The method for producing a prodrug of any of the previous Embodiments, wherein the contacting of the compound of formula (a) and the compound of formula (b) occurs in the presence of N,N-dicyclohexylcarbodiimide, 4-dimethylaminopyridine, or a combination thereof.

Embodiment 37. The method for producing a prodrug of any of the previous Embodiments, wherein the acid comprises HCl.

Embodiment 38. The method for producing a prodrug of any of the previous Embodiments, wherein the contacting of formula (c) with the acid occurs in the presence of tetrahydrofuran (THF).

Embodiment 39. The method for producing a prodrug of any of the previous Embodiments, wherein Het is selected from the group consisting of—

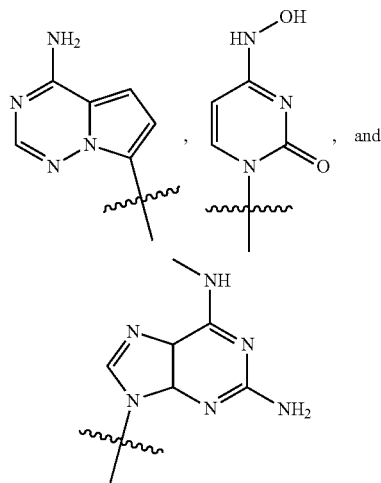

Embodiment 40. The method for producing a prodrug of any of the previous Embodiments, further comprising performing an intramolecular esterification reaction of a compound of formula (d) to form a cyclic phosphate, such as a 3',5'-cyclic phosphate.

Embodiment 41. A method of producing a drug triphosphate, the method comprising providing a plurality of cells, contacting the plurality of cells with an amount of a drug, incubating the plurality of cells and the amount of the drug for period effective to form the drug triphosphate.

Embodiment 42. The method of Embodiment 41, wherein the plurality of cells comprises Vero E6 cells.

Embodiment 43. The method of Embodiment 41 or 42, wherein the drug comprises remdesivir.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—Preparation of Compounds

In this example, several general methods were used for producing various products and/or intermediates, but other known synthesis techniques may be used.

A. Synthesis of Alkyl and Alkoxyalkyl Esters of GS-441524 5'-monophosphate

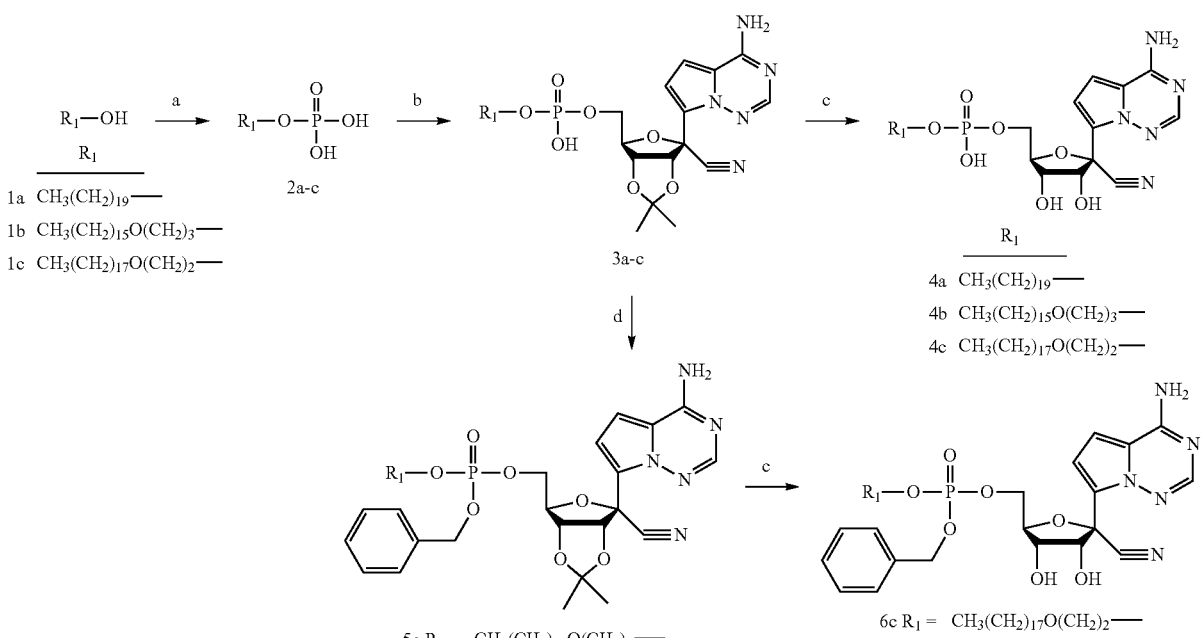

Scheme 1. Synthesis of Alkyl and Alkoxyalkyl Esters of GS-441524 5'-Monophosphate.

Reagents: a) $POCl_3$, TEA, THF; b) GS-441524 acetonide, DCC/DMAP or DIC/NMI, pyridine; c) formic acid, rt or con. HCl/THF; d) PyBOP, DIEA, DMF Synthesis of Alkyl and Alkoxyalkyl Phosphates
(Scheme 1, 2a-c)

General Method A.

Long-chain alcohols 1a-c were phosphorylated to afford phosphates 2a-c as previously described (Ruiz, J., Beadle, J. R., Aldern, K. A., Keith, K., Hartline, C., Kern, E., Hostetler, K. Y. (2007). Synthesis and antiviral evaluation of alkoxy-alkyl-phosphate conjugates of cidofovir and adefovir. *Antiviral Res.*, 75, 87-90). Briefly, a solution of the long-chain alcohol (1 eq.) and triethylamine (2 eq.) in anhydrous tetrahydrofuran (THF) was added dropwise to a solution of phosphorus oxychloride (1.5 eq.) in THF with stirring while the temperature was maintained below 20° C. Stirring was continued for an additional hour at 0° C., then water was added and the stirring continued overnight followed by extraction with ethyl ether. The crude solid from the ether layer was recrystallized from hexanes to afford phosphates 2a-c.

2a Eicosyl dihydrogen phosphate $^1$H NMR (400 MHz, Chloroform-d) δ 8.30 (s, 1H), 3.98 (t, 2H), 1.61 (m, 1H), 1.26 (br s, 16H), 0.86 (t, 1H). ESI-MS 650.38 [M−H]$^-$ 2b 3-(Hexadecyloxy)propyl dihydrogen phosphate $^1$H NMR (400 MHz, Chloroform-d) δ 4.03 (dt, 2H), 3.49 (t, 2H), 3.40 (t, 2H), 1.94 (p, 2H), 1.59-1.55 (m, 2H), 1.26 (br s, 18H), 0.86 (t, 3H).

2c 2-(Octadecyloxy)ethyl dihydrogen phosphate $^1$H NMR (400 MHz, Chloroform-d) δ 4.12 (dt, 2H), 3.77 (t, 2H), 3.42 (t, 2H), 1.29 (br s, 20H), 0.94-0.85 (t, 3H).

Coupling of Phosphates 2a-c to GS-441524 Acetonide (Remdesivir Nucleoside, RVn Acetonide General Method B.

N,N-Dicyclohexylcarbodiimide (DCC, 1.5 eq) was added to a mixture of GS-441524 acetonide (1 eq, CAS #1191237-80-5, purchased from Ontario Chemicals), a long-chain dihydrogen phosphate (1.0 eq), and 4-dimethylaminopyridine (DMAP, 1.0 eq) in dry pyridine, and then the mixture was heated to 90° C. and stirred for 24 h. Water was added to quench the reaction and pyridine was evaporated under vacuum. The residue was adsorbed onto silica gel and purified by flash column chromatography on silica gel 60. Gradient elution (CH$_2$Cl$_2$/methanol 10-20%) afforded the protected phosphodiester compound.

General Method C.

N,N-Diisopropylcarbodiimide (DIC, 3.3 mmol) was added to a mixture of GS-441524 acetonide (1.65 mmol), lipid phosphate (1.65 mmol), and 1-methylimidazole (NMI, 406 mg, 4.95 mmol) in dry pyridine (30 mL), and then the mixture was stirred for 48 h at room temperature until analysis of the reaction mixture by TLC indicated substantial formation of coupled product Water (5 mL) was then added, and the mixture was concentrated on a rotary evaporator. The residue was adsorbed onto silica gel and purified by flash column chromatography on silica gel 60. Gradient elution (100% CH$_2$Cl$_2$ to CH$_2$Cl$_2$/20% methanol) afforded the protected phosphodiester analogs.

3a Eicosyl-phospho-RVn acetonide. GS-441524 acetonide was coupled to 2a according to General Method C. Structure was confirmed by ESI-MS 690.50 [M−H]$^-$.

3b 3-(Hexadecyloxy)propyl-phospho-RVn acetonide. GS-441524 acetonide was coupled to 2b according to General Method B. N,N-Dicyclohexylcarbodiimide (DCC, 619 mg, 3 mmol) was added to a mixture of GS-441524 acetonide (300 mg, 0.91 mmol), 3-(hexadecyloxy)propyl phosphate (2b, 414 mg, 1.10 mmol), and 4-dimethylamino-pyridine (DMAP, 122 mg, 1.0 mmol) in 25 mL of dry pyridine, and then the mixture was heated to 90° C. and stirred for 24 h. Pyridine was then evaporated and the residue was purified by flash column chromatography on silica gel 60. Gradient elution (CH$_2$Cl$_2$/methanol 10-20%) afforded 423 mg (67% yield) of Compound 3b. $^1$H NMR (500 MHz, chloroform-d) δ 8.42 (s, 1H), 7.98 (s, 1H), 7.70 (s, 2H), 6.22 (d, J=6.0 Hz, 1H), 5.68 (d, J=6.2 Hz, 1H), 5.15 (d, J=1.0 Hz, 1H), 4.70 (dd, J=3.8, 0.9 Hz, 1H), 4.48-4.42 (m, 1H), 4.26 (ddd, J=11.2, 8.5, 2.6 Hz, 1H), 4.15 (ddd, J=11.1, 8.5, 2.6 Hz, 1H), 4.02 (dt, J=8.5, 6.3 Hz, 2H), 3.49 (t, J=6.1 Hz, 2H), 3.40 (t, J=6.1 Hz, 2H), 1.95 (p, J=6.2 Hz, 2H), 1.54 (tt, J=7.4, 6.1 Hz, 2H), 1.31 (s, 3H), 1.32-1.24 (m, 26H), 0.94-0.85 (m, 3H). ESI-MS 691.6 [M−H]$^-$.

3c 2-(Octadecyloxy)ethyl-phospho-RVn acetonide. GS-441524 acetonide was coupled to 2c according to General Method B. N,N-Dicyclohexylcarbodiimide (DCC, 0.3 g, 1.4 mmol) was added to a mixture of GS-441524 acetonide (0.23 g, 0.7 mmol), phosphate 2c (0.27 g, 0.68 mmol), and 4-dimethylaminopyridine (DMAP, 0.07 g, 0.6 mmol) in 10 mL of dry pyridine, and then the mixture was heated to 90° C. and stirred for 3 days. Pyridine was then evaporated, and the residue was purified by flash column chromatography on silica gel 60. Gradient elution (CH$_2$Cl$_2$/methanol 10-20%) afforded 0.22 g (45% yield) of phosphodiester 3c.

Synthesis of 4a-c: Removal of the Acetonide Protecting Group

General Method D. (HCl/THF)

Concentrated HCl (0.1 mL) in tetrahydrofuran (THF, 1 mL) was added to a stirred solution of acetonide-protected (2′,3′-isopropylidene) phosphodiesters (0.25 mmol) in THF (10 mL) at room temperature. The mixture was stirred for 3 h and then sodium bicarbonate (50 mg) and water (2 mL) were added. After stirring an additional 15 min. the solvents were evaporated and cold water (10 mL) was added to the residue. The crude product was collected by vacuum filtration and dried under vacuum. Purification by flash column chromatography (100% CH$_2$Cl$_2$ to CH$_2$Cl$_2$/35% methanol) yielded pure phosphodiester analogs.

General Method E.

Acetonide analogs (1 mmol) were added to formic acid (25 mL) at room temperature and stirred. The reaction was monitored by TLC until deprotection was complete at about 4 h. Formic acid was removed by rotary evaporation and the residue was co-evaporated with EtOH (2×25 mL), then adsorbed onto silica gel and purified by flash column chromatography. Gradient elution (100% CH$_2$Cl$_2$ to CH$_2$Cl$_2$/35% methanol) afforded products.

4a Eicosyl-phospho-RVn—Prepared from 3a according to General Method E. Structure was confirmed by ESI-MS 650.38 [M−H]$^-$.

4b 3-(Hexadecyloxy)propyl-phospho-RVn. Prepared from 3b according to General Method D. Concentrated HCl (0.1 mL) in tetrahydrofuran (THF, 1 mL) was added to a stirred solution of 3b (100 mg, 0.14 mmol) in THF (10 mL) at room temperature. The mixture was stirred for 3 h and then sodium bicarbonate (50 mg) and water (2 mL) were added. After stirring an additional 15 min. the solvents were evaporated and cold water (10 mL) was added to the residue. The solid product was collected by vacuum filtration and dried under vacuum to yield 4b (79 mg, 87% yield) as an off-white solid. $^1$H NMR (500 MHz, CDCl$_3$-methanol-d$_4$) δ 8.42 (s, 1H), 7.98 (s, 1H), 7.70 (s, 1H), 6.22 (d, J=6.0 Hz, 1H), 5.70 (d, J=6.0 Hz, 1H), 5.12 (d, J=4.2 Hz, 1H), 4.55 (ddd, J=5.5, 2.7, 0.9 Hz, 1H), 4.40 (dtd, J=6.8, 2.6, 0.8 Hz, 1H), 4.33-4.27 (m, 2H), 4.25 (ddd, J=11.1, 8.4, 2.6 Hz, 1H), 4.16 (ddd, J=11.3, 8.5, 2.6 Hz, 1H), 4.02 (dt, J=8.5, 6.3 Hz, 2H), 3.49 (t, J=6.1 Hz, 2H), 3.40 (t, J=6.1 Hz, 2H), 1.95 (p, J=6.2 Hz, 2H), 1.59-1.50 (m, 1H), 1.34-1.24 (m, 23H), 0.94-0.85 (m, 3H). ESI MS: 652.39 [M−H]$^-$. Purity by HPLC: 99.7%

4c 2-(Octadecyloxy)ethyl-phospho-RVn Prepared from 3c according to General Method D. Concentrated HCl (0.3 mL) was added slowly to a stirred solution of 3c (0.2 g, 0.28 mmol) in THF (10 mL) at 0° C. The mixture was allowed to warm to room temperature overnight and then was diluted with water (2 mL) and adjusted to pH=8 by adding saturated sodium bicarbonate. The product was extracted with chloroform (3×30 mL) and the organic layer was concentrated under reduced pressure. The residue was purified by flash chromatography on silica gel. Elution with 20% MeOH/CH$_2$Cl$_2$ gave 0.10 g (55% yield) of compound 4c. $^1$H NMR (400 MHz, CDCl$_3$-methanol-d$_4$) δ ppm 7.89 (s, 1H), 6.94 (d, J=4.65 Hz, 1H), 6.89 (d, J=4.65 Hz, 1H), 4.40 (d, J=4.65 Hz, 2H), 4.21-4.28 (m, 1H), 4.12-4.20 (m, 1H), 4.04-4.12 (m, 1H), 3.91 (d, J=4.89 Hz, 2H), 3.46-3.57 (m, 2H), 3.42 (td, J=6.85, 1.96 Hz, 2H), 3.34 (dt, J=3.18, 1.59 Hz, 2H), 1.53 (d, J=6.85 Hz, 2H), 1.20-1.37 (m, 30H), 0.89 (t, J=6.97 Hz, 3H). ESI MS: 666.43 [M−H]$^-$. Purity by HPLC 98.4%.

B. Synthesis of 2-(Octadecyloxy)ethyl benzyl phospho-RVn (Long-Acting Formulation) (Scheme 1, 6c)

Compound 3c (160 mg, 0.22 mmol), benzyl alcohol (48 mg, 0.45 mmol), diisopropylethylamine (DIEA, 58 mg, 0.45 mmol), and (1H-benzotriazol-1-yloxy)-tripyrrolidinophosphonium hexafluorophosphate (PyBOP, 230 mg, 0.45 mmol) in dry DMF (5 mL) were stirred at room temperature for 3 h. DMF was then evaporated, and the residue was dissolved in ethyl acetate (50 mL) and washed with saturated NaHCO$_3$ (3×10 mL). The organic layer was dried over MgSO$_4$ and concentrated. The residue was purified by column chromatography on silica gel, eluting with chloroform/methanol (0-15%) to yield 5c (60 mg, 35% yield). $^1$H NMR (400 MHz, CDCl$_3$-CD$_3$OD) δ ppm 7.87 (d, J=4.03 Hz, 1H), 7.27-7.37 (m, 5H), 6.91-6.95 (m, 1H), 6.83-6.89 (m, 1H), 5.41 (d, J=6.97 Hz, 1H), 4.92-5.06 (m, 3H), 4.54-4.60 (m, 1H), 4.24-4.31 (m, 2H), 4.07-4.15 (m, 2H), 3.53-3.69 (m, 2H), 3.38-3.51 (m, 2H), 3.32-3.37 (m, 2H), 1.78-1.96 (m, 2H), 1.75 (s, 3H), 1.50-1.60 (m, 2H), 1.42 (s, 3H), 1.15-1.38 (m, 30H), 0.89 (t, J=6.54 Hz, 3H). ESI MS: 798.51 [M+H]$^+$, 820.56 [M+Na]$^+$.

To a solution of 5c (60 mg, 0.075 mmol) in THF (2 mL), con. HCl (0.1 mL) was added at 0° C. After 20 min the ice bath was removed and the reaction was monitored by TLC. After 3 h the ice bath was returned and the mixture was neutralized with sat. NaHCO$_3$. The mixture was concentrated under vacuum and the residue was purified by column chromatography (silica gel, dichloromethane/methanol 10-20%) to give 35 mg (62% yield) of 6c. $^1$H NMR (400 MHz, CDCl$_3$+methanol d$_4$) δ ppm 7.84-7.90 (m, 1H), 7.29-7.38 (m, 5H), 6.89-6.93 (m, 1H), 6.82-6.86 (m, 1H), 5.03 (d, J=11.36 Hz, 2H), 4.76-4.81 (m, 1H), 4.40-4.45 (m, 1H), 4.30-4.37 (m, 1H), 4.17-4.31 (m, 2H), 4.06-4.14 (m, 2H), 3.54-3.60 (m, 2H), 3.39-3.47 (m, 2H), 3.33-3.37 (m, 2H), 3.12-3.18 (m, 2H), 1.82-1.91 (m, 2H), 1.49-1.59 (m, 2H), 1.20-1.37 (m, 30H), 0.89 (t, J=6.60 Hz, 3H). ESI MS: 758.32 [M+H]$^+$, 780.43 [M+Na]$^+$.

C. Synthesis of 1-O-alkyl-2-O-Substituted-sn-glyceryl Esters of GS-441524 5'-monophosphate The following scheme (Scheme 2) depicts embodiments of synthesis methods that were used to produce the following embodiments of 1-O-alkyl-2-O-substituted-sn-glyceryl esters of GS-441524 5'-monophosphate.

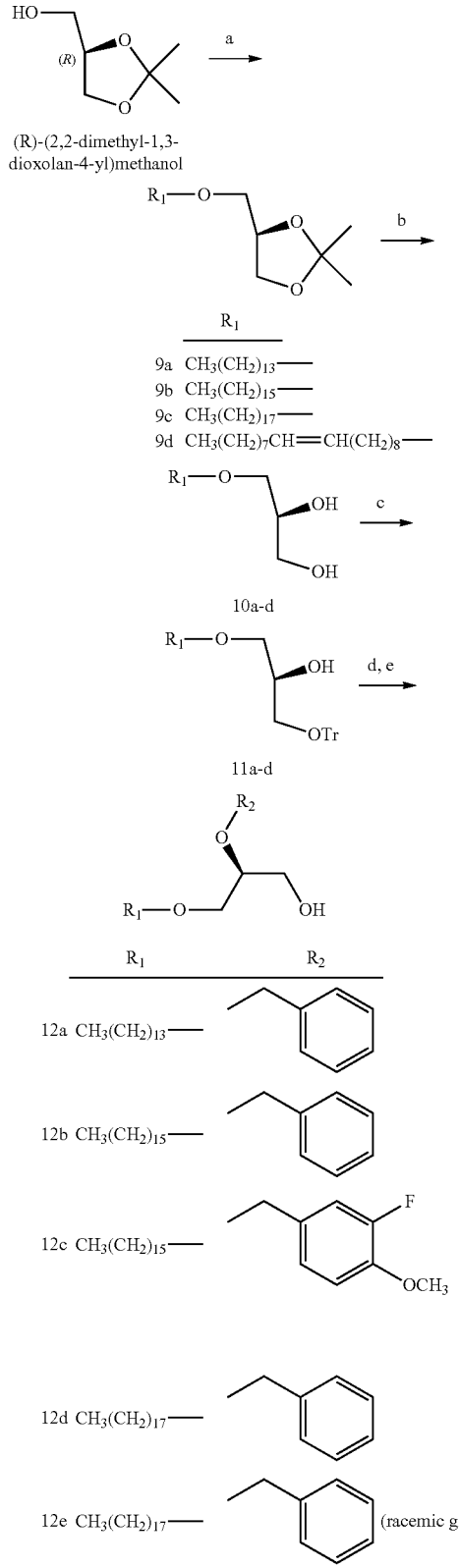

Scheme 2. Synthesis of 1-O-Alkyl-2-O-substituted-sn-glycerols.

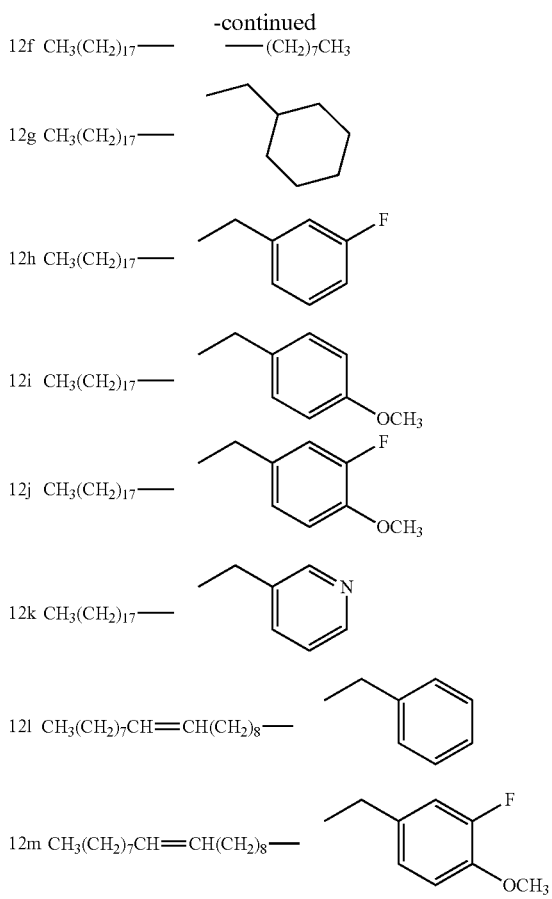

Reagents: a) R₁ bromides or methanesulfonates, NaH, DMF; b) 80% CH₃COOH, reflux; c) trityl chloride, TEA, DMAP, CH₂Cl₂; d) R₂ bromides or methanesulfonates, NaH, DMF e) acidic deprotection.

Synthesis of 1-O-Alkyl-sn-glycerols (Scheme 2, 10 a-d)

General Method F.

In this embodiment, alkylation of 2,3-isopropylideneglycerol using an alkylmethanesulfonate was performed as described in the literature (Fernández, D. M.; Contreras, L. J.; Moreno, B. M.; Silva, E. G.; Mayorga, H. W. Enantiomeric synthesis of natural alkylglycerols and their antibacterial and antibiofilm activities. Nat. Prod. Res. 2019, 1-7). Briefly, Sodium hydride and DMF stirred in a flask. Isopropylidene glycerol is added slowly (hydrogen evolution!), cooling if necessary to keep temp less than 35 C. Stirred additional 30 min. Alkyl methanesulfonate was added all at once and stirred vigorously 5 h. Reaction mix was poured onto crushed ice and stirred gently. Solid was collected on a frit funnel. Washed with water. Deprotection: Filter cake was added to 80% acetic acid and heated 80 C for 1 h. The flask was cooled and product crystallized collected vacuum filtration and dried. Crude product was recrystallized in hexanes or purified by flash column chromatography on silica gel 60.

General Method G. (Alkylation Using a 1-Bromoalkane/Alkene as Described in the Literature: (Halldorsson, A., et al. *Tetrahedron: Asymmetry*, 2004, 15, 2893-2899)).

Briefly, isopylideneglycerol (1 eq), 1-bromoalkane/alkene (1 eq) and tetrabutylammonium bromide (0.2 eq) were stirred vigorously in a round-bottomed flask. Ground potassium hydroxide (2 eq) was added slowly, and the mixture stirred for approx. 15 h at 35-40° C. in an oil bath. The alkylated product was extracted into hexanes and the organic phase was washed with $H_2O$, then evaporated to yield the 1-O-alkyl-2,3-isopropylidene-sn-glycerol. Deprotection: The products were refluxed overnight with p-toluenesulfonic acid (10 mol %) in THF/water. After concentration under vacuum, the residue was dissolved in diethyl ether, washed with water and brine solution, dried over anhydrous magnesium sulphate and solvent removal in vacuo on a rotary evaporator to afford the 1-O-alkyl-sn-glycerol.

10a. 1-O-Tetradecyl-sn-glycerol. Synthesized according to General Method F. Analytical data was consistent with literature values (Barragin, C. A.; Silva, E. G.; Moreno, B. M.; Mayorga, H. W. Inhibition of quorum sensing by compounds from two Eunicea species and synthetic saturated alkylglycerols. Vitae 2018, 25, 92-103.)

10b. 1-O-Hexadecyl-sn-glycerol was purchased from Bachem America 10c. 1-O-Octadecyl-sn-glycerol was purchased from Bachem America 10d. 1-O-Oleyl-sn-glycerol. Synthesized according to General Method G. A mixture of oleyl bromide (541 mg, 1.63 mmol), Bu₄NBr (0.2 eq), 2,3-isopropylidene-sn-glycerol (1 eq), and KOH (powder, 2.5 eq) was stirred at 40° C. overnight. Work up gave 583 mg crude 9d as an oil. Crude 9d was treated with p-TsOH·H₂O (0.15 eq.) in refluxing THF (6 mL) and H₂O (2.5 mL) overnight. Purification of the crude oil (540 mg) by flash column chromatography (MeOH in DCM 0-8%) afforded 420 mg 1-O-oleyl-sn-glycerol 10d as an oil. Yield 75% (two steps). ¹H NMR (CDCl₃) δ 5.36-5.33 (m, 2H), 3.86-3.85 (m, 1H), 3.72 (dd, 1H), 3.62 (dd, 1H), 3.52 (dd, 1H), 3.46 (dd, 1H), 3.50-3.42 (m, 2H), 2.02-1.99 (m, 4H), 1.59-1.55 (quintet, 2H), 1.35-1.26 (m, 22H), 0.88 (t, 3H) ESI-MS 343.67 [M+H]⁺, 365.61 [M+Na]⁺.

Synthesis of 1-O-Alkyl-2-O-substituted-sn-glycerols (Scheme 2, 12a-m)

General Method H.

Protection of the 3-hydroxy group of 1-O-substituted-sn-glycerols was carried out as described in the literature: (Kini, G. D., Hostetler, S. E., Beadle, J. R., Aldern, K. A. Synthesis and antiviral activity of 1-O-octadecyl-2-O-alkyl-sn-glycero-3-foscarnet conjugates in human cytomegalovirus-infected cells, *Antiviral Research*, 1997, 36, 115; and Huang, Z., Szoka, Z. (2008). Sterol-Modified Phospholipids: Cholesterol and Phospholipid Chimeras with Improved Biomembrane Properties. *J. Am. Chem. Soc.*, 130, 15702-15712). Briefly, triethylamine (1.5 eq) was added to a solution of 1-O-alkyl-sn-glycerol (1 eq), N,N-dimethylaminopyridine (DMAP, 0.1 eq), and triphenyl chloride (TrCl, 1.5 eq) in anhydrous dichloromethane, and the mixture was stirred 18 h. The reaction mixture was then quenched with water, evaporated and adsorbed onto silica gel and purified by flash column chromatography over silica gel. An increasing gradient of ethyl acetate in hexanes (0-20%) eluted the proper fractions.

11a 1-O-Tetradecyl-3-O-trityl-sn-glycerol—Prepared as described in the literature (Huang, Z., Szoka, Z. (2008). Sterol-Modified Phospholipids: Cholesterol and Phospholipid Chimeras with Improved Biomembrane Properties. *J. Am. Chem. Soc.*, 130, 15702-15712).

11b 1-O-Hexadecyl-3-O-trityl-sn-glycerol—Prepared as described in the literature (Huang, Z., Szoka, Z. (2008).

Sterol-Modified Phospholipids: Cholesterol and Phospholipid Chimeras with Improved Biomembrane Properties. *J. Am. Chem. Soc.,* 130, 15702-15712).

11c 1-O-octadecyl-3-O-trityl-sn-glycerol. Prepared from 10c according to General Method H. Yield 87%. $^1$H NMR (CDCl$_3$): δ 0.9 (t, 3H), 1.3 (bs, 30H), 1.55 (m, 4H) 3.2 (m, 2H), 3.4-3.6 (m, 3H), 3.95 (m, 1H) 7.2-7.5 (m, 15H).

11d 1-O-oleyl-3-O-trityl-sn-glycerol. Prepared from 10d according to General Method H. Yield 77%. $^1$H NMR (CDCl$_3$), δ 0.88 (t, J=7.2, 3H); 1.27 (br, 22H); 1.55 (m, 2H); 2.0 (m, 4H); 2.40 (br, 1H); 3.20 (m, 2H); 3.41-3.56 (m, 4H); 3.95 (m, 1H); 5.35 (m, 2H); 7.25 (m, 9H); 7.45 (m, 6H). ESI-MS 607.75 [M+Na]$^+$ General Method I.

Alkylation and deprotection of 1-O-alkyl-3-O-trityl-sn-glycerols was done as described previously (Kini, G. D., Hostetler, S. E., Beadle, J. R., Aldern, K. A. Synthesis and antiviral activity of 1-O-octadecyl-2-O-alkyl-sn-glycero-3-foscarnet conjugates in human cytomegalovirus-infected cells, *Antiviral Research,* 1997, 36, 115). Briefly, sodium hydride (2.5 eq.) was added to a stirred solution of 1-O-alkyl-3-O-trityl-sn-glycerol (1 eq) in DMF at 0° C. After 20 min, a bromo or methanesulfonate derivative of R$^2$— (1.8 eq.) was added. The reaction mixture was then stirred at room temperature for 5 h or until reaction was substantially complete by TLC. Work up and column chromatography gave 1-O-alkyl-2-O-substituted-3-O-trityl-sn-glycerols which were detritylated with acid. Work up and column chromatography afforded 1-O-alkyl-2-O-substituted-sn-glycerols.

12a 1-O-Tetradecyl-2-O-benzyl-sn-glycerol—Prepared from 11a and benzyl bromide according to General Method I. Structure was confirmed by ESI-MS: 401.51 [M+Na]$^+$ 12b 1-O-Hexadecyl-2-O-benzyl-sn-glycerol—Prepared from 11b and benzyl bromide according to General Method I. $^1$H NMR (300 MHz, CDCl$_3$): δ 7.36-7.27 (m, 5H), 4.65 (m, 2H), 3.79-3.59 (m, 5H), 3.55 (t, 2H), 1.57-1.51 (m, 2H), 1.29 (br s, 26H), 0.89 (t, 3H).

12c 1-O-Hexadecyl-2-O-(3-fluoro-4-methoxybenzyl)-sn-glycerol was prepared from 11b and 3-fluoro-4-methoxybenzyl bromide according to General Method I.

12d 1-O-Octadecyl-2-O-benzyl-sn-glycerol,
12e 1-O-Octadecyl-2-O-benzyl-rac-glycerol,
12f 1-O-Octadecyl-2-O-octyl-sn-glycerol,
12g 1-O-Octadecyl-2-O-(cyclohexylmethyl)-sn-glycerol,
12h 1-O-Octadecyl-2-O-(3-fluorobenzyl)-sn-glycerol,
12i 1-O-Octadecyl-2-O-(4-methoxybenzyl)-sn-glycerol,
12j 1-O-Octadecyl-2-O-(3-fluoro-4-methoxybenzyl)-sn-glycerol, and
12k 1-O-Octadecyl-2-O-(pyridine-3-yl-methyl)-sn-glycerol were prepared from 11c and the appropriate bromide according to General Method I.

12l 1-O-Oleyl-2-O-benzyl-sn-glycerol. Sodium hydride (1.3 eq.) was added to 11d (531 mg, 0.91 mmol) in DMF (4 mL) at 0° C. The resulting mixture was stirred at room temperature for 1 h before benzyl bromide (1.3 eq.) was added. The reaction mixture was stirred at room temperature overnight. Work up and column chromatography afforded 354 mg crude product and 200 mg of 11d was also recovered. Deprotection afforded 12l. $^1$H NMR (300 MHz, Chloroform-d) δ 7.35-7.26 (m, 4H), 5.36-5.32 (m, 2H), 3.84-3.62 (m, 5H), 3.54-3.46 (m, 2H), 3.44 (t, 2H), 2.88-2.75 (m, 2H), 2.02 (m, 4H), 1.54-1.50 (pentet 2H), 1.29 (br s, 22H), 0.88 (t, 3H). 455.73 [M+Na]$^+$ 12m 1-O-Oleyl-2-O-(3-fluoro-4-methoxybenzyl)-sn-glycerol. Prepared from 11d and 3-fluoro-4-methoxybenzyl bromide according to General Method I. $^1$H NMR (300 MHz, Chloroform-d) δ 7.12 (m, 2H), 6.95 (t, 1H), 5.36-5.32 (m, 2H), 4.65-4.52 (dd, 2H), 3.75-3.70 (m, 2H), 3.67-3.60 (m, 2H), 3.57-3.55 (m, 2H), 3.45 (t, 2H), 2.01-1.97 (m, 2H), 1.28 (br s, 16H), 0.87 (t, 3H). ESI-MS: 503.79 [M+Na]$^+$ Synthesis of 1-O-Alkyl-2-O-Substituted-sn-glyceryl esters of GS-441524 5'-monophosphate (Scheme 3, 15a-m)

The following scheme depicts embodiments of synthesis steps used to produce 1-O-alkyl-2-O-substituted-sn-glyceryl esters of GS-441524 5'-monophosphate.

Scheme 3. Synthesis of 1-O-Alkyl-2-O-substituted-sn-glyceryl esters of GS-441524 5'-monophosphate.

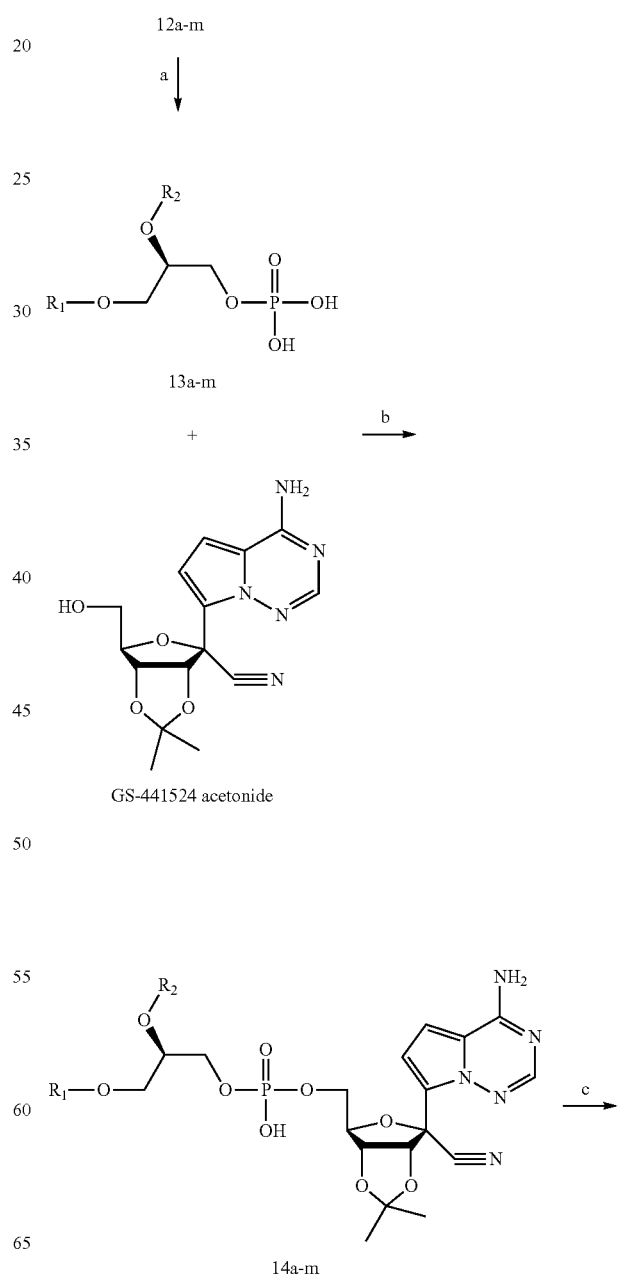

-continued

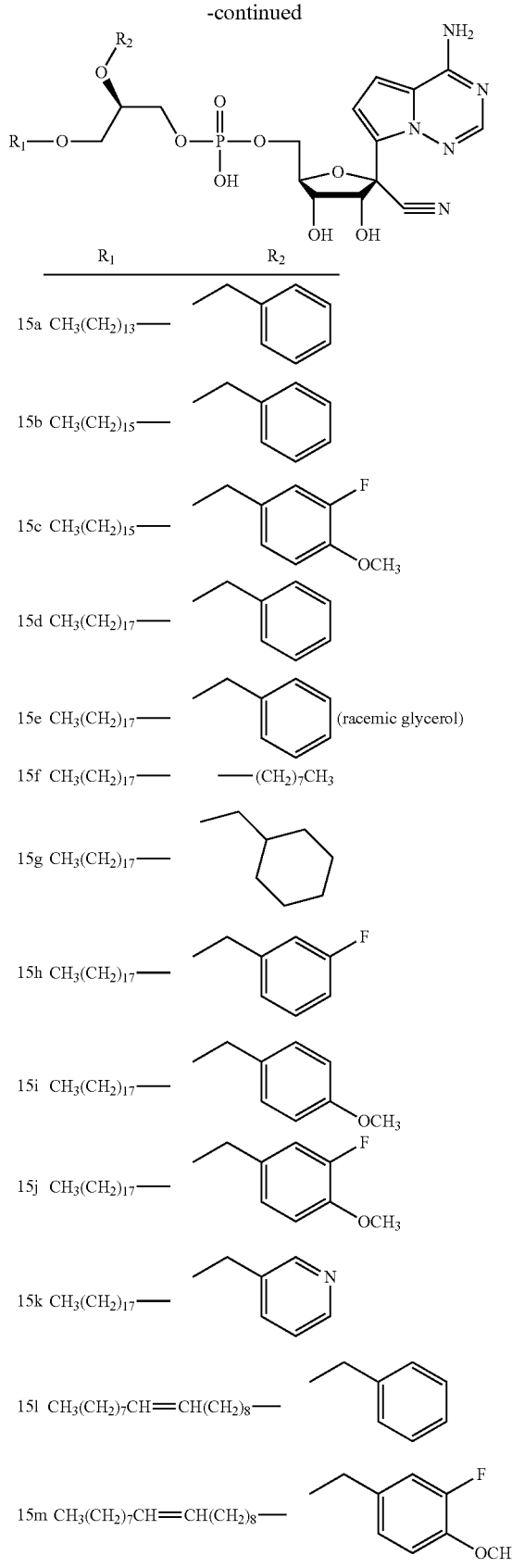

Reagents: a) POCl₃ or bis(trichloroethyl) chlorophosphate/zinc powder; b) DCC/DMAP or DIC/NMI, pyridine; c) formic acid or con HCl/THF.

General Method J. Phosphorylation of 1-O-alkyl-2-O-substituted-sn-glycerols was accomplished as described in the literature (Kates, M., Adams, G. A., Blank, M. L., Snyder, F. M. (1991). Chemical synthesis and physiological activity of sulfonium analogues of platelet activating factor. Lipids, 26, 1095-1101). Briefly, 1-O-alkyl-2-O-substituted-sn-glycerols (11.5 mmol) and 1-methylimidazole (14.4 mmol) were dissolved in dry pyridine (100 mL) and stirred at room temperature. A solution of bis(trichloroethyl) chlorophosphate (5.5 g, 14.4 mmol) in diethyl ether (20 mL) was added dropwise over 10 min, then the mixture was stirred overnight. Analysis by TLC showed complete phosphorylation. Water (10 mL) was added to quench excess reagent and then the mixture was concentrated by rotary evaporation, and co-evaporated with toluene to remove pyridine. The residue was adsorbed onto silica gel 60 (ca. 30 g) and purified by flash column chromatography. Gradient elution 100% hexanes to 25% EtOAc/hexanes was used to isolate protected phosphorylated product.

Products (9.65 mmol) were dissolved in a mixture of chloroform (50 mL) and glacial acetic acid (90 mL), and then vigorously stirred and cooled with an ice water bath. Zinc powder (5 g) was added to the mixture, stirred for 1 hour and then the ice water bath was removed, and stirring was continued for another 2 hours. The remaining zinc was removed by vacuum filtration and the clear filtrate was concentrated by rotary evaporation. The residue was taken up in 20% MeOH/CH₂Cl₂ (250 mL) and extracted with 1 M HCl (3×50 mL), then the organic layer was concentrated and co-evaporated with ethanol (2×50 mL). The waxy residue was dissolved in 1,4-dioxane, frozen, then lyophilized in vacuo (18 h) to provide glyceryl phosphates.

Compounds 13a, 13b, 13c, 13d, 13e, 13f, 13g, 13h, 13i, 13j, and 13k were prepared according to General Method J.

13l 1-O-Oleyl-2-O-benzyl-sn-glyceryl-3-phosphate. Prepared according to General Method A. $^1$H NMR (300 MHz, Chloroform-d) δ 7.36-7.23 (m, 5H), 5.36-5.32 (m, 2H), 4.69 (d, J=11.9 Hz, 1H), 4.62 (d, J=11.8 Hz, 1H), 4.11-4.09 (m, 2H), 3.80-3.77 (m, 2H), 3.76-3.69 (m, 1H), 3.53-3.47 (m, 1H), 3.42 (t, 2H), 2.00 (tq, J=7.1, 3.7 Hz, 4H), 1.50 (m, 2H), 1.26 (br s, 22H), 0.87 (t, 3H). ESI-MS: 513.72 [M+1]$^+$ 13m 1-O-Oleyl-2-O-(3-fluoro-4-methoxybenzyl)-sn-glyceryl-3-phosphate. Prepared according to General Method A.

Coupling of Phosphates 13a-m to GS-441524 Acetonide (Remdesivir Nucleoside, RVn Acetonide 14a 1-O-Tetradecyl-2-O-benzyl-sn-glyceryl-phospho-RVn acetonide—Prepared from GS-441524 acetonide and 13a according to General Method C. Structure was confirmed by ESI-MS 770.50 [M–H]$^-$.

14b 1-O-Hexadecyl-2-O-benzyl-sn-glyceryl-phospho-RVn acetonide—Prepared from GS-441524 acetonide and 13b according to General Method C.

14c 1-O-Hexadecyl-2-O-(3-fluoro-4-methoxy-benzyl)-sn-glyceryl-phospho-RVn acetonide—Prepared from GS-441524 acetonide and 13c according to General Method C.

14d 1-O-Octadecyl-2-O-benzyl-sn-glyceryl-phospho-RVn acetonide—Prepared from GS-441524 acetonide and 13d according to General Method B. N,N-Dicyclohexylcarbodiimide (DCC, 310 mg, 1.5 mmol) was added to a mixture of acetonide (300 mg, 0.91 mmol), phosphate 13d (515 mg, 1.0 mmol), and 4-dimethylaminopyridine (DMAP, 122 mg, 1.0 mmol) in 25 mL of dry pyridine, and then the mixture was heated to 90° C. and stirred for 24 h. Pyridine was then evaporated and the residue was purified by flash column chromatography on silica gel 60. Gradient elution ($CH_2Cl_2$/methanol 10-20%) afforded 210 mg (28% yield) of compound 14d. ESI MS 826.58 $[M-H]^-$.

14e 1-O-Octadecyl-2-O-benzyl-rac-glyceryl-phospho-RVn acetonide.—Prepared from GS-441524 acetonide and 13e according to General Method C.

14f 1-O-Octadecyl-2-O-octyl-sn-glyceryl-phospho-RVn acetonide—Prepared from GS-441524 acetonide and 13f according to General Method C.

14g 1-O-Octadecyl-2-O-(cyclohexylmethyl)-sn-glyceryl-phospho-RVn acetonide—May be prepared from GS-441524 acetonide and 13g according to General Method C.

14h 1-O-Octadecyl-2-O-(3-fluoro-benzyl)-sn-glyceryl-phospho-RVn acetonide—Prepared from GS-441524 acetonide and 13h according to General Method C.

14i 1-O-Octadecyl-2-O-(4-methoxy-benzyl)-sn-glyceryl-phospho-RVn acetonide.—May be prepared from GS-441524 acetonide and 13i according to General Method C.

14j 1-O-Octadecyl-2-O-(3-fluoro-4-methoxy-benzyl)-sn-glyceryl-phospho-RVn acetonide—Prepared from GS-441524 acetonide and 13j according to General Method C.

14k 1-O-Octadecyl-2-O-(pyridine-3-yl-methyl)-sn-glyceryl-phospho-RVn acetonide—May be prepared from GS-441524 acetonide and 13k according to General Method C.

14l 1-O-Oleyl-2-O-benzyl-sn-glyceryl-phospho-RVn acetonide Prepared from GS-441524 acetonide and 13l according to General Method B.

14m 1-O-Oleyl-2-O-(3-fluoro-4-methoxy-benzyl)-sn-glyceryl-phospho-RVn acetonide Prepared from GS-441524 acetonide and 13m according to General Method B.

Removal of Acetonide Protecting Group 15a 1-O-Tetradecyl-2-O-benzyl-sn-glyceryl-phospho-RVn—Prepared from Compound 14a according to General Method E and isolated as an off-white powder. Structure was confirmed by ESI-MS $[M-H]^-$=730.41.

15b 1-O-Hexadecyl-2-O-benzyl-sn-glyceryl-phospho-RVn. Prepared from Compound 14b according to General Method E. $^1$H NMR (500 MHz, DMSO-$d_6$) δ 7.94 (s, 1H), 7.89 (s, 1H), 7.81 (s, 1H), 7.32-7.25 (m, 3H), 7.22 (ddd, J=8.7, 5.4, 2.6 Hz, 1H), 6.88 (d, J=4.5 Hz, 1H), 6.80 (d, J=4.5 Hz, 1H), 6.24 (s, 1H), 5.95 (d, J=4.0 Hz, 1H), 4.55 (q, J=12.1, 12.1, 12.1 Hz, 3H), 4.09 (dt, J=6.7, 4.3, 4.3 Hz, 1H), 3.92 (d, J=4.5 Hz, 1H), 3.78 (dtt, J=24.4, 7.8, 7.8, 4.4, 4.4 Hz, 2H), 3.66-3.55 (m, 3H), 3.43 (dd, J=10.6, 3.5 Hz, 1H), 3.32-3.28 (m, 2H), 1.42 (q, J=6.5, 6.5, 6.0 Hz, 2H), 1.20 (d, J=7.7 Hz, 24H), 0.83 (t, J=7.0, 7.0 Hz, 3H). LC/MS purity=99.8%; $[M+H]^+$ 760.6.

15c 1-O-Hexadecyl-2-O-(3-fluoro, 4-methoxybenzyl)-sn-glyceryl-phospho-RVn. Prepared from Compound 14c according to General Method E. $^1$H NMR (500 MHz, DMSO-$d_6$) δ 7.89 (s, 1H), 7.80 (s, 1H), 7.11 (d, J=12.3 Hz, 1H), 7.04 (d, J=6.1 Hz, 2H), 6.87 (d, J=4.6 Hz, 1H), 6.81 (d, J=4.5 Hz, 1H), 6.17 (s, 1H), 4.56 (d, J=5.0 Hz, 1H), 4.52-4.41 (m, 2H), 4.10 (s, 1H), 3.93 (q, J=5.4, 5.2, 5.2 Hz, 1H), 3.78 (s, 3H), 3.63 (s, 2H), 3.57 (d, J=4.6 Hz, 1H), 3.41 (dd, J=10.4, 3.5 Hz, 1H), 3.29 (s, 3H), 1.41 (d, J=6.5 Hz, 2H), 1.25-1.17 (m, 24H), 0.83 (t, J=7.0, 7.0 Hz, 3H). LC/MS purity 99.8%; $[M+H]^+$ 808.9.

15f 1-O-Octadecyl-2-O-octyl-sn-glyceryl-phospho-RVn—Prepared from Compound 14f according to General Method E. $^1$H NMR (500 MHz, DMSO-$d_6$) δ 7.89 (s, 1H), 7.79 (s, 1H), 6.88 (d, J=4.5 Hz, 1H), 6.80 (d, J=4.5 Hz, 1H), 6.10 (s, 1H), 5.92 (s, 1H), 4.56 (t, J=5.2, 5.2 Hz, 1H), 4.08 (t, J=5.7, 5.7 Hz, 1H), 3.91 (q, J=5.0, 4.9, 4.9 Hz, 1H), 3.79 (d, J=18.1 Hz, 3H), 3.54 (d, J=19.3 Hz, 3H), 3.46-3.35 (m, 5H), 3.33 (s, 2H), 3.27-3.23 (m, 1H), 1.41 (dt, J=16.0, 7.4, 7.4 Hz, 4H), 1.21 (d, J=4.5 Hz, 36H), 0.83 (td, J=7.1, 7.0, 5.7 Hz, 6H). LC/MS purity 99.7%; $[M+H]^+$ 810.7.

15g 1-O-Octadecyl-2-O-(ethylcyclohexyl)-sn-glyceryl-phospho-RVn—May be prepared from Compound 14g according to General Method E.

15h 1-O-Octadecyl-2-O-(3-fluoro-benzyl)-sn-glyceryl-phospho-RVn—Prepared from Compound 14h according to General Method E. $^1$H NMR (500 MHz, DMSO-$d_6$) δ 8.47 (s, 2H), 7.88 (s, 2H), 7.36-7.26 (m, 1H), 7.12 (q, J=8.4, 6.9, 6.9 Hz, 2H), 7.03 (td, J=8.5, 8.4, 2.9 Hz, 1H), 6.88 (d, J=4.5 Hz, 1H), 6.80 (d, J=4.5 Hz, 1H), 6.30 (s, 1H), 5.97 (s, 1H), 4.64-4.50 (m, 3H), 4.13-4.07 (m, 1H), 3.92 (t, J=5.8, 5.8 Hz, 1H), 3.79 (dddd, J=33.7, 12.0, 7.6, 4.3 Hz, 2H), 3.63 (dtt, J=14.0, 10.1, 10.1, 5.7, 5.7 Hz, 3H), 3.43 (dd, J=10.7, 3.4 Hz, 2H), 1.43 (p, J=6.5, 6.5, 6.5, 6.5 Hz, 2H), 1.20 (d, J=11.1 Hz, 30H), 0.83 (t, J=6.9, 6.9 Hz, 3H). LC/MS purity 98.7%; $[M+H]^+$ 806.8.

15i 1-O-Octadecyl-2-O-(4-methoxybenzyl)-sn-glyceryl-phospho-RVn—May be prepared from Compound 14i according to General Method E.

15j 1-O-Octadecyl-2-O-(3-fluoro-4-methoxy-benzyl)-sn-glyceryl-phospho-RVn-Prepared from Compound 14j according to General Method E. $^1$H NMR (500 MHz, DMSO-$d_6$) δ 8.43 (d, J=6.7 Hz, 2H), 7.99-7.73 (m, 2H), 7.04 (d, J=5.5 Hz, 1H), 6.87 (q, J=3.7, 3.7, 3.2 Hz, 1H), 6.82 (dd, J=7.3, 4.3 Hz, 1H), 6.17-5.74 (m, 1H), 4.59 (t, J=4.9, 4.9 Hz, 1H), 4.53-4.41 (m, 1H), 4.11 (q, J=4.9, 4.9, 4.9 Hz, 1H), 3.93 (q, J=5.4, 5.4, 5.4 Hz, 1H), 3.84 (dq, J=11.3, 6.5, 5.1, 5.1 Hz, 1H), 3.80-3.70 (m, 3H), 3.61 (ddd, J=27.7, 10.9, 5.2 Hz, 3H), 3.30 (dd, J=6.6, 3.0 Hz, 3H), 3.21 (dq, J=9.8, 5.1, 5.1, 4.9 Hz, 1H), 1.43 (p, J=6.6, 6.6, 6.5, 6.5 Hz, 2H), 1.27-1.16 (m, 30H), 0.83 (t, J=6.8, 6.8 Hz, 3H). LC/MS purity 94.7%; $[M+H]^+$ 836.8.

15k 1-O-Octadecyl-2-O-(pyridine-3-yl-methyl)-sn-glyceryl-phospho-RVn—May be prepared from Compound 14k according to General Method E.

15l 1-O-Oleyl-2-O-benzyl-sn-glyceryl-phospho-RVn Prepared from Compound 14l according to General Method D and isolated as an off-white solid in 84% yield. $^1$H NMR (300 MHz, $CDCl_3$+$CD_3OD$) δ 7.79 (s, 1H), 7.38 (s, 2H), 7.27-7.21 (m, 5H), 6.92 (d, J=6.0 Hz, 1H), 6.90 (d, J=6.0 Hz, 1H), 5.30 (t, J=6.0 Hz, 2H), 4.70 (d, J=11 Hz, 1H), 4.62 (d, J=5 Hz, 1H), 4.34-4.49 (m, 1H), 4.20 (m, 1H), 3.90-3.87 (m, 2H), 4.18-4.06 (m, 2H), 3.71-3.69 (m, 2H), 3.52 (ddd, J=11.7, 3.1, 1.3 Hz, 1H), 3.35 (t, 2H), 1.96-1.93 (m, 4H) 1.49-1.47 (m, 2H), 1.33-1.23 (m, 20H), 0.83 (t, 2H). LC/MS purity 99%; $[M+H]^+$ 786.78.

15m 1-O-Oleyl-2-O-(3-fluoro, 4-methoxybenzyl)-sn-glyceryl-phospho-RVn Prepared from Compound 14m according to General Method D and isolated as an off white solid. Yield was 92%. $^1$H NMR (300 MHz, $CD_3OD$) δ 7.74 (s, 1H), 7.32 (s, 2H), 6.99 (d, J=6.0 Hz, 1H), 6.92-6.77 (m, 3H), 5.23 (t, J=6.0 Hz, 2H), 4.67 (d, J=11 Hz, 1H), 4.49 (d, J=5 Hz, 2H), 4.30 (m, 1H), 4.20 (m, 1H), 3.83-3.81 (m, 2H), 3.75 (s, 3H), 3.63 (m, 1H), 3.31 (t, 2H), 1.91-1.89 (m, 4H), 1.44 (m, 2H), 1.18 (br s, 22H), 0.77 (t, 2H). LC/MS purity 99%; $[M+H]^+$ 834.87.

D. Synthesis of 1-O-octadecyl-2-O-benzyl-sn-glycerol-benzyl-phospho-RVn

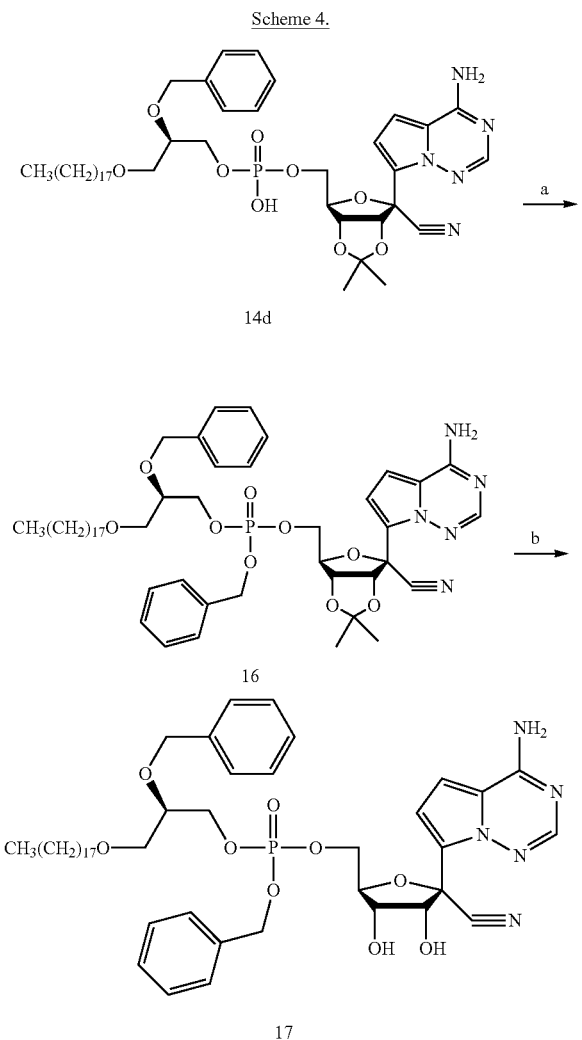

Reagents:
a) benzyl alcohol, PyBOP, DIEA, DMF;
b) formic acid, rt

Compound 14d (160 mg, 0.22 mmol), benzyl alcohol (48 mg, 0.45 mmol), diisopropylethylamine (DIEA, 58 mg, 0.45 mmol), and (1H-benzotriazol-1-yloxy)-tripyrrolidinophosphonium hexafluorophosphate (PyBOP, 230 mg, 0.45 mmol) in dry DMF (5 mL) were stirred at room temperature for 3 h. DMF was then evaporated, and the residue was dissolved in ethyl acetate (50 mL) and washed with saturated $NaHCO_3$ (3×10 mL). The organic layer was dried over $MgSO_4$ and concentrated. The residue was purified by column chromatography on silica gel, eluting with chloroform/methanol (0-15%) to yield 16. ESI-MS 918.33 $[M-H]^-$.

Compound 16 was added to formic acid and the deprotection was monitored by TLC. The mixture was concentrated under vacuum and the residue was purified by column chromatography (silica gel, dichloromethane/methanol 10-20%) to give Compound 17. Structure was confirmed by ESI-MS: 878.35 $[M+H]^+$, 900.43 $[M+Na]^+$.

E. Synthesis of GS-441524-3'5'Cyclic Monophosphate, 1-O-octadecyl-2-O-benzyl-sn-glycerol Ester In another embodiment, compounds of the invention are 3',5'-cyclic phosphates. The 3',5'-cyclic phosphates may be prepared from known or readily prepared starting materials, following methods known to one skilled in the art of organic synthesis. As an example, 3',5'-cyclic phosphate 18 may be prepared from phosphodiester 15d by an intramolecular esterification reaction.

A solution of 1-O-octadecyl-2-O-benzyl-sn-glyceryl-phospho-RVn (1 mmol) in dry pyridine (25 mL) is added dropwise to a solution of triisopropylbenzenesulfonyl chloride (3 mmol) and 1-methylimidazole (1 mmol) in dry pyridine (100 mL). The mixture is stirred for 2 days at room temperature or until TLC indicates substantial conversion to the 3',5'-cyclic phosphate. Solvents are evaporated under vacuum, and the residue is purified by column chromatography on silica gel to yield compound 18 as a mixture of the equatorial and axial isomers. The isomers may be separated using either preparative-HPLC, or preparative Chiral-HPLC before antiviral testing.

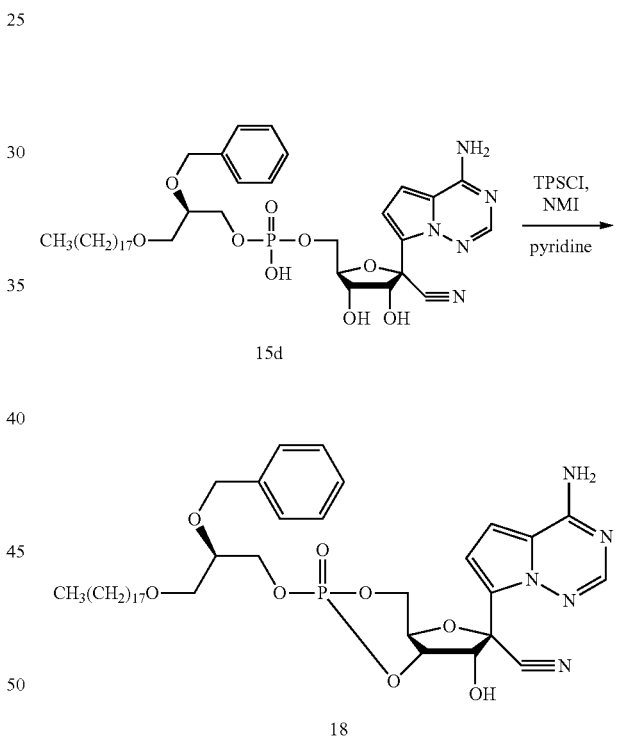

To measure cell-based anti-SARS CoV-2 activity of RVn 3',5'-cycl remdesivir, RDV remdesivir nucleoside, RVn 2,3-isopropylidene-RVn, RVa RVn triphosphate The compounds of this example were assayed for anti-coronavirus activity in Vero E6 cells in comparison with remdesivir (RDV) and the remdesivir nucleoside (RVn). Ten thousand Vero E6 cells were seeded in 100 microliters of culture medium in 96 well plates. The following day serial two-fold dilutions of antiviral compounds or the DMSO-containing vehicle were added to each well. The USA WA-01 strain of SARS CoV-2 was added to each well at a multiplicity of infection of 0.1 thirty minutes later. Cells were incubated for 48 hours, washed twice in PBS and lysed with TRIzol. RNA was extracted using Directzol micro RNA columns. RNA was made into cDNA and assayed for the SARS CoV-2 spike protein and for a housekeeping gene (RPLPO) RNA by qPCR. Data represents the average of duplicate wells. Cellular cytotoxicity was also measured in VERO E6 cells. As below, each of the synthesized compounds exhibited enhanced anti-SARS CoV-2 activity compared to remdesivir or the remdesivir nucleoside with selectivity indices ranging from 22.8 to >227. Cytotoxicity ($CC_{50}$) was assessed using a commercially available MTT assay.

As shown in the following Table, ODE-P-RVn (4c) and ODBG-P-RVn (15d) were 9 to 15 times more active against the USA WA-1 strain of SARS-CoV-2019 in Vero E6 cells. Likewise, HDP-P-RVn (4b) was 3.3-fold more active than remdesivir.

| Compound | $EC_{50}$ (μM) | $EC_{90}$ (μM) | $CC_{50}$ (μM) | Selectivity Index |
|---|---|---|---|---|
| RDV | 3.16 | 5.50 | >50 | >15.8 |
| ODE-P-RVn (4c) | 0.35 | 0.53 | >50 | >143 |
| ODBG-P-RVn (15d) | 0.21 | 0.56 | >50 | >238 |
| HDP-P-RVn (4b) | 0.84 | 1.58 | 21 | 25.0 |
| RVn | 1.56 | 2.69 | >50 | >32.0 |

Abbreviations:
$EC_{50}$, 50% effective concentration;
$EC_{90}$, 90% effective concentration;
$CC_{50}$, 50% cytotoxic concentration.
Selective Index = $CC_{50}/EC_{50}$.

Example 3. Additional Synthesis and Testing of RVn Monophosphate Prodrugs

Figure 1F:
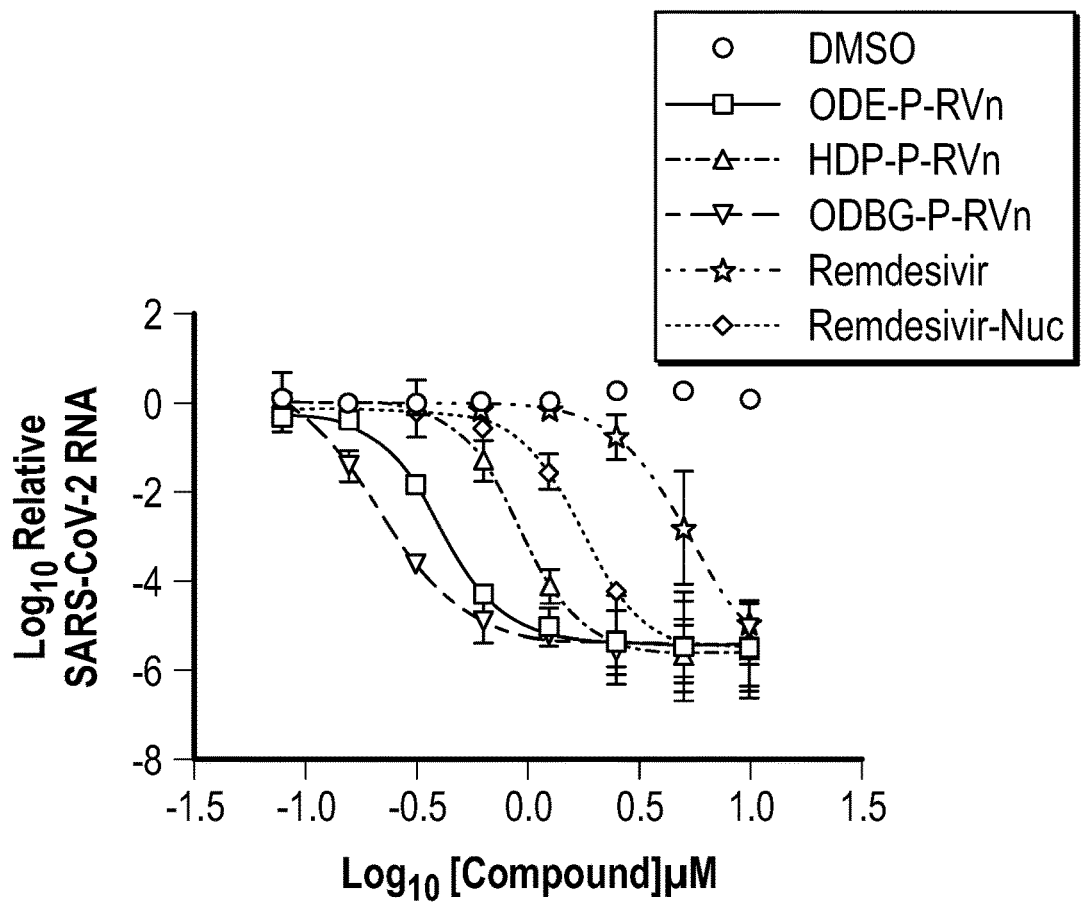
FIG. 1F depicts the concentration-response curves of FIG. 1A-FIG. 1E.

Antiviral Activity: Also generated were concentration-response curves for ODBG-P-RVn (15d), ODE-P-RVn (4c), and HDP-P-RVn (4b), remdesivir (RDV) and remdesivir nucleoside (RVn) for SARS-CoV-2 infection in Vero E6 cells in two separate experiments performed in duplicate (FIG. 1A-FIG. 1F). Dose response curves for three remdesivir analogs (FIG. 1A, FIG. 1B, and FIG. 1C), remdesivir (GS-5734) (FIG. 1D), and remdesivir nucleoside (GS-441524) (FIG. 1E) against SARS-CoV-2 infection in Vero E6 cells. Vero E6 cells were pretreated with the indicated dose of the indicated drug for thirty minutes and then infected with SARS-CoV-2 isolate USA-WA1/2020 for 48 hours. The relative SARS-CoV-2 Spike RNA expression was determined by qRT-PCR. Each dose-response comparison was conducted simultaneously for all drugs on 2 separate occasions. Data from both experiments are shown at FIG. 1A-FIG. 1F. Data points indicate the mean relative expression from duplicate wells. Error bars represent the standard deviations (SDs). The black vertical dashed line indicates the concentrations at which there is 50% inhibition ($EC_{50}$). (FIG. 1F). Combined inhibition curves for all five compounds and DMSO on a single chart. DMSO, which was the vehicle for all compounds, had no effect on SARS-CoV-2 replication at the concentrations used. The three lipid esters of RVn-monophosphate were all substantially more active than RDV and RVn.

The following Table shows the effective concentrations ($EC_{50}$, $EC_{90}$), 50% cytotoxic concentration ($CC_{50}$), and selectivity index of the compounds, mean±SD. Cytotoxicity ($CC_{50}$) was assessed using Cell Titer Glo. The $EC_{50}$ values of RDV and RVn were 4.6 and 1.7 μM, respectively. The lipid prodrugs were more active with $EC_{50}$s of ranging from 0.19±0.023 to 0.96±0.17. ODBG-P-RVn and ODE-P-RVn were the most active and selective compounds. Based on the $EC_{50}$ values the most active compound, ODBG-P-RVn, was 24 times more active than RDV and 8.9 times more active than RVn (p<0.001 and 0.005) with a selectivity index of 240.

| Antiviral Activity, Cytotoxicity and Selectivity of the Compounds | | | | | |
|---|---|---|---|---|---|
| Compound | $EC_{50}$ (µM) | $EC_{90}$ (µM) | $CC_{50}$ (µM) | Selectivity | p value vs RDV, RVn |
| Remdesivir | 4.6 ± 2.1 | 8.9 ± 4.9 | >100 | >21.7 | — |
| Remdesivir nucleoside | 1.7 ± 0.13 | 3.2 ± 0.77 | >100 | >58.8 | — |
| HDP-P-RVn, 5a | 0.96 ± 0.17 | 2.1 ± 0.78 | 51 | 52 | 0.02, 0.59 |
| ODE-P-RVn, 5b | 0.47 ± 0.18 | 1.1 ± 0.80 | >100 | >212 | 0.004, 0.047 |
| ODBG-P-RVn, 5c | 0.19 ± 0.023 | 0.56 ± 0.0002 | 46 | 240 | <0.001, 0.005 |

A graph showing the $CC_{50}$ results by Cell Titer Glo is shown in the Supplemental Materials.
Abbreviations:
RDV, Remdesivir (GS-5734);
RVn, Remdesivir nucleoside (GS-441524);
HDP-P-, hexadecyloxypropyl-P-;
ODE-P-, octadecyloxyethyl-P-;
ODBG-P-, 1-O-octadecyl-2-O-benzyl-glycero-3-P-;
Selectivity index, $CC_{50}/EC_{50}$;
statistical analysis comparing $LogIC_{50}$ values from separate experiments by one-way ANOVA.

Of all the perceived disadvantages of RDV, it was chosen in this example to design prodrugs of RVn which could provide oral bioavailability because an effective oral drug would allow for much earlier treatment of persons diagnosed with SARS-CoV-2 infection. As shown in this example, this was accomplished by constructing liponucleotides of RVn resembling lysophospholipids that are normally absorbed in the GI tract. The RVn liponucleotides were not metabolized rapidly in plasma and gain rapid entry to the cell often exhibiting greatly increased antiviral activity.

In contrast to the activation of RDV which required four transformations, intracellular kinase bypass with this kind of compound generated the nucleoside monophosphate when the lipid ester moiety was cleaved in a single reaction catalyzed by acid phospholipase C or acid sphingomyelinase (sphingomyelin phosphodiesterase I).

One of the compounds, ODBG-P-RVn (15d) was likely to deliver relatively more drug to lung and less to liver as shown previously in lethal mousepox infection tHostetler K Y, Beadle J R, Trahan J, Aldern K A, Owens G, Schriewer J, Melman L, Buller R M. Oral 1-O-octadecyl-2-O-benzyl-sn-glycero-3-cidofovir targets the lung and is effective against a lethal respiratory challenge with ectromelia virus in mice. Antiviral Res. 2007 March; 73(3):212-8. doi: 10.1016/j.antiviral.2006.10.009. Epub 2006 Nov. 9. PMID: 17123638; PMCID: PMC1859865).

The synthesis of the lipid prodrugs of this example was much simpler than RDV and was readily scalable.

In this example, three lipid prodrugs of RVn were synthesized that were substantially more active than RDV or RVn in Vero E6 cells. The two most active compounds ODBG-P-RVn and ODE-P-RVn were 24 and 9.8 times more active than RDV. These compounds were expected to be orally bioavailable, stable in plasma and provide significant exposure and antiviral activity to all tissues infected with SARS-CoV-2.

Compounds: Remdesivir (GS-5734) and remdesivir nucleoside (GS-441524) were purchased from AA Blocks (San Diego, CA and Mason-Chem (Palo Alto, CA), respectively.

Cells: Vero E6 were obtained from ATCC and grown in DMEM (Corning) with 10% FBS and Penicillin-Streptomycin (Gibco).

SARS-CoV-2 infection: SARS-CoV-2 isolate USA-WA1/2020 (BEI Resources) was propagated and infectious units quantified by plaque assay using Vero E6 (ATCC) cells. Approximately $10^4$ Vero E6 cells per well were seeded in a 96 well plate and incubated overnight. Compounds or controls were added at the indicated concentrations 30 minutes prior to infection followed by the addition of SARS-CoV-2 at a multiplicity of infection equal to 0.01. After incubation for 48 hours at 37° C. and 5% $CO_2$, cells were washed twice with PBS and lysed in 200 ul TRIzol (ThermoFisher).

RNA extraction, cDNA synthesis and qPCR: RNA was purified from TRIzol lysates using Direct-zol RNA Microprep kits (Zymo Research) according to manufacturer recommendations that included DNase treatment. RNA was converted to cDNA using the iScript cDNA synthesis kit (BioRad) and qPCR was performed using iTaq universal SYBR green supermix (BioRad) and an ABI 7300 real-time pcr system. cDNA was amplified using the following primers RPLP0 F—GTGTTCGACAATGGCAGCAT; RPLP0 R—GACACCCTCCAGGAAGCGA; SARS-CoV-2 Spike F—CCTACTAAATTAAATGATCTCTGCTTTACT; SARS-CoV-2 Spike R—CAAGC-TATAACGCAGCCTGTA. Relative expression of SARS-CoV-2 Spike RNA was calculated by delta-delta-Ct by first normalizing to the housekeeping gene RPLP0 and then comparing to SARS-CoV-2 infected Vero E6 cells that were untreated (reference control). Curves were fit and 50 and 90% effective concentrations $EC_{50}$ and $EC_{90}$ values calculated using Prism 8.

CellTiter-glo luminescent cell viability assay: Approximately $10^4$ Vero E6 cells per well were seeded in opaque walled 96 well cell culture plates and incubated overnight.

Compounds or controls were added at the indicated concentrations. After incubation for 48.5 hours at 37° C. and 5% $CO_2$, an equal volume of CellTiter-Glo reagent (Cat. #G7570, Promega, Madison, WI) was added, mixed and luminescence recorded on an EnSpire Multimode Plate Reader (PerkinElmer) according to manufacturer recommendations.

Viability was calculated compared to untreated controls and $CC_{50}$ values were calculated using Prism 8 (Table S10).

Determination of Cytotoxicity: The 50% cytotoxic concentrations ($CC_{50}$) were determined with Cell Titer Glo (Cat. #G7570, Promega, Madison, WI) according to the manufacturer's instructions. The calculated $CC_{50}$ values are shown in the foregoing table.

Figure 2:
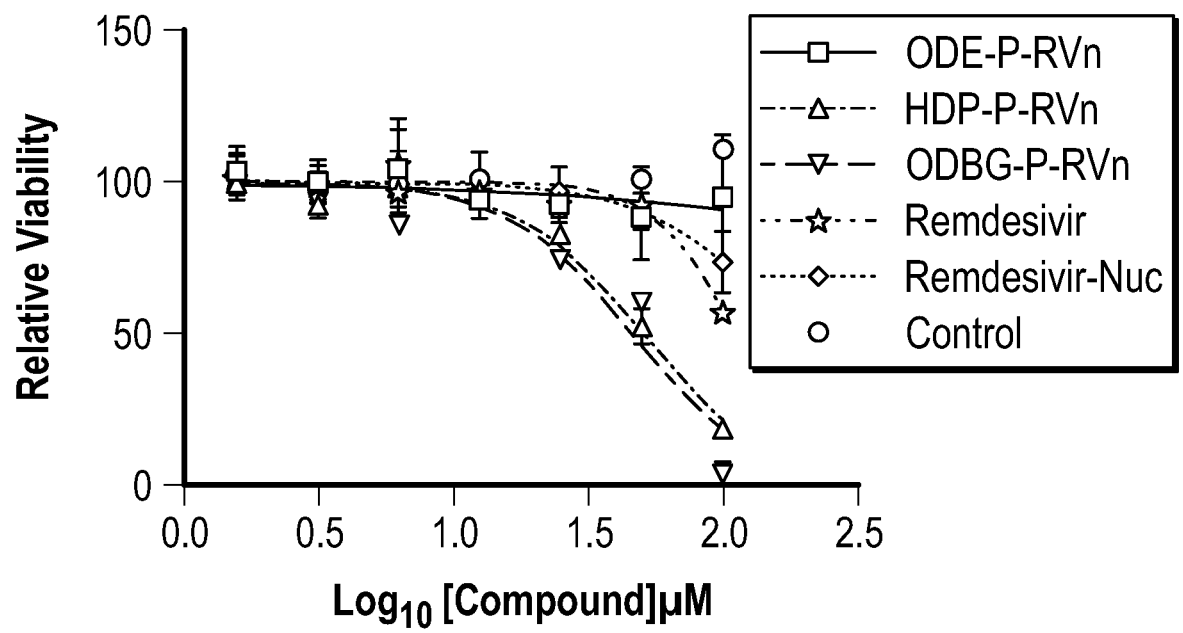
FIG. 2 depicts a plot of the relative viabilities of several embodiments of compounds described herein, remdesivir, and a remdesivir nucleoside.

Vero E6 cells were treated with increasing concentrations of remdesivir analogs, remdesivir (GS-5734), remdesivir nucleoside (GS441524) or DMSO vehicle (control) for 48.5 hrs. Relative viability was measured by CellTiter-Glo luminescent cell viability assay, as depicted at FIG. 2.

Example 4—Generation of Remdesivir Triphosphate in Vero E6 Cells

In this example, Vero E6 cells were plated in 6 well plates at about $3.4 \times 10^5$ cells per well in 2 mL of media (DMEM, 10% FBS).

Cells were then incubated at 37° C. for 24 hours. Media was then aspirated and replaced with 2 ml of control media (fresh Dulbecco's Modified Eagle's Medium (DMEM), 10% FBS) or 2 mL of media with drug at a concentration of 1 μM. Cell were incubated with the various drugs for 48 hours. The media was aspirated, the cells rinsed twice with phosphate-buffered saline (PBS), trypsinized for 5 minutes with 1 mL ATV, triturated and removed to a 15 mL centrifuge tube, rinsed with 1 mL PBS, which was also then removed to the 15 mL centrifuge tube, and the cells were triturated again. Cells were counted in a Reichert hemocytometer using two 10 μL samples, and the number of cells in each sample was determined.

Figure 3:
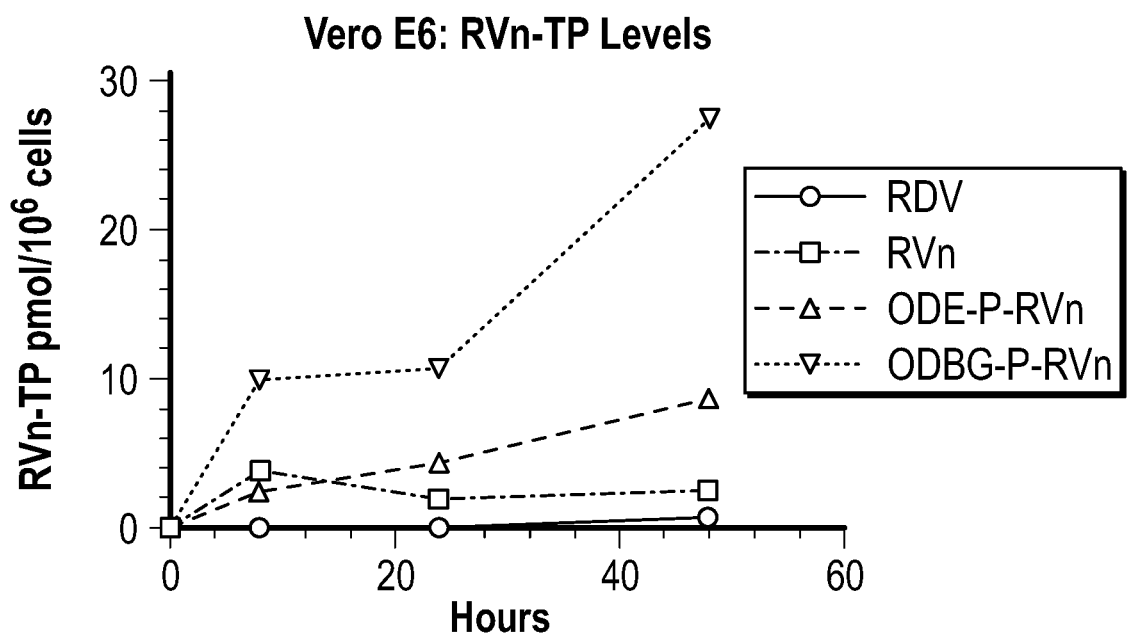
FIG. 3 depicts the results of an embodiment in which the synthesis of remdesivir triphosphate was conducted in Vero E6 cells.

Cells were centrifuged at 1200 rpm for 10 minutes, diluent aspirated and the pellet resuspended in 250 μL of methanol/distilled water (70/30) and analyzed by LC/MS/MS. The results, which are depicted at FIG. 3, were in picomoles/$10^6$ cells and are the average of two or three determinations. Abbreviations for FIG. 3: RDV, remdesivir; RVn, remdesivir nucleoside (GS-441524); ODE-P-RVn, octadecyloxyethyl-phospho-RVn (4c); ODBG-P-RVn, 1-O-octadecyl-2-O-benzyl-glyceryl-sn-3-phospho-RVn (15d)

As depicted at FIG. 3, in Vero E6 cells, the synthesis of remdesivir triphosphate (RVn-TP) increased progressively to 48 hours with exposure to 1 micromolar ODE-P-RVn and OBDG-P-RVn. With RVn the levels of RVn-TP peaked at 8 hours and declined thereafter. Levels of RVn-TP with RDV were below the level of quantification at 8 and 24 hours.

Example 5—Human Coronavirus 229E Infection

In this example, human Coronavirus 229E (ATCC) was propagated and infectious units quantified by $TCID_{50}$ using MRC-5 cells. For antiviral testing, approximately 104 MRC-5 cells were seeded per well in EMEM (10% FCS) at 37° C. in a 96 well plate overnight. Medium from each well was removed and cells were infected with 100 $TCID_{50}$ virus in 100 μL medium for two hours.

Cells were washed one time with medium and then compounds or controls added at the indicated concentrations. After three days, CPE was observed under microscope and quantified using an MTT cell proliferation assay kit (Abcam) read on an ELx800, Universal Microplate reader (BIO-TEK Instruments, INC).

Effect of Compounds on HCoV-229E Replication in MRC-5 Cells

| | | | | HCoV-229E in MRC-5 Cells | | |
|---|---|---|---|---|---|---|
| Entry | Compd | $R_1$ | $R_2$ | $EC_{50}$ (μM) | $EC_{90}$ (μM) | $CC_{50}$ (μM) |
| 1 | 4a | eicosyl | H | ±0.91 ± 1.21 | ±1.80 ± 1.87 | ±>50 |
| 2 | 4b | hexadecyloxypropyl | H | 3.02 ± 0.36 | 6.60 ± 1.14 | 32.1 ± 17.9 |
| 3 | 4c | octadecyloxyethyl | H | 0.41 ± 0.012 | 0.84 ± 0.095 | >50 |
| 4 | 6c | octadecyloxyethyl | benzyl | 0.22 ± 0.056 | 0.44 ± 0.085 | >50 |
| 5 | 15a | 1-O-tetradecyl-2-O-benzyl-sn-glyceryl | H | ±0.76 ± 0.34 | ±3.25 ± 2.18 | ±>50 |
| 6 | 15b | 1-O-hexadecyl-2-O-benzyl-sn-glyceryl | H | 0.56 ± 0.27 | 0.98 ± 0.38 | >50 |
| 7 | 15c | 1-O-hexadecyl-2-O-(3-F, 4-MeO—Bn)-sn-glyceryl | H | 0.36 ± 0.054 | 1.12 ± 0.10 | >50 |
| 8 | 15d | 1-O-octadecyl-2-O-benzyl-sn-glyceryl | H | 0.10 ± 0 | 0.28 ± 0.013 | 43.1 ± 18.9 |
| 9 | 15e | 1-O-octadecyl-2-O-benzyl-rac-glyceryl | H | 0.21 ± 0.004 | 0.35 ± 0.006 | 30.9 ± 7.7 |
| 10 | 15f | 1-O-octadecyl-2-O-octyl-sn-glyceryl | H | ±0.12 ± 0.057 | ±0.29 ± 0.058 | ±>50 |
| 11 | 15g | 1-O-octadecyl-2-O-(methylcyclohexyl)-sn-glyceryl | H | nd | nd | nd |
| 12 | 15h | 1-O-octadecyl-2-O-(3-F—Bn)-sn-glyceryl | H | 1.40 ± 0.058 | 2.80 ± 0.04 | 22.9 ± 0.1 |
| 13 | 15i | 1-O-octadecyl-2-O-(4-MeO—Bn)-sn-glyceryl | H | nd | nd | nd |
| 14 | 15j | 1-O-octadecyl-2-O-(3-F, 4-MeO—Bn)-sn-glyceryl | H | 0.074 ± 0.01 | 0.17 ± 0.014 | >50 |
| 15 | 15k | 1-O-octadecyl-2-O-methylpyridinyl-sn-glyceryl | H | nd | nd | nd |
| 16 | 15l | 1-O-oleyl-2-O-benzyl-sn-glyceryl | H | 0.13 ± 0.029 | 0.26 ± 0.0037 | >50 |
| 17 | 15m | 1-O-oleyl-2-O-(3-F, 4-MeO—Bn)-sn-glyceryl | H | 0.06 ± 0.014 | 0.11 ± 0.02 | >50 |
| 18 | 16 | 1-O-octadecyl-2-O-benzyl-sn-glyceryl | benzyl | 1.50 ± 0.93 | 4.27 ± 0.88 | >50 | nd = not determined;

The % inhibition was calculated as (Atv−Acv)/(Acd−Acv)×100% where Atv indicates the absorbance of the test compounds with virus infected cells and Acv and Acd indicate the absorbance of the virus control and the absorbance of the cell control, respectively. The average half-maximal effective concentration ($EC_{50}$) was defined as the concentration which achieved 50% inhibition of virus-induced cytopathic effects.

Example 6—SARS-CoV-2 Infection Assay

About 12e3 TMPRSS2-Vero cells or 20e3 Huh7.5 cells were seeded per well in black with clear flat bottom 96 well plates and incubated overnight. Compounds or controls were added about 30 to about 60 minutes prior to infection at the indicated concentrations with addition of SARS-CoV-2 at a multiplicity of infection (FFU/cell) equal to 0.01 for TMPRSS2-Vero and 0.1 for Huh7.5.

After incubation for 32 hours for TMPRSS2-Vero or 48 hours for Huh7.5 at 37° C. and 5% $CO_2$, the medium was removed and cells were incubated in 4% formaldehyde for 30 minutes at room temperature. Formaldehyde fixed cells were washed with PBS and permeabilized for immunofluorescence in 0.1% Triton-X 100 in PBS with 1% bovine serum albumin (BSA) fraction V (Millipore-Sigma) and stained for SARS-CoV-2 with a primary anti-Nucleocapsid antibody (GeneTex GTX135357) followed by AlexaFluor 594 secondary antibody (Thermo Fisher Scientific A-11012) with nuclear counterstain Sytox Green (Thermo Fisher Scientific).

Five images per well were obtained at 10× magnification using an Incucyte S3 (Sartorius). The percent infected cells and nuclei count were calculated using built-in image analysis tools for the Incucyte S3. Calculations for $EC_{50}$, $EC_{90}$ and $CC_{50}$ were carried out using the nonlinear regression analysis in GraphPad Prism 9 with the bottom and top parameters constrained to 0 and 100, respectively.

Effect of Compounds on SARS CoV-2 Replication in vitro

| | | | | Huh7.5 Cells | | | TMPRSS2-Vero Cells | | |
|---|---|---|---|---|---|---|---|---|---|
| Entry | Compd | $R_1$ | $R_2$ | $EC_{50}$ (µM) | $EC_{90}$ (µM) | $CC_{50}$ (µM) | $EC_{50}$ (µM) | $EC_{90}$ (µM) | $CC_{50}$ (µM) |
| 1 | 4a | eicosyl | H | 1.411 ± 0.089 | 4.746 ± 0.626 | >20 | 1.171 ± 0.060 | 2.185 ± 0.201 | >20 |
| 2 | 4b | hexadecyloxypropyl | H | 0.19[a] | 0.40[a] | >20 | nd | nd | nd |
| 3 | 4c | octadecyloxyethyl | H | 0.19[a] | 0.37[a] | >20 | nd | nd | nd |
| 4 | 6c | octadecyloxyethyl | benzy | nd | nd | nd | nd | nd | nd |
| 5 | 15a | 1-O-tetradecyl-2-O-benzyl-sn-glyceryl | H | 0.156 ± 0.008 | 0.493 ± 0.051 | >20 | 0.901 ± 0.022 | 1.694 ± 0.131 | >20 |
| 6 | 15b | 1-O-hexadecyl-2-O-benzyl-sn-glyceryl | H | 0.130 ± 0.020 | 0.309 ± 0.092 | >20 | 0.395 ± 0.021 | 0.810 ± 0.079 | >20 |
| 7 | 15c | 1-O-hexadecyl-2-O-(3-F, 4-MeO—Bn)-sn-glyceryl | H | 0.049 ± 0.005 | 0.113 ± 0.019 | >20 | 0.397 ± 0.026 | 0.869 ± 0.106 | >20 |
| 8 | 15d | 1-O-octadecyl-2-O-benzyl-sn-glyceryl | H | 0.138 ± 0.018 | 0.377 ± 0.098 | >20 | 0.205 ± 0.016 | 0.432 ± 0.075 | >20 |
| 9 | 15e | 1-O-octadecyl-2-O-benzyl-rac-glyceryl | H | 0.163 ± 0.026 | 0.514 ± 0.172 | >20 | 0.242 ± 0.020 | 0.642 ± 0.133 | >20 |
| 10 | 15f | 1-O-octadecyl-2-O-octyl-sn-glyceryl | H | 0.710 ± 0.028 | 1.713 ± 0.183 | >20 | 1.326 ± 0.052 | 2.349 ± 0.123 | >20 |
| 11 | 15g | 1-O-octadecyl-2-O-(methylcyclohexyl)-sn-glyceryl | H | nd | nd | nd | nd | nd | nd |
| 12 | 15h | 1-O-octadecyl-2-O-(3-F—Bn)-sn-glyceryl | H | 0.182 ± 0.018 | 0.444 ± 0.083 | >20 | 0.270 ± 0.016 | 0.629 ± 0.106 | >20 |
| 13 | 15i | 1-O-octadecyl-2-0-(4-MeO—Bn)-sn-glyceryl | H | nd | nd | nd | nd | nd | nd |
| 14 | 15j | 1-O-octadecyl-2-O-(3-F, 4-MeO—Bn)-sn-glyceryl | H | 0.056 ± 0.008 | 0.222 ± 0.070 | >20 | 0.174 ± 0.016 | 0.341 ± 0.044 | >20 |
| 15 | 15k | 1-O-octadecyl-2-O-methylpyridinyl-sn-glyceryl | H | nd | nd | nd | nd | nd | nd |
| 16 | 15l | 1-O-oleyl-2-O-benzyl-sn-glyceryl | H | 0.100 ± 0.010 | 0.246 ± 0.062 | >20 | 0.295 ± 0.013 | 0.568 ± 0.080 | >20 |
| 17 | 15m | 1-O-oleyl-2-O-(3-F, 4-MeO—Bn)-sn-glyceryl | H | 0.054 ± 0.006 | 0.102 ± 0.013 | >20 | 0.296 ± 0.019 | 0.524 ± 0.115 | >20 |
| 18 | 16 | 1-O-octadecyl-2-O-benzyl-sn-glyceryl | benzyl | 3.537 ± 0.583 | 16.44 ± 5.98 | >20 | 7.443 ± 0.818 | 15.263 ± 5.912 | >20 | nd = not determined; [a]Data from Example 7

Example 7—Antiviral Activity in Various Cell Types Infected with SARS-CoV-2

Vero E6, Caco-2, and Calu-3 cell lines were obtained from ATCC. Huh7.5 cells were obtained from Apath LLC. Calu-3 and Caco-2 cells were propagated in MEM (Corning), 10% FBS, Penicillin-Streptomycin (Gibco). Vero E6 and Huh7.5 cells were propagated in DMEM (Corning) with 10% FBS and Penicillin-Streptomycin (Gibco). Human PSC-lung cell generation, human lung organoids were generated as previously described (Leibel S L, McVicar R N, Winquist A M, Niles W D, Snyder E Y Generation of complete multi-cell type lung organoids from human embryonic and patient-specific induced pluripotent stem cells for infectious disease modeling and therapeutics validation Curr. Protoc. Stem Cell Biol., 54 (1) (2020 September), Article e118). H9 embryonic stem cells (WiCell) were cultured in feeder free conditions upon Matrigel (Corning #354230) coated plates in mTeSR medium (StemCellTech #85850). Media was changed daily, and stem cells were passaged using enzyme free dissociation reagent ReLeSR™ (Stem Cell Tech #05872). Cultures were maintained in an undifferentiated state, in a 5% CO2 incubator at 37° C.

For proximal lung organoid generation, human PSCs were dissociated into single cells, and then seeded on Matrigel-coated plates (BD Biosciences) at a density of $5.3 \times 10^4$ cells/cm$^2$ in Definitive Endoderm (DE) induction medium (RPMI1640, 2% B27 supplement, 1% HEPES, 1% glutamax, 50 U/mL penicillin/streptomycin), supplemented with 100 ng/mL human activin A (R&D), 5 µM CHIR99021 (Stemgent), and 10 µM ROCK inhibitor, Y-27632 (R&D Systems) on day 1. On days 2 and 3 cells were cultured in DE induction media with only 100 ng/mL human activin A. Anterior Foregut Endoderm (AFE) was generated by supplementing serum free basal medium (3 parts IMDM:1 part F12, B27+N2 supplements, 50 U/mL penicillin/streptomycin, 0.25% BSA, 0.05 mg/mL L-ascorbic acid, 0.4 mM monothioglycerol) with 10 µM SB431542 (R&D) and 2 µM Dorsomorphin (StemGent) on days 4-6. On day 7, AFE medium was changed to Lung Progenitor Cell (LPC) induction medium, containing serum free basal medium supplemented with 10 ng/mL human recombinant BMP4 (R&D), 0.1 µM all-trans retinoic acid (Sigma-Aldrich) and 3 µM CHIR99021. Media was changed every other day for 9-11 days. To generate 3D human proximal lung organoids, we modified a previously published protocol (K. B. McCauley, F. Hawkins, M. Serra, D. C. Thomas, A. Jacob, and D. N. Kotton. (2017) Efficient Derivation of Functional Human Airway Epithelium from Pluripotent Stem Cells via Temporal Regulation of Wnt Signaling. *Cell Stem Cell;* 20(6): 844-857)

LPCs were dissociated in accutase for 10 minutes and resuspended in Matrigel in a 12-well, 0.4 µm pore size Transwell (Corning) culture insert at $5.0 \times 10^4$ cells/200 ul of Matrigel. Cells were cultured in proximal lung organoid maturation media using serum free basal medium supplemented with 250 ng/mL FGF2, 100 ng/mL rhFGF10, 50 nM dexamethasone (Dex), 100 µM 8-Bromoadenosine 3',5'-cyclic monophosphate sodium salt (Br-cAMP), 100 µM 3-Isobutyl-1-methylxanthine (IBMX) and 10 µM ROCK inhibitor (Y-27632). Proximal lung organoid media was changed every other day for 3 weeks. Human PSC-derived lung organoids were dissociated into single cells and seeded at 20,000 cells per well of a matrigel coated 96-well plate one day before transfection. Transwells containing the proximal organoids in matrigel were incubated in 2 U/ml dispase for 30 minutes at 37° C. Cold PBS was added to the mixture then centrifuged at 400×g for 5 mins.

Supernatant was carefully removed and resuspended in 2-3 mls of TrypLE Express (Gibco #12605010) for 20 minutes at 37° C. Reaction was quenched with 2% FBS in DMEM/F12 then centrifuged at 400×g for 5 min. The supernatant was aspirated, and the cell pellet resuspended in 1 ml of quenching media supplemented with 10 µM Rock inhibitor (Y-27632). Cell count was performed and the respective volume of cells were transferred into a reagent reservoir trough and resuspended in proximal lung organoid maturation media and plated via multichannel pipette into 96 well plates at 100 ul per well as monolayers.

SARS-CoV-2 infection: SARS-CoV-2 isolate USA-WA1/2020 (BEI Resources) was propagated and infectious units quantified by plaque assay using Vero E6 (ATCC) cells. Approximately 12,000 cells from each cell line were seeded per well in a 96 well plate. Vero E6 and Huh7.5 were seeded approximately 24 h prior to treatment/infection. Calu-3 and Caco-2 were seeded approximately 48 h prior to treatment/infection. Human PSC lung cell infections and cytotoxicity experiments were performed when cells reached 100% confluency. Compounds or controls were added at the indicated concentrations 30 minutes prior to infection followed by the addition of SARS-CoV-2 at a multiplicity of infection equal to 0.01. After incubation for 48 hours at 37° C. and 5% $CO_2$, cells were washed twice with PBS and lysed in 200 ul TRIzol (ThermoFisher). All work with SARS-CoV-2 was conducted in Biosafety Level 3 conditions at the University of California San Diego with approval from the Institutional Biosafety Committee.

RNA extraction, cDNA synthesis and qPCR: RNA was purified from TRIzol lysates using Direct-zol RNA Microprep kits (Zymo Research) according to manufacturer recommendations that included DNase treatment. RNA was converted to cDNA using the iScript cDNA synthesis kit (BioRad) and qPCR was performed using iTaq universal SYBR green supermix (BioRad) and an ABI 7300 real-time pcr system. cDNA was amplified using the following primers RPLP0 F—GTGTTCGACAATGGCAGCAT; RPLP0 R—GACACCCTCCAGGAAGCGA; SARS-CoV-2 Spike F—CCTACTAAATTAAATGATCTCTGCTTTACT; SARS-CoV-2 Spike R—CAAGCTATAACGCAGCCTGTA. Relative expression of SARS-CoV-2 Spike RNA was calculated by delta-delta-Ct by first normalizing to the housekeeping gene RPLP0 and then comparing to SARS-CoV-2 infected Vero E6 cells that were untreated (reference control). Curves were fit using the nonlinear regression—log(inhibitor) vs. response (four parameter) model using Prism 9. To calculate effective concentrations $EC_{50}$ and $EC_{90}$ values, qRT-PCR values were normalized to percent inhibition and curves fit using the nonlinear regression—log(agonist) vs. response (four parameter) model with bottom and top constrained to 0 and 100 respectively using Prism 9.

Cell viability assay: Cell type were seeded as per SARS-CoV-2 infection studies in opaque walled 96-well cell culture plates or 229E infection studies in clear 96-well cell culture plates and incubated overnight. Compounds or controls were added at the indicated concentrations. For SARS-CoV-2 related studies, cells were incubated for 48.5 hours at 37° C. and 5% $CO_2$, an equal volume of CellTiter-Glo reagent (Cat. #G7570, Promega, Madison, WI) was added, mixed and luminescence recorded on a Veritas Microplate Luminometer (Turner BioSystems) according to manufacturer recommendations. For 229E related, cells were incubated for 72 hours at 37° C. and 5% $CO_2$, supernatants removed, 50p of serum-free media and 50p of MTT Reagent (Abcam ab211091) added to each well and incubated for 3 hrs at 37° C. Absorbance was measured on an ELx800, Universal Microplate reader, (BIO-TEK Instruments, INC) according to manufacturer recommendations. Percent viability was calculated compared to untreated controls and $CC_{50}$ values were calculated using Prism 9.

| Antiviral Activity, Cytotoxicity and Selectivity of the Compounds | | | | | |
|---|---|---|---|---|---|
| Compound | $EC_{50}$ (μM) | $EC_{90}$ (μM) | $CC_{50}$ (μM) | Selectivity | p value $EC_{50}$ VS RDV, RVn |
| Vero E6 cells | | | | | |
| RDV | 1.13 | 7.05 | 101 | 89.4 | — |
| RVn | 0.38 | 0.77 | >100 | >263 | — |
| HDP-P-RVn, 4b | 0.63 | 0.73 | >100 | >158 | NS |
| ODE-P-RVn, 4c | 0.30 | 0.33 | >100 | >333 | NS |
| ODBG-P-RVn, 15d | 0.14 | 0.16 | 97.9 | 699 | 0.010, 0.311 |
| PSC-human lung cells | | | | | |
| RDV | 0.14 | 0.23 | 32.7 * | 234 | — |
| RVn | 0.74 | 2.62 | >100 * | >135 | — |
| HDP-P-RVn * | 0.35 | 0.94 | ND | — | — |
| ODE-P-RVn | 0.22 | 0.70 | >100 * | >454 | 0.791, 0.006 |
| ODBG-P-RVn | 0.15 | 0.26 | 61.5 * | 410 | >0.999, 0.002 |
| Calu-3 cells | | | | | |
| RDV | 0.23 | 0.31 | >100 | >434 | — |
| RVn | 0.15 | 0.18 | >100 | >666 | — |
| ODE-P-RVn | 0.34 | 0.64 | 98.7 | 290 | NS |
| ODBG-P-RVn | 0.30 | 0.33 | 98.2 | 327 | NS |
| Huh7.5 cells | | | | | |
| RDV | 0.06 | 0.12 | 15.2 | 253 | — |
| RVn | 0.32 | 0.73 | >100 | >312 | — |
| HDP-P-RVn | 0.19 | 0.40 | >100 | >526 | NS |
| ODE-P-RVn | 0.19 | 0.37 | >100 | >526 | NS |
| ODBG-P-RVn | 0.14 | 0.15 | 62.9 | 449 | NS |
| Caco-2 cells | | | | | |
| RDV | 0.17 | 0.28 | >100 | >588 | — |
| RVn | 0.96 | 1.75 | >100 | >104 | — |
| ODE-P-RVn | 0.77 | 1.25 | >100 | >129 | 0.007, 0.971 |
| ODBG-P-RVn | 0.30 | 0.33 | 88.4 | 295 | 0.968, 0.007 |

Abbreviations:
RDV, Remdesivir (GS-5734);
RVn, Remdesivir nucleoside (GS-441524);
HDP-P-, hexadecyloxypropyl-P-;
ODE-P-, octadecyloxyethyl-P-;
ODBG-P-, 1-O-octadecyl-2-O-benzyl-glycero-3-P-;
$EC_{50}$: half-maximal effective concentration;
$CC_{50}$: 50% cytotoxic concentration, Selectivity index,
$CC_{50}/EC_{50}$; statistical analysis comparing $LogEC_{50}$ values from separate experiments by one-way ANOVA.
$CC_{50}$ results by CellTiter-Glo.
All experiments performed three times in duplicate except starred * were done twice in duplicate.

In all cell lines, there was a dose-dependent inhibition of viral RNA by ODBG-P-RVn, ODE-P-RVn, HDP-P-RVn, remdesivir (RDV) and remdesivir nucleoside (RVn). In Vero E6 cells, the average half-maximal effective concentration ($EC_{50}$) and average 90% effective concentration ($EC_{90}$) of ODBG-P-RVn was 0.14 μM and 0.16 μM, respectively. The $EC_{50}$ of ODBG-P-RVn in Vero E6 cells was significantly lower than RDV. ODE-P-RVn and HDP-P-RVn were also potently antiviral with $EC_{50}$ values of 0.3 μM and 0.63 μM in Vero E6. The $EC_{50}$ of ODBG-P-RVn and ODE-P-RVn were less than 0.35 μM in PSC-lung and Calu-3, both models of human lung infection. The antiviral activities of ODBG-P-RVn and ODE-P-RVn were significantly better than RVn in PSC-lung cells. ODBG-P-RVn, ODE-P-RVn and HDP-P-RVn demonstrated strong antiviral activity in Huh7.5 cells with $EC_{50}$ less than 0.2 μM that was not significantly different from RDV or RVn. In the Caco-2 cell line, the $EC_{50}$ of ODBG-P-RVn was 0.3 μM which was significantly lower than RVn but similar to RDV. In the same cell line, the $EC_{50}$ of ODE-P-RVn was 0.77 μM, which was significantly higher than RDV.

The cytotoxicity of each compound by incubating each of these cell lines with serial dilutions of each compound from 1.23 μM to 100 μM for 48 hours. The average 50% cytotoxic concentrations ($CC_{50}$) for all compounds were greater than 60 μM in all cell lines except for RDV which had a $CC_{50}$ of 32.7 μM in PSC-lung cells and 15.2 μM in Huh7.5, a human hepatocyte cell line. The selectivity index of ODBG-P-RV ranged from 295 to 699 in the five cell types tested in this example). The range of antiviral activity and cytotoxicity of ODBG-P-RVn ($EC_{50}$ 0.14 μM-0.30 μM and $CC_{50}$ 61.5 μM-98.2 μM) was more consistent across cell types than RDV ($EC_{50}$ 0.06 μM-1.13 μM and $CC_{50}$ 15.2 μM->100 μM) (Table 1). Collectively, these data demonstrate that lipid RVn monophosphate prodrugs are potent antivirals against SARS-CoV-2 in vitro with low toxicity and excellent selectivity indexes.

Example 8—Effect of Antivirals in Human Coronavirus 229E Infected Cells

Human Coronavirus 229E (ATCC) was propagated and infectious units quantified by $TCID_{50}$ using MRC-5 cells. For antiviral testing, approximately $10^4$ MRC-5 cells were seeded per well in EMEM (10% FCS) at 37 C in a 96 well plate overnight. Medium from each well was removed and cells were infected with 100 $TCID_{50}$ virus in 100 μL medium for two hours.

Cells were washed one time with medium and then compounds or controls added at the indicated concentrations. After three days, CPE was observed under microscope and quantified using an MTT cell proliferation assay kit (Abcam) read on an ELx800, Universal Microplate reader (BIO-TEK Instruments, INC). The % Inhibition was calculated as $(A_{tv}-A_{cv})/(A_{cd}-A_{cv})\times 100\%$ where $A_{tv}$ indicates the absorbance of the test compounds with virus infected cells and A, and Aca indicate the absorbance of the virus control and the absorbance of the cell control, respectively. The average half-maximal effective concentration ($EC_{50}$) was defined as the concentration which achieved 50% inhibition of virus-induced cytopathic effects.

Figure 4A:
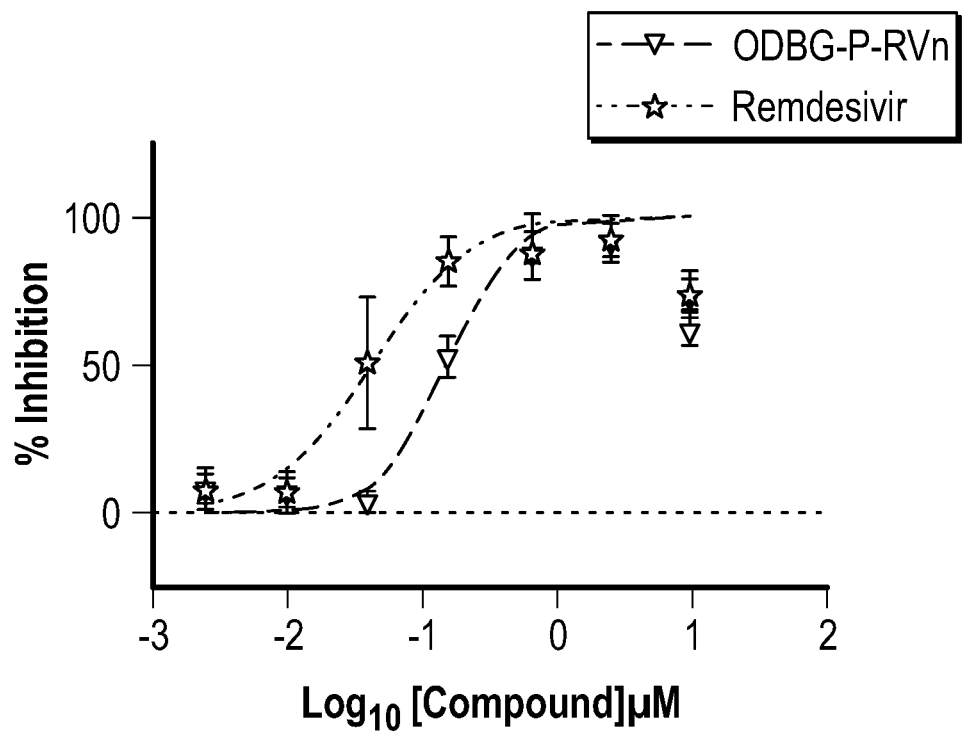
FIG. 4A depicts antiviral dose response curves for remdesivir (GS-5734) and an embodiment of a compound herein against the human coronavirus 229E in MRC-5 cells.
Figure 4B:
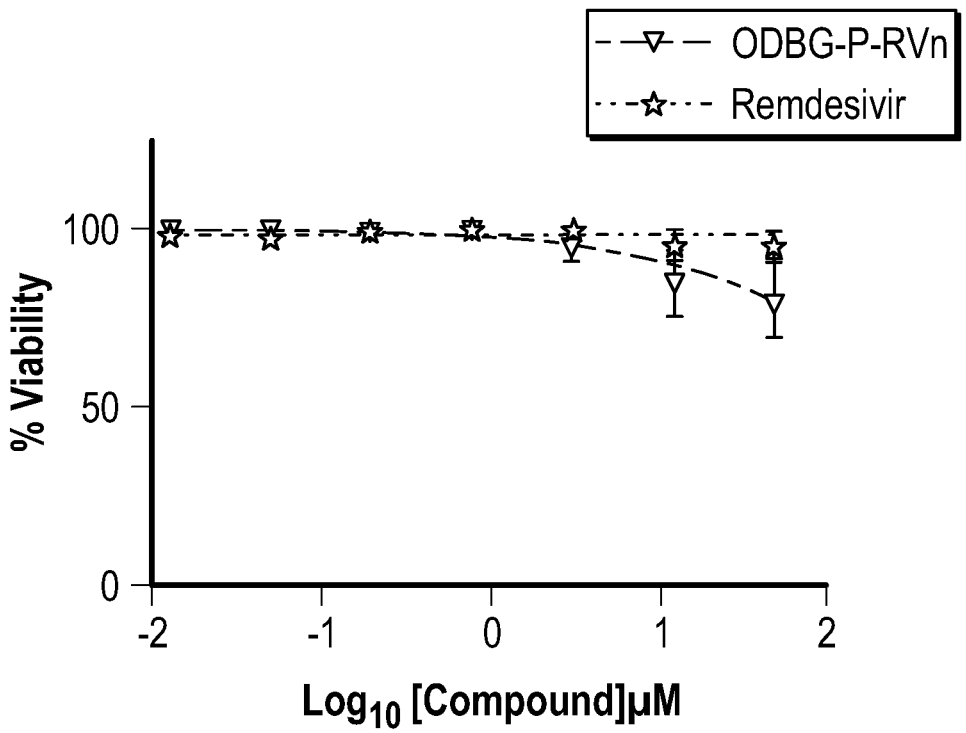
FIG. 4B depicts the cytotoxicity in MRC-5 cells incubated in the presence of the indicated drug and an embodiment of a compound herein at the indicated concentration for 72 hours.

FIG. 4A and FIG. 4B: ODBG-P-RVn (15d) inhibits the human Alphacoronavirus 229E. FIG. 4A depicts antiviral dose response curves for remdesivir (GS-5734) and ODBG-P-RVn against the human coronavirus 229E in MRC-5 cells. Cells were infected with 229E for 2 hours followed by treatment with the indicated dose of the indicated drug for 72 hours. The relative CPE was determined by measuring cell viability using an MTT assay.

FIG. 4B depicts the cytotoxicity in MRC-5 cells incubated in the presence of the indicated drug at the indicated concentration for 72 hours, after which cell viability was measured by the CellTiter-Glo assay. Data points indicate the averages from 3 independent experiments performed in duplicate. Error bars represent the standard error mean (SEM).

Both ODBG-P-RVn and RDV demonstrated a dose-dependent inhibition of cytopathic effect (CPE). The $EC_{50}$ values of ODBG-P-RVn and RDV were 0.15 µM and 0.04 µM and the $EC_{90}$s were 0.54 mM and 0.26 mM respectively. The $CC_{50}$ for ODBG-P-RVn and RDV were greater than 50 µM in MRC-5 cells. Together with the antiviral data for SARS-CoV-2, this demonstrates that ODBG-P-RVn has antiviral activity against two genetically distinct human pathogenic coronaviruses.

Example 9—Orally Administered ODBG-P-RVn (15d) Achieves Therapeutic Plasma Levels in Syrian Hamsters ODBG-P-RVn in 0.1M sodium carbonate/bicarbonate buffer, pH 9.0, was administered to Syrian Hamsters by oral gavage every 12 hours for seven days. ODBG-P-RVn was present as the sodium salt. It was well tolerated, and no adverse clinical signs were noted. Peak plasma levels of ODBG-P-RVn were noted at 1 hour and fell by 50% in about 5 hours.

Plasma curves were generally similar at day 1 and 7 except at 16.9 mg/kg, the 7 day values were slightly higher than the levels at day 1. At 12 hours ODBG-P-RVn levels were above the $EC_{90}$ for ODBG-P-RVn in all cell lines studied including Vero E6 cells and PSC lung cells on both day 1 and 7. Levels of the RVn, the nucleoside metabolite of ODBG-P-RVn peaked at 3 hours after administration and declined thereafter. Plasma levels of RVn were less than the $EC_{90}$ for RVn in both PSC lung cells and Vero E6 cells. The observed low levels or RVn suggest that antiviral activity attributable to this metabolite will be minimal and are also consistent with finding of OBDG-P-RVn stability in human plasma. Collectively, these results suggest that ODBG-P-RVn will be effective in suppressing viral replication in a variety of tissue types in vivo.

Figure 5A:
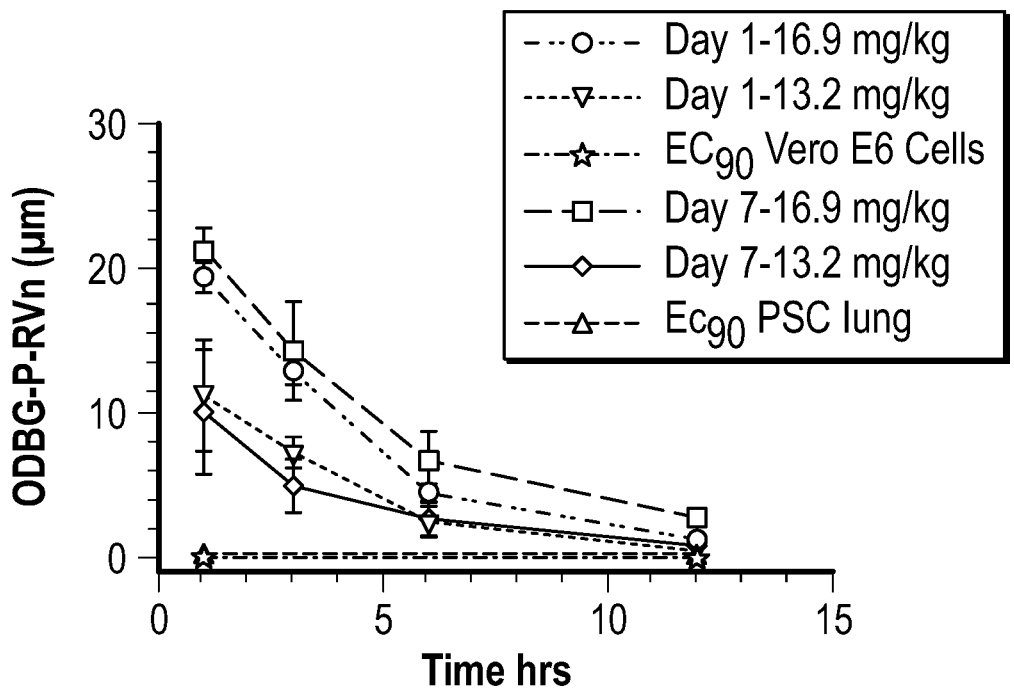
FIG. 5A depicts the seven day oral pharmacokinetics in syrian hamsters for an embodiment of a compound herein.
Figure 5B:
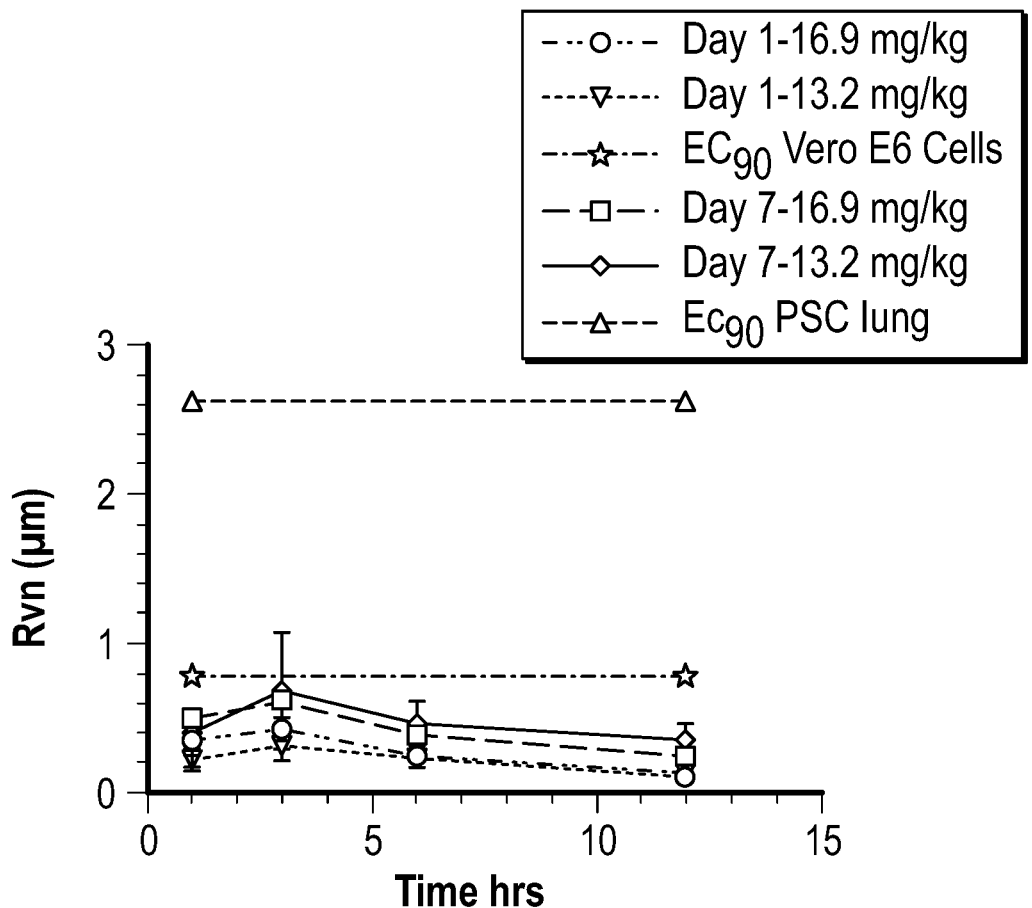
FIG. 5B depicts the seven day oral pharmacokinetics in syrian hamsters for remdesivir.

FIG. 5A and FIG. 5B depict the seven day oral pharmacokinetics in Syrian hamsters. Syrian hamsters were given vehicle or ODBG-P-RVn by oral gavage every 12 hours for 7 days. Groups of 3 animals received vehicle or drug at doses of 16.9 and 13.2 mg/kg. Animals were weighed daily and monitored for clinical signs. Plasma samples were obtained at 1, 3, 6 and 12 hours on day 1 and day 7 and frozen for analysis of (FIG. 5A) ODBG-P-RVn and (FIG. 5B) RVn by LC/MS/MS.

Analytical Methods: ODBG-P-RVn: Hamster plasma samples (10 µL) containing ODBG-P-RVn and $K_2$EDTA as the anticoagulant were added to polypropylene tubes containing water (100 µL), internal standard solution (10 µL; 1,000 ng/mL of ODE-P-RVn in ACN:DMF (1:1, v/v)), and 10 µL of ACN:DMF (1:1, v/v). The solutions were mixed, then acidified with phosphoric acid, 85% w/v:water (1:19, v/v; 10 µL), mixed, then diluted with 200 µL of IPA, mixed, then diluted with 500 µL of water, and mixed. The samples were extracted with a Sep-Pak® tC18 96-well solid phase extraction plate (25 mg; Waters, Milford, MA). Extraction occurred under positive pressure conditions using nitrogen. Samples were washed serially with 1 mL of water:acetonitrile:formic acid (475:25:0.5, v/v/v) and 0.4 mL of water:acetonitrile:formic acid (350:150:0.5, v/v/v) before being serially eluted with 100 µL and 150 µL of water:{acetonitrile:isopropyl alcohol (1:1, v/v)}:formic acid:ammonium formate:citric acid solution, 2% w/v (15:85:0.1:0.1:0.1, v/v/v/w/v). The citric acid solution was prepared as water:citric acid monohydrate (20:0.4, v/w). After elution, 100 µL of water was added to each sample. The ODBG-P-RVn extracts were analyzed using an Agilent 1200 HPLC system (Agilent, Santa Clara, CA) coupled to an API5500 mass analyzer (SCIEX, Foster City, CA). Analytes were chromatographically separated using a Dacapo DX-$C_{18}$ MF column (100×2 mm, 2.5 µm; ImtaktUSA, Portland, OR) using a mobile phase system consisting of Mobile Phase A (water:formic acid:[water:ammonium formate:citric acid (25:5:0.5, v/w/w)] (1,000:1:1, v/v/v) and Mobile Phase B (acetonitrile:isopropyl alcohol:formic acid:[water:ammonium formate:citric acid (25:5:0.5, v/w/w)] (800:200:1:1, v/v/v/v). The total analytical run time was 4.5 minutes. The mobile phase was nebulized using heated nitrogen in a Turbo-V source/interface set to electrospray positive ionization mode. The ionized compounds were detected using multiple reaction monitoring with transitions m/z 788.4>229 (V2043) and 668.4>467.2 (V2041). This method is applicable for measuring ODBG-P-RVn concentrations ranging from 6.25 to 3,000 ng/mL using 10.0 µL of plasma for extraction. The peak areas of ODBG-P-RVn and RVn were acquired using Analyst v. 1.6.2 (SCIEX, Framingham, MA). The calibration curve was obtained by fitting the peak area ratios of the analyte/I.S. and the standard concentrations to a linear equation with 1/x2 weighting, using Analyst. The equation of the calibration curve was then used to interpolate the concentrations of the analyte in the samples using their peak area ratios. The peak areas used for the calculations were not rounded.

Analytical Methods: RVn (GS-441524): Hamster plasma samples (20 µL) containing GS-441524 and $K_2$EDTA as the anticoagulant were added to Eppendorf LoBind microfuge tubes containing acetonitrile (300 µL) and water:acetonitrile (2:8, v/v; 60 µL). The solutions were mixed and centrifuged at 16,000 g for five minutes. The supernatant (300 µL) was then filtered through an Ostro protein precipitation and phospholipid removal plate (25 mg; Waters, Milford, MA). Filtration occurred under positive pressure conditions using nitrogen. Collected filtered samples were capped, mixed and stored at 10° C. pending analysis. The GS-441524 extracts were analyzed using an Acquity UPLC system (Waters, Milford, MA) coupled to a G2-S QTof mass analyzer (Waters, Milford, MA). Analytes were chromatographically separated using a Unison-UK Amino HT column (100×2 mm, 3 µm; ImtaktUSA, Portland, OR) using a mobile phase system consisting of Mobile Phase A (0.008% ammonium hydroxide, 0.012% acetic acid in water, v/v/v) and Mobile Phase B (0.008% ammonium hydroxide, 0.012% acetic acid in acetonitrile, v/v/v). The total analytical run time was 12.5 minutes. The mobile phase was nebulized using heated nitrogen in a Z-spray source/interface set to electrospray positive ionization mode. The ionized compounds were detected using Tof MS scan monitoring in sensitivity mode scanning from 50.0 to 700 m/z. This method is applicable for measuring GS-441524 concentrations ranging from 1.00 to 1,000 ng/mL using 20.0 UL of plasma for extraction. The peak areas of GS-441524 were acquired using MassLynx V4.2 (Waters, Milford, MA). The calibration curve was obtained by fitting the peak area ratios of the analyte and the standard concentrations to a linear equation with $1/x^2$ weighting using MassLynx. The equation of the calibration curve was then used to interpolate the concentrations of the analyte in the samples using their peak areas. The peak areas used for the calculations were not rounded.

Example 10—Stability of ODE-P-RVn (4c) and ODBG-P-RVn (15d) in Human Plasma

One of the disadvantages of remdesivir is instability in plasma where it has been reported to persist at virologically significant levels for less than 2 hours after intravenous infusion. (1, 2). Remdesivir also has limited stability ex vivo in human plasma with a reported $T_{1/2}$ of 69 minutes (Siegel D, Hui H C, Doerffler E, Clarke M O, Chun K, Zhang L, Neville S, Carra E, Lew W, Ross B, Wang Q, Wolfe L, Jordan R, Soloveva V, Knox J, Perry J, Perron M, Stray K M, Barauskas O, Feng J Y, Xu Y, Lee G, Rheingold A L, Ray A S, Bannister R, Strickley R, Swaminathan S, Lee W A, Bavari S, Cihlar T, Lo M K, Warren T K, Mackman R L. Discovery and Synthesis of a Phosphoramidate Prodrug of a Pyrrolo[2,1-f][triazin-4-amino] Adenine C-Nucleoside (GS-5734) for the Treatment of Ebola and Emerging Viruses. *J Med Chem* 2017 Mar. 9; 60(5):1648-1661).

The stability of ODE-P-RVn and ODBG-P-RVn in human plasma was evaluated with either $K_2$EDTA or sodium heparin as an anticoagulant.

Figure 6A:
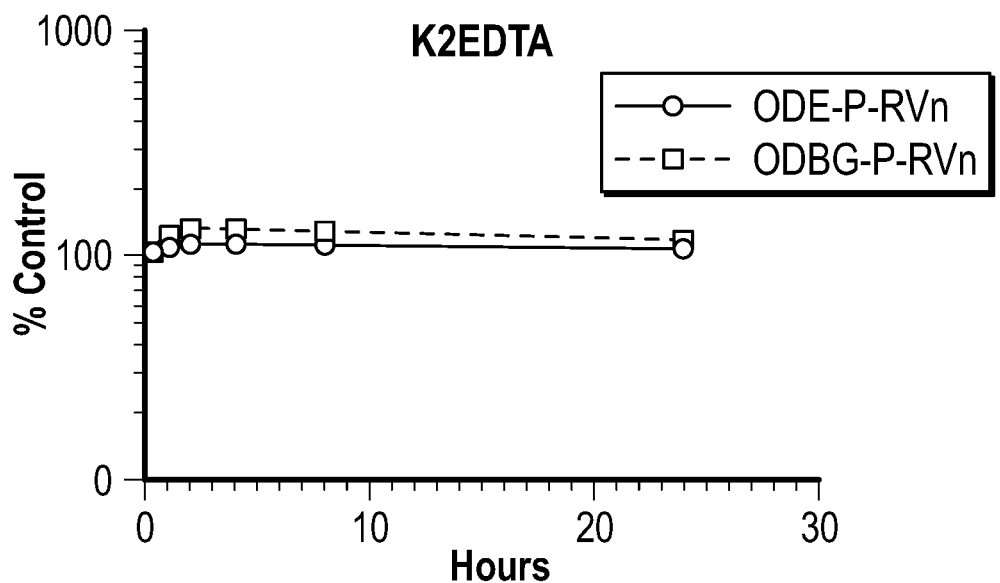
FIG. 6A depicts the stability of ODE-P-RVn and ODBG-P-RVn in human plasma with $K_2$EDTA as an anticoagulant.
Figure 6B:
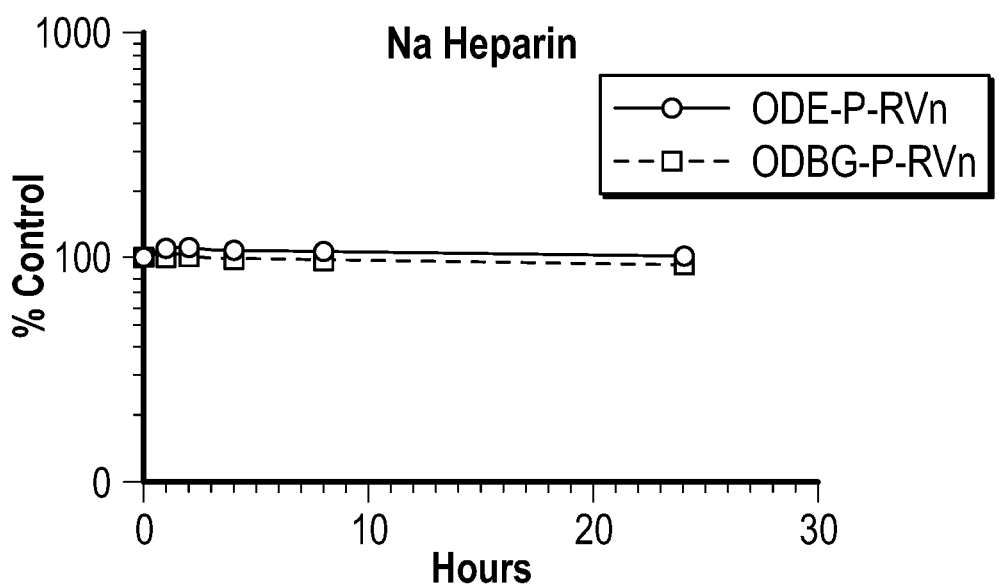
FIG. 6B depicts the stability of ODE-P-RVn and ODBG-P-RVn in human plasma with sodium heparin as an anticoagulant.

Plasma was spiked with 2 micrograms/ml concentrations of ODE-P-RVn or ODBG-P-RVn and incubated at 37° C. Samples were taken at 0.5, 1, 2, 4, 8 and 24 hours and frozen for later analysis by LC/MS/MS by the method shown in Example C. FIG. 6A and FIG. 6B shows that both ODE-P-RVn and ODBG-P-RVn were stable for at least 24 hours in human plasma with either $K_2$EDTA (FIG. 6A) or sodium heparin (FIG. 6B) as anticoagulants. (See, e.g., Warren T. K. et al. Nature. 2016 Mar. 17; 531(7594):381-5; and Tempestilli, M. et al. J. Antimicrob Chemother. 2020 Oct. 1; 75(10):2977-2980).

The invention claimed is:
1. A compound of formula (I):

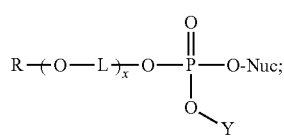

formula (I)

wherein—
Nuc is selected from the group consisting of beta-D-N4-hydroxycytidine (NHC), (2'R)-2-amino-2'-deoxy-2'-fluoro-N,2'-dimethyladenosine, and GS-441524:

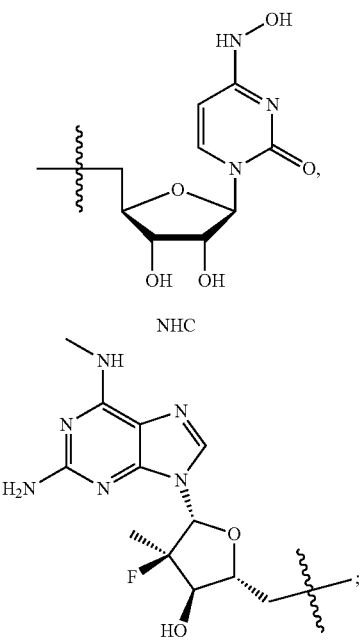

NHC (2'R)-2-amino-2'-deoxy-2'-fluoro-N,2'-dimethyladenosine

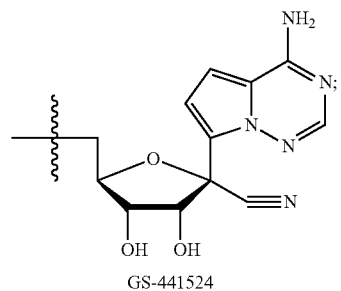

GS-441524

Y is independently selected from the group consisting of hydrogen, a $C_1$-$C_{30}$ hydrocarbyl, a pharmaceutically acceptable cation, and a covalent bond to a carbon atom of a five-carbon sugar moiety of the antiviral nucleoside or the antiviral nucleoside analog;
x is 0 or 1;
L is a $C_1$-$C_6$ hydrocarbyl; and
R is independently selected from the group consisting of a $C_{10}$-$C_{30}$ hydrocarbyl and a substituent of formula (A);

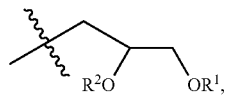

formula (A)

wherein $R^1$ and $R^2$ are independently selected from the group consisting of hydrogen and a $C_1$-$C_{30}$ hydrocarbyl.

2. The compound of claim 1, wherein Y is (i) an unsubstituted $C_1$-$C_6$ alkyl, (ii) Na$^+$, or (iii) a covalent bond to a 3'-carbon of the five carbon sugar moiety.

3. The compound of claim 1, wherein Y comprises at least one cyclic moiety.

4. The compound of claim 3, wherein Y is selected from the group consisting of aryl, arylalkyl, heteroaryl, heteroarylalkyl, and heterocycloalkyl, each of which is unsubstituted or substituted.

5. The compound of claim 4, wherein the heteroaryl is an unsubstituted or substituted pyridinyl.

6. The compound of claim 4, wherein the arylalkyl is an unsubstituted or substituted benzyl.

7. The compound of claim 6, wherein the unsubstituted or substituted benzyl has a structure according to formula (B):

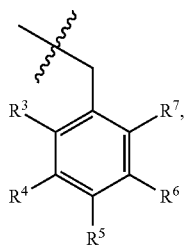

formula (B)

wherein $R^3$, $R^4$, $R^5$, $R^6$, and $R^7$ are independently selected from the group consisting of hydrogen, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino, and di-substituted amino.

8. The compound of claim 7, wherein at least two of $R^3$, $R^4$, $R^5$, $R^6$, and $R^7$ are hydrogen.

9. The compound of claim 1, wherein R (i) is an unsubstituted or substituted $C_{12}$-$C_{24}$ hydrocarbyl, (ii) comprises 0 to 6 unsaturated bonds, (iii) comprises a cyclopropyl moiety, or (iv) a combination thereof.

10. The compound of claim 1, wherein R (i) is an unsubstituted or substituted $C_{13}$-$C_{29}$ heteroalkyl, (ii) comprises 0 to 6 unsaturated bonds, or (iii) a combination thereof.

11. The compound of claim 1, wherein R is selected from the group consisting of—

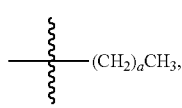

(i)

wherein a is 1 to 29; and

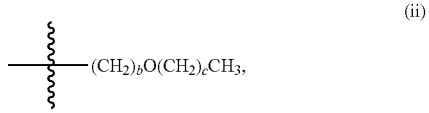

(ii)

wherein b is 1 to 29, c is 0 to 28, and a sum of b and c is 29 or less.

12. The compound of claim 11, wherein (i) a is 15 to 25, or (ii) b is 1 to 4 and c is 15 to 20.

13. The compound of claim 11, wherein (i) a is 19, (ii) b is 3 and c is 15, or (iii) b is 2 and c is 17.

14. The compound of claim 11, wherein a is 8.

15. The compound of claim 1, wherein $R^1$ (i) is an unsubstituted or substituted $C_{12}$-$C_{24}$ hydrocarbyl, (ii) comprises 0 to 6 unsaturated bonds, or (iii) a combination thereof.

16. The compound of claim 1, wherein (i) $R^1$, (ii) $R^2$, or (iii) both $R^1$ and $R^2$ are independently selected from a $C_1$-$C_{30}$ hydrocarbyl comprising at least one cyclic moiety.

17. The compound of claim 16, wherein (i) $R^1$, (ii) $R^2$, or (iii) both $R^1$ and $R^2$ are independently selected from the group consisting of aryl, arylalkyl, heteroaryl, heteroarylalkyl, and heterocycloalkyl, each of which is unsubstituted or substituted.

18. The compound of claim 17, wherein the arylalkyl is an unsubstituted or substituted benzyl.

19. The compound of claim 18, wherein the unsubstituted or substituted benzyl has a structure according to formula (C):

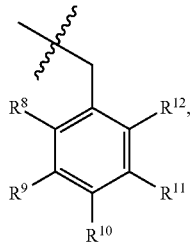

formula (C)

wherein $R^8$, $R^9$, $R^{10}$, $R^{11}$, and $R^{12}$ are independently selected from the group consisting of hydrogen, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino, and di-substituted amino.

20. The compound of claim 19, wherein at least two of $R^8$, $R^9$, $R^{10}$, $R^{11}$, and $R^{12}$ are hydrogen.

21. The compound of claim 1, wherein the substituent of formula (A) is a racemate, an sn-1 stereoisomer, or an sn-3 stereoisomer.

22. The compound of claim 1, wherein—

(i) $R^1$ is selected from the group consisting of—

(a) 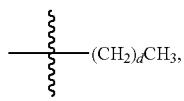

wherein d is 1 to 29; and (b) 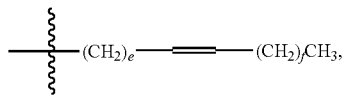

wherein e is 1 to 27, f is 0 to 26, and a sum of e and f is 27 or less;

(ii) $R^2$ is selected from the group consisting of—

(A) 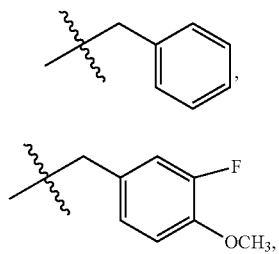

(B)

(C)

(D) 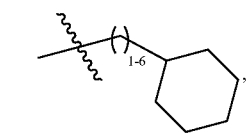

(E) 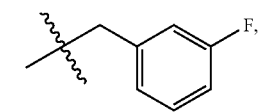

(F) 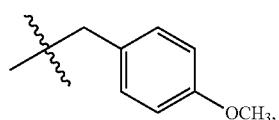, and (G) 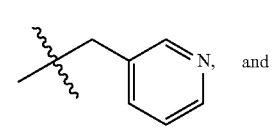

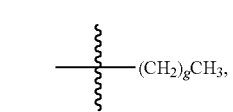

wherein g is 1 to 29; or (iii) a combination thereof.

23. The compound of claim 22, wherein g is 2 to 7.

24. The compound of claim 1, wherein x is 1, and L is an unsubstituted or substituted $C_1$-$C_3$ hydrocarbyl.

25. The compound of claim 24, wherein L is selected from the group consisting of an unsubstituted methylene, an unsubstituted ethylene, and an unsubstituted propylene.

26. The compound of claim 1, wherein the compound is one of the following:

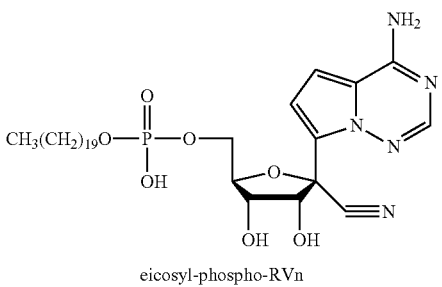

eicosyl-phospho-RVn

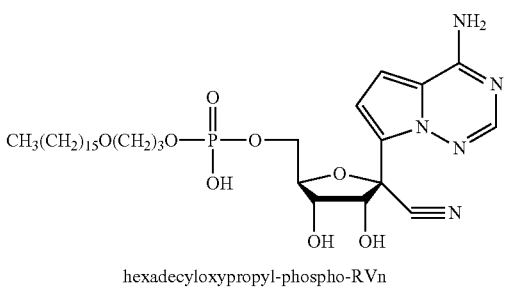

hexadecyloxypropyl-phospho-RVn

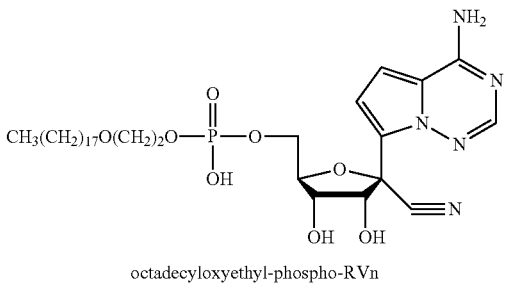

octadecyloxyethyl-phospho-RVn

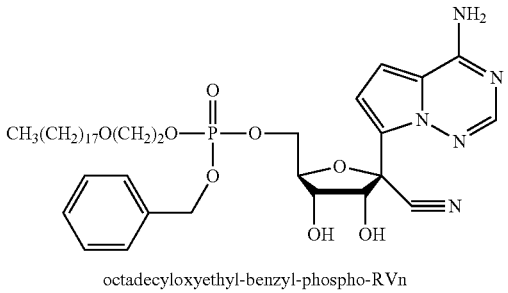

octadecyloxyethyl-benzyl-phospho-RVn

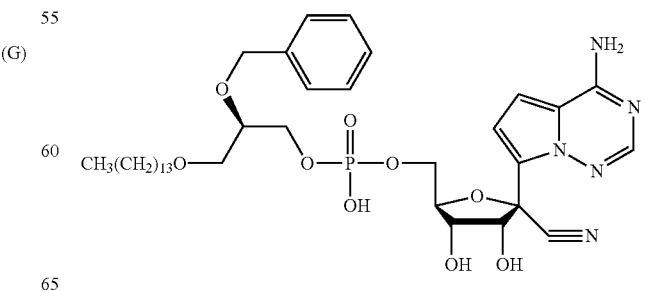

1-O-tetradecyl-2-O-benzyl-sn-glyceryl-phospho-RVn

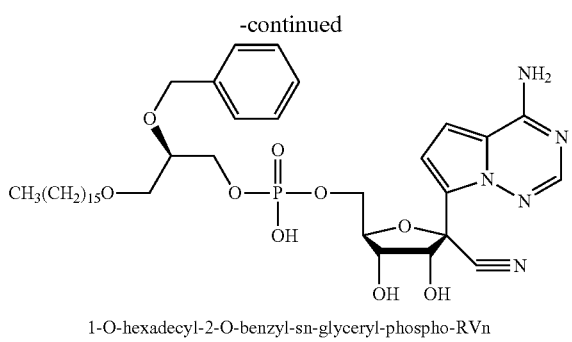

1-O-hexadecyl-2-O-benzyl-sn-glyceryl-phospho-RVn

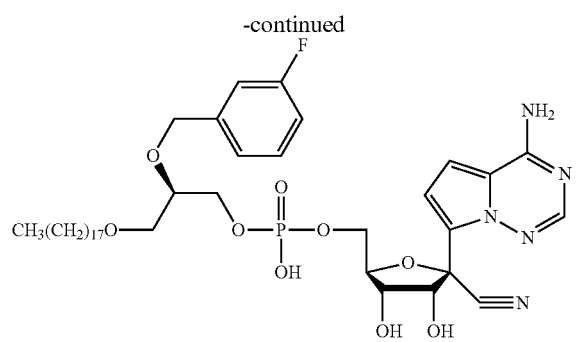

1-O-octadecyl-2-O-(3-fluorobenzyl)-sn-glyceryl-phospho-RVn

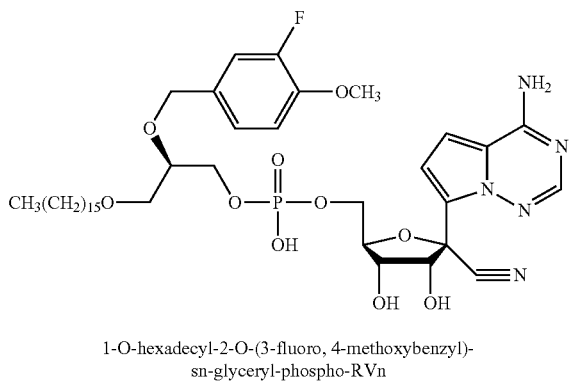

1-O-hexadecyl-2-O-(3-fluoro, 4-methoxybenzyl)-sn-glyceryl-phospho-RVn

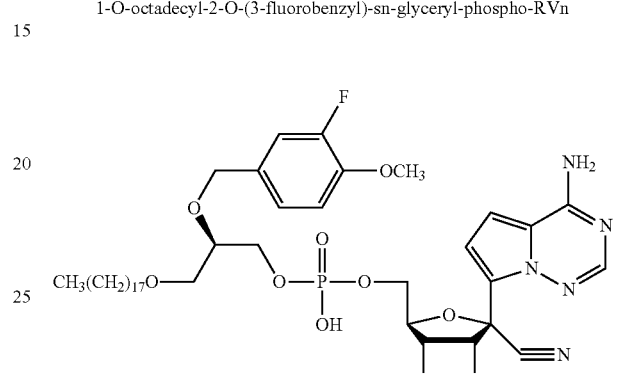

1-O-octadecyl-2-O-(3-fluoro, 4-methoxybenzyl)-sn-glyceryl-phospho-RVn

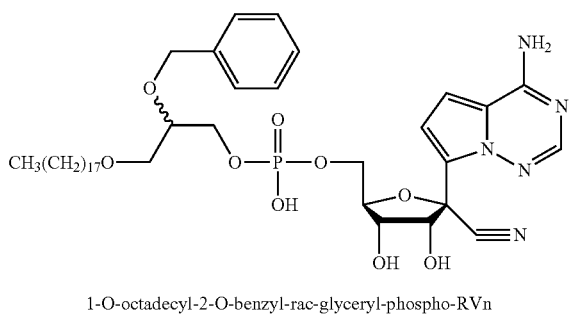

1-O-octadecyl-2-O-benzyl-rac-glyceryl-phospho-RVn

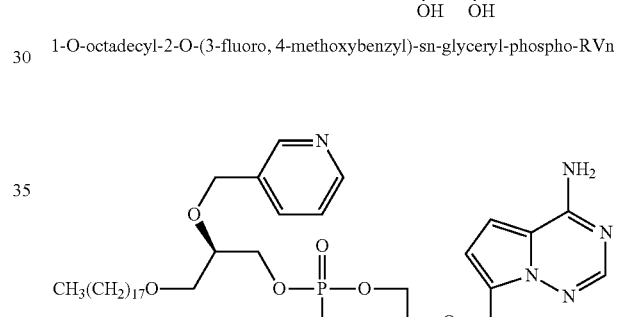

1-O-octadecyl-2-O-(methylpyridinyl)-sn-glyceryl-phospho-RVn

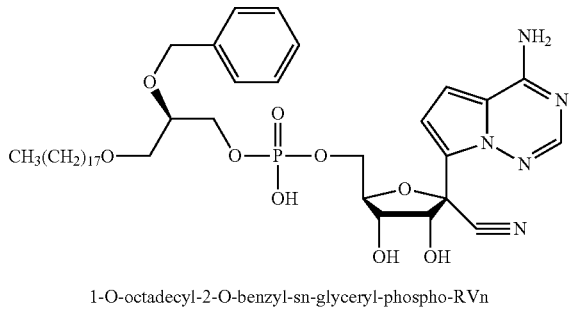

1-O-octadecyl-2-O-benzyl-sn-glyceryl-phospho-RVn

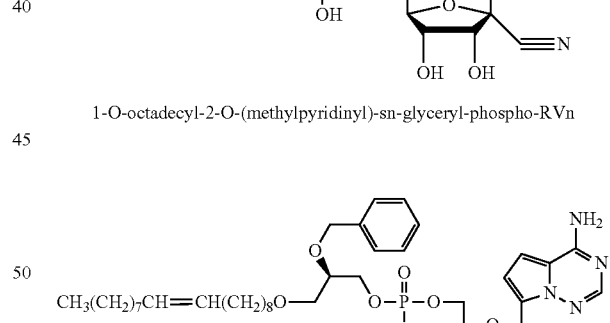

1-O-oleyl-2-O-benzyl-sn-glyceryl-phospho-RVn

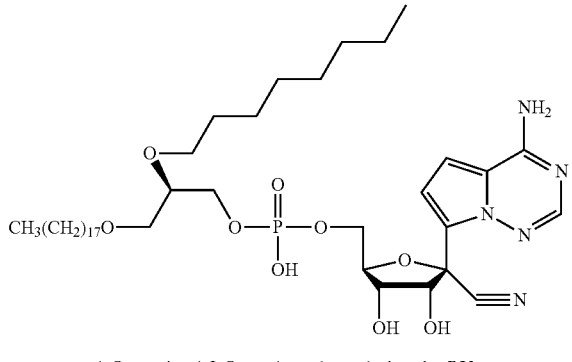

1-O-octadecyl-2-O-octyl-sn-glyceryl-phospho-RVn

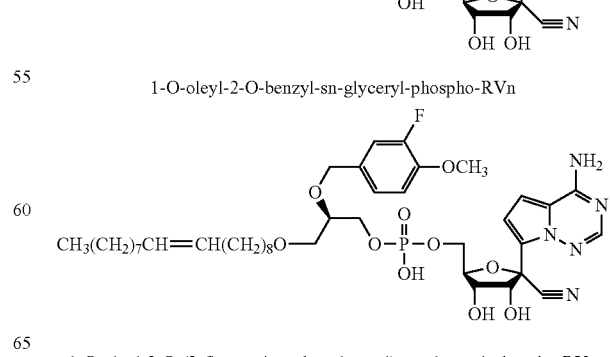

1-O-oleyl-2-O-(3-fluoro, 4-methoxybenzyl)-sn-glyceryl-phospho-RVn

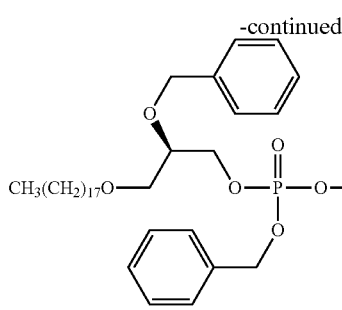

1-O-octadecyl-2-O-benzyl-benzyl-sn-glyceryl-phospho-RVn

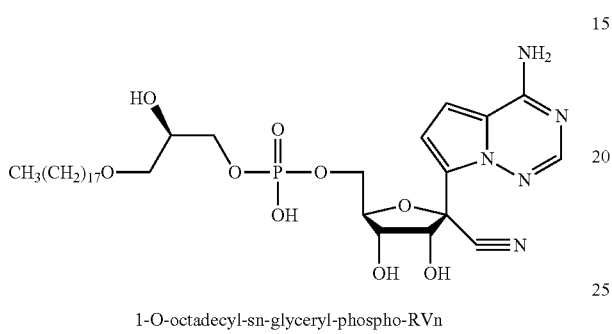

1-O-octadecyl-sn-glyceryl-phospho-RVn

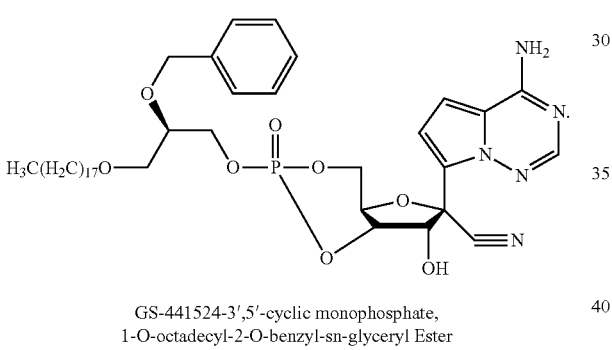

GS-441524-3',5'-cyclic monophosphate,
1-O-octadecyl-2-O-benzyl-sn-glyceryl Ester 27. A pharmaceutical formulation comprising the compound of claim 1.

28. The pharmaceutical formulation of claim 27, wherein the pharmaceutical formulation is orally bioavailable.

29. The pharmaceutical formulation of claim 27, wherein the pharmaceutical formulation is formulated for intramuscular injection.

30. A method for treating coronavirus infection in a mammal, the method comprising:
administering to the mammal an effective amount of the compound of claim 1.

31. A method for treating a virus infection in a mammal, the method comprising:
administering to the mammal an effective amount of a compound of the compound of claim 1,
wherein the virus is a RNA virus of a viral family selected from the group consisting of Filoviridae, Orthomyxoviridae, Paramyxoviridae, Pneumoviridae, Phenuiviridae, Nairoviridae, Arenaviridae, Flaviviridae, and Coronaviridae.

32. A method for producing a prodrug, the method comprising:

(i) providing a compound of formula (a)—

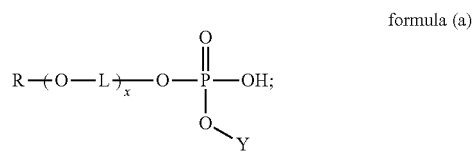

formula (a)

(ii) providing a compound of formula (b)—

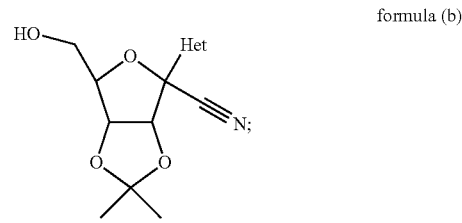

formula (b)

(iii) contacting the compound of formula (a) and the compound of formula (b) to form a compound of formula (c)—

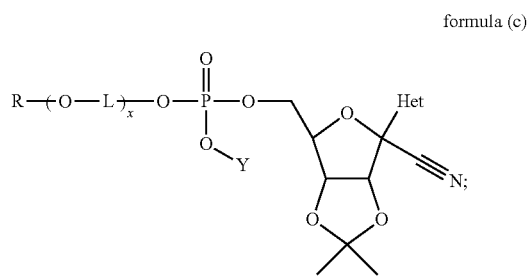

formula (c)

and (iv) contacting the compound of formula (c) with an acid to form a compound of formula (d)—

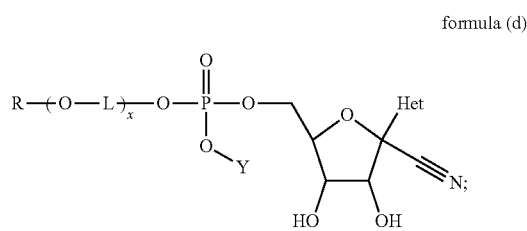

formula (d)

wherein—

Het is a $C_1$-$C_{30}$ hydrocarbyl comprising at least one heteroatom;

Y is selected from the group consisting of hydrogen, a $C_1$-$C_{30}$ hydrocarbyl, and a pharmaceutically acceptable cation;

x is 0 or 1;

L is a $C_1$-$C_6$ hydrocarbyl; and

R is selected from the group consisting of a $C_{10}$-$C_{30}$ hydrocarbyl and a substituent of formula (A);

formula (A)

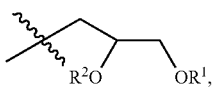

wherein $R^1$ and $R^2$ are independently selected from the group consisting of hydrogen and a $C_1$-$C_{30}$ hydrocarbyl.

33. The method of claim 32, wherein the contacting of the compound of formula (a) and the compound of formula (b) occurs in the presence of N,N-dicyclohexylcarbodiimide, 4-dimethylaminopyridine, or a combination thereof.

34. The method of claim 32, wherein the acid comprises HCl.

35. The method of claim 32, wherein the contacting of formula (c) with the acid occurs in the presence of tetrahydrofuran (THF).

36. The method of claim 32, wherein Het is—

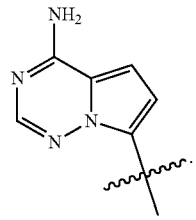 [SMILES: *c1ccc2c(N)ncnn12]

37. The method of claim 32, further comprising performing an intramolecular esterification reaction of the compound of formula (d) to form a cyclic phosphate.

38. The compound of claim 1, wherein the compound is 1-O-octadecyl-2-O-benzyl-sn-glyceryl-phospho-RVn:

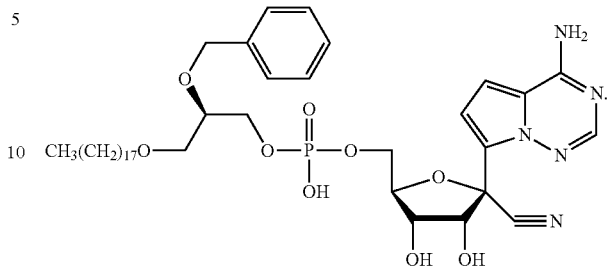

1-O-octadecyl-2-O-benzyl-sn-glycerl-phospho-RVn

39. The compound of claim 1, wherein the compound is 1-O-oleyl-2-O-(3-fluoro, 4-methoxybenzyl)-sn-glyceryl-phospho-RVn:

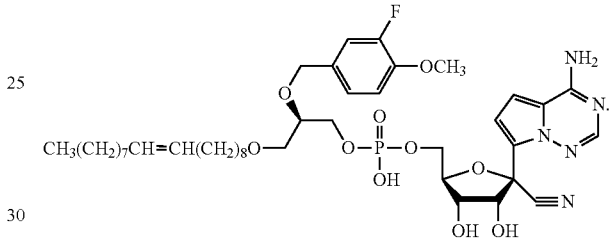

1-O-oleyl-2-O-(3-fluoro, 4-methoxybenzyl)-sn-glyceryl-phospho-RVn

* * * * *

UNITED STATES PATENT AND TRADEMARK OFFICE
CERTIFICATE OF CORRECTION

| | | |
|---|---|---|
| PATENT NO. | : 12,173,029 B2 | Page 1 of 1 |
| APPLICATION NO. | : 18/006330 | |
| DATED | : December 24, 2024 | |
| INVENTOR(S) | : Karl Y. Hostetler et al. | |

It is certified that error appears in the above-identified patent and that said Letters Patent is hereby corrected as shown below:

In the Specification

Column 1, Lines 21-23, please replace the paragraph under the STATEMENT REGARDING FEDERALLY SPONSORED RESEARCH OR DEVELOPMENT from "This invention was made with government support under grant no. AI131424 awarded by the National Institutes of Health. The government has certain rights in the invention." to --This invention was made with government support under AI131424 awarded by the National Institutes of Health. The government has certain rights in the invention.--

Signed and Sealed this
Twenty-fifth Day of November, 2025

John A. Squires
*Director of the United States Patent and Trademark Office*